(12) United States Patent
Melman et al.

(10) Patent No.: US 9,931,087 B2
(45) Date of Patent: Apr. 3, 2018

(54) X-RAY REDUCTION SYSTEM

(71) Applicant: Controlrad Systems Inc., Radnor, PA (US)

(72) Inventors: Haim Zvi Melman, Kfar Saba (IL); Allon Guez, Pen Valley, PA (US)

(73) Assignee: Controlrad Systems Inc., Radnor, PA (US)

( * ) Notice: Subject to any disclaimer, the term of this patent is extended or adjusted under 35 U.S.C. 154(b) by 0 days.

(21) Appl. No.: 14/650,916

(22) PCT Filed: Dec. 4, 2013

(86) PCT No.: PCT/IB2013/060626
§ 371 (c)(1),
(2) Date: Jun. 10, 2015

(87) PCT Pub. No.: WO2014/106783
PCT Pub. Date: Jul. 10, 2014

(65) Prior Publication Data
US 2015/0313558 A1   Nov. 5, 2015

Related U.S. Application Data

(60) Provisional application No. 61/748,091, filed on Jan. 1, 2013.

(51) Int. Cl.
*G01N 23/04* (2006.01)
*A61B 6/06* (2006.01)
(Continued)

(52) U.S. Cl.
CPC .............. *A61B 6/06* (2013.01); *A61B 6/4035* (2013.01); *A61B 6/4233* (2013.01); *A61B 6/469* (2013.01); *A61B 6/5205* (2013.01); *A61B 6/5258* (2013.01); *A61B 6/542* (2013.01); *A61B 6/545* (2013.01); *A61B 6/583* (2013.01); *A61B 6/585* (2013.01); *G06T 3/40* (2013.01); *G06T 5/009* (2013.01); *G21K 1/043* (2013.01); *A61B 6/46* (2013.01); *G06T 2207/10116* (2013.01);
(Continued)

(58) Field of Classification Search
None
See application file for complete search history.

(56) References Cited

U.S. PATENT DOCUMENTS 5,091,926 A * 2/1992 Horton ................ A61B 6/4476
250/338.1
5,332,908 A   7/1994 Weidlich
(Continued)

FOREIGN PATENT DOCUMENTS

DE       8118153 U1    1/1985

*Primary Examiner* — Andrew Smyth
(74) *Attorney, Agent, or Firm* — Gable Gotwals

(57) ABSTRACT

An x-ray system including an x-ray source, a detector having an input area, a monitor configured to display detected images, means for determining a location of a Region of Interest (ROI) of a patient on the displayed image; and a collimator having means for projecting the region of interest (ROI) on a selected fraction of the input area exposed by the x-ray source, the collimator movable in a plane parallel to the detector input area, the collimator includes a plurality of holes having different sizes, each one of the holes configured for projecting the selected fraction of the exposed area for a different zoom of the detector.

26 Claims, 37 Drawing Sheets

(51) Int. Cl.
*G06T 5/00* (2006.01)
*G06T 3/40* (2006.01)
*G21K 1/04* (2006.01)
*A61B 6/00* (2006.01)

(52) U.S. Cl.
CPC .............. *G06T 2207/20104* (2013.01); *G06T 2207/20208* (2013.01); *G06T 2210/41* (2013.01)

(56) References Cited

U.S. PATENT DOCUMENTS

| | | | | |
|---|---|---|---|---|
| 5,541,028 | A * | 7/1996 | Lee | G03C 5/02 358/445 |
| 5,627,869 | A * | 5/1997 | Andrew | A61B 6/502 378/150 |
| 6,480,565 | B1 * | 11/2002 | Ning | A61B 6/032 378/20 |
| 2002/0151781 | A1 * | 10/2002 | Ohishi | A61B 6/466 600/407 |
| 2003/0076920 | A1 * | 4/2003 | Shinno | A61B 6/032 378/4 |
| 2004/0101086 | A1 * | 5/2004 | Sabol | A61B 5/4872 378/4 |
| 2004/0101104 | A1 * | 5/2004 | Avinash | A61B 6/032 378/98.12 |
| 2005/0152499 | A1 | 7/2005 | Zhao et al. | |
| 2005/0163278 | A1 * | 7/2005 | Metz | A61B 6/032 378/4 |
| 2006/0052690 | A1 * | 3/2006 | Sirohey | A61B 6/481 600/420 |
| 2006/0067481 | A1 * | 3/2006 | Morton | A61B 6/06 378/151 |
| 2007/0140580 | A1 * | 6/2007 | Heath | H04N 19/39 382/260 |
| 2007/0206726 | A1 | 9/2007 | Lu et al. | |
| 2008/0010154 | A1 | 1/2008 | Tietzen et al. | |
| 2008/0036893 | A1 * | 2/2008 | De Godzinsky | H04N 3/1562 348/311 |
| 2008/0101545 | A1 * | 5/2008 | Petrik | G21K 1/025 378/148 |
| 2010/0067766 | A1 * | 3/2010 | Vija | G06T 11/006 382/131 |
| 2010/0119033 | A1 * | 5/2010 | Li | A61B 6/06 378/5 |
| 2011/0013742 | A1 * | 1/2011 | Zaiki | A61B 6/035 378/15 |
| 2011/0058653 | A1 * | 3/2011 | Baumgart | G06T 19/00 378/98.2 |
| 2011/0158384 | A1 * | 6/2011 | Beekman | G01T 1/1648 378/37 |
| 2012/0128120 | A1 * | 5/2012 | De Man | A61B 6/032 378/16 |
| 2012/0140886 | A1 | 6/2012 | Murakoshi et al. | |
| 2012/0187312 | A1 * | 7/2012 | Guez | A44C 5/20 250/492.1 |
| 2013/0101084 | A1 * | 4/2013 | Shimizu | A61B 6/022 378/42 |
| 2013/0336445 | A1 * | 12/2013 | Sehnert | A61B 6/06 378/42 |

\* cited by examiner

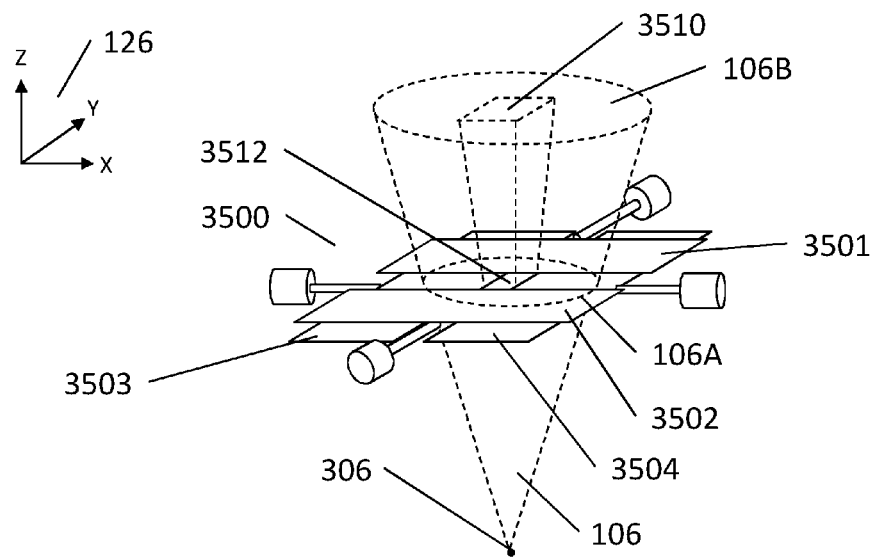
Figure 35A
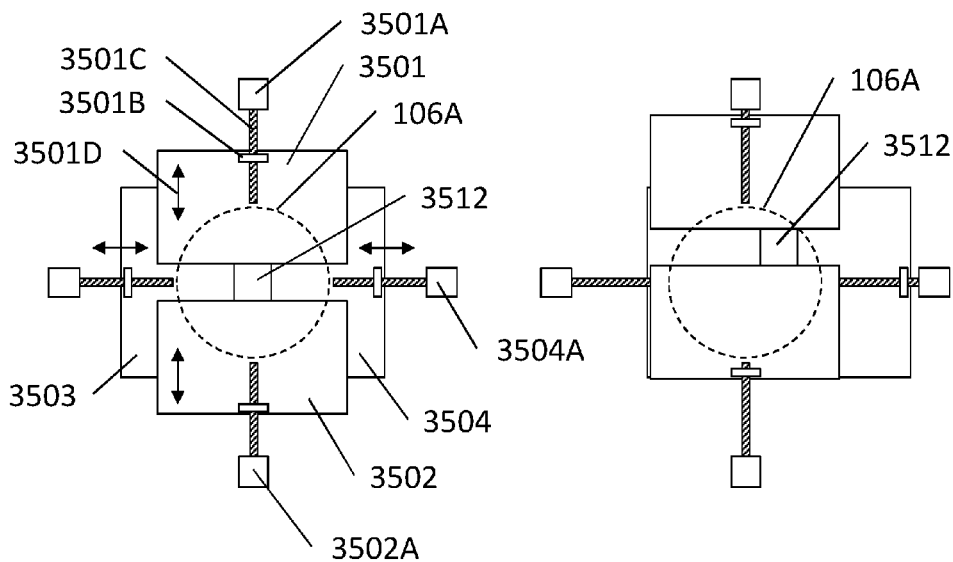
Figure 35B
Figure 35C

X-RAY REDUCTION SYSTEM

CROSS-REFERENCE TO RELATED APPLICATIONS

This application is the United States National Phase of Patent Application No. PCT/IB2013/060626 filed 4 Dec. 2013, which claims priority to U.S. Provisional Patent Application No. 61/748,091 filed 1 Jan. 2013, each of which are incorporated herein by reference.

BACKGROUND OF THE INVENTION

Field of the Invention

The invention is related to the field of multiple frame x-ray imaging and more particularly to the field of controlling x-ray radiation amount during multiple frame x-ray imaging.

In a typical multiple frame x-ray imaging system the x-ray tube generates x-ray radiation over a relatively wide solid angle. To avoid unnecessary exposure to both the patient and the medical team, collimators of x-ray absorbing materials such as lead are used to block the redundant radiation. This way only the necessary solid angle of useful radiation exits the x-ray tube to expose only the necessary elements.

Such collimators are used typically in a static mode but may assume a variety of designs and x-ray radiation geometry. Collimators can be set up manually or automatically using as input, for example, the dimensions of the organ environment that is involved in the procedure.

In multiple frame x-ray imaging the situation is more dynamic than in a single exposure x-ray. The x-ray radiation is active for relatively long period and the treating physician typically has to stand near the patient, therefore near the x-ray radiation. As a result, it is desired to provide methods to minimize exposure to the medical team. Methods for reducing x-ray radiation intensity have been suggested where the resultant reduced signal to noise ratio (S/N) of the x-ray image in compensated by digital image enhancement. Other methods suggest a collimator limiting the solid angle of the x-ray radiation to a fraction of the image intensifier area and moving the collimator to swap the entire input area of the image intensifier where the Region of Interest (ROI) is exposed more than the rest of the area. This way, the ROI gets high enough x-ray radiation to generate a good S/N image while the rest of the image is exposed with low x-ray intensity, providing a relatively low S/N image. The ROI size and position can be determined in a plurality of methods. For example, it can be a fixed area in the center of the image or it can be centered automatically about the most active area in the image, this activity is determined by temporal image analysis of s sequence of cine images received from the video camera of the multiple frame x-ray imaging system.

SUMMARY OF THE INVENTION

According to a first aspect of the present invention there is provided an x-ray system incorporating an x-ray source, a detector, a monitor for displaying an x-ray image of a field of view and an eye tracker wherein said eye tracker is configured to provide user's gazing coordinates in the image area; said system configured to determine a Region of Interest (ROI) so that the gazing point is contained in said ROI; and to optimize the image displayed on said monitor according to the image part that is contained in said ROI.

The image optimization may be made by controlling any of the following parameters: x-ray tube current (whether in continuous or pulse modes); x-ray tube Peak Kilo Voltage (PKV); x-ray pulse length; AGC (Automatic Gain Control), whether analog or digital; Tone reproduction of the image implemented in brightness function; Tone reproduction of the image implemented in contrast function; Tone reproduction of the image implemented in brightness function; Tone reproduction of the image implemented in gamma function; Tone reproduction of the image implemented in offset function; Tone reproduction of the image implemented in n-degree linear function; and Tone reproduction of the image implemented in a non-linear function.

The x-ray system may further include a collimator, which may be configured to modify the x-ray radiation dose per pixel (DPP) in the field of view according to the location of the gazing point.

The x-ray system may further include a collimator, which may be configured to modify the dose per pixel (DPP) in the field of view according to the location of the gazing point.

According to a second aspect of the present invention there is provided an x-ray system incorporating an x-ray source, a detector, a monitor for displaying an x-ray image and a collimator; said collimator is configured to expose a first area to a first radiation level and a second area to a second radiation level; and said system configured to process said second area to become similar to said first area using a tone-correction function.

The tone-correction functions may be one of at least two tone-correction functions, each of the tone-correction functions is associated with a specific PKV.

The system may further be configured to create a tone-correction function by interpolation of two other tone-correction functions, each of the other tone-correction functions associated with a specific PKV.

The system may further be configured to estimate a tone-correction function for a third area from the tone-correction function used for said second area. The estimation may use exponential calculation.

The system may further be configured to adjust the input scale of the tone-correction function to fit changes in x-ray current.

The adjustment may be made using a factor equal to the relative change of the x-ray current.

According to a third aspect of the present invention there is provided a method of calculating a tone-correction function including: exposing a first area to a first x-ray radiation and a second area to a second x-ray radiation, wherein at least a part of said first and second radiation is through a variable absorption phantom so that for each designated transmission level of said phantom there is at least one area exposed by said first radiation and at least one area exposed by said second radiation; for each such designated transmission level calculating the average pixel value; calculating the ratio of said two average pixel values for all designated absorption levels; and fitting a function to the said calculated ratios to be used as the tone-correction function.

The variable absorption phantom may be a step wedge.

The variable absorption phantom may be a variable thickness phantom of continuous slope function.

According to a fourth aspect of the present invention there is provided a method of calculating a tone-correction function including: exposing an area to a first x-ray radiation and exposing said area to a second x-ray radiation, wherein said first and second radiation is through a human tissue in said area; calculating the ratio of at least one pixel value in said area corresponding to said first radiation to the corresponding pixel value in said area corresponding to said second radiation; and fitting a function to the said at least one calculated ratio and pixel value in said area corresponding to said second radiation to be used as a first tone-correction function.

More than one area is used.

A second tone-correction function may calculated, using also data that was acquired after the acquisition of the data used to calculate said first tone-correction function.

The data used to calculate said first tone-correction function may be from at least 2 patients.

According to a fifth aspect of the present invention there is provided an x-ray system incorporating an x-ray source, a collimator, a detector and a monitor, means for moving said collimator in a plane generally parallel to the plane of said collimator; said collimator comprising an aperture that allows all the radiation to pass through, an outer annulus that reduces the radiation passing through at an amount depending on the material and the thickness of the said outer annulus and an inner annulus between said aperture and said outer annulus, with thickness changing as a function of the distance from the said aperture, starting at a low thickness on the side of the aperture and ending at the thickness of the outer annulus on the side of the outer annulus; and the system configured to modify image data so as to essentially adjust the image acquired through the inner annulus and the image acquired through the outer annulus to appear visually similar to the image acquired through said aperture, wherein parameters used for said adjustments depend on the position of said collimator. The system may be configured to acquire said parameters by a calibration procedure, said calibration procedure includes measurements made at a variety of said collimator positions.

The variety of collimator positions may include a variety of positions in the collimator plane.

The variety of collimator positions may include a variety of distances from the x-ray source.

The internal annulus thickness may be essentially symmetrical relative to a plane that is located essentially midway between the two external surfaces of said outer annulus.

The system may include a layer of material that is different from the material of the outer annulus, said layer located at said aperture area.

The layer may overlaps at least a part of said inner annulus.

According to a sixth aspect of the present invention there is provided an x-ray system incorporating an x-ray source, a detector, a monitor for displaying an x-ray image, a collimator and an input device; wherein said input device is configured to provide coordinates relative to the x-ray image; the system configured to select a region of the image according to said coordinates; and adjust at least one of the following parameters according to said coordinates: said region shape; and said region position.

The system may further be configured to adjust at least one of the following parameters according to said region: x-ray tube mA; x-ray tube mAs; x-ray tube KVp; said x-ray image brightness; said image contrast; and said image tone.

The input device may be at least one of: an eye tracker; a joy-stick; a keyboard; an interactive display, a gesture reading device; and a voice interpreter.

BRIEF DESCRIPTION OF THE DRAWINGS

The invention will be better understood in reference to the following Figures:

FIG. 35A provides a view of a collimator constructed of 4 partially x-ray transparent plates;

FIG. 35B is a top view of the collimator of FIG. 35A with the ROI at the center;

FIG. 35C is a top view of the collimator of FIG. 35A with the ROI at an off-center location;

DETAILED DESCRIPTION OF THE INVENTION

Figure 1A:
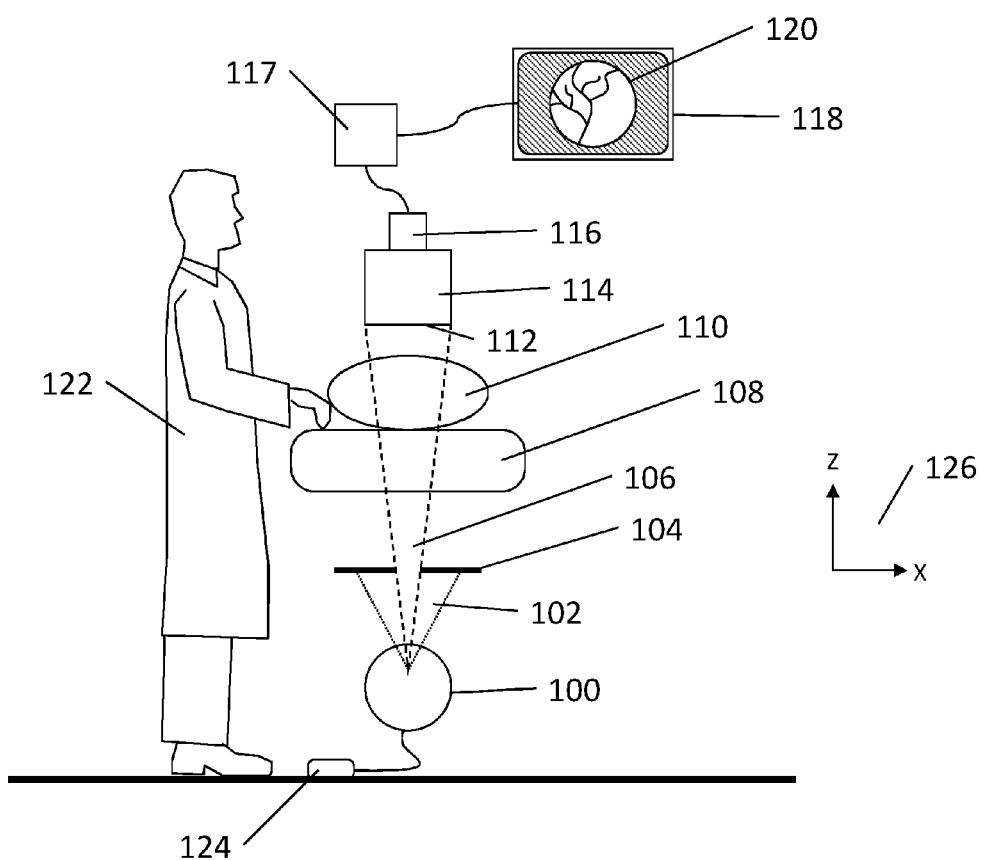
FIG. 1A is a simplified schematic illustration of an example layout of a multiple frame x-ray imaging clinical environment and system.

Reference is made now to FIG. 1A which presents a typical layout of a multiple frame x-ray imaging clinical environment X-ray tube 100 generates x-ray radiation 102 directed upward occupying a relatively large solid angle towards collimator 104. Collimator 104 blocks a part of the radiation allowing a smaller solid angle of radiation to continue in the upward direction, go through bed 108 that is typically made of material that is relatively transparent to x-ray radiation and through patient 110 who is laying on bed 108. part of the radiation is absorbed and scattered by the patient and the remaining radiation arrives at the typically round input area 112 of image intensifier 114. The input area of the image intensifier is typically in the order of 300 mm in diameter but may vary per the model and the technology. The image generated by image intensifier 114 is captured by camera, 116 processed by image processor 117 and then displayed on monitor 118 as image 120.

Although the invention is described mainly in reference to the combination of image intensifier 114 and camera 116 it would be appreciated that both these elements can be replaced by a digital radiography sensor of any technology such as CCD or CMOS flat panels or other technologies such as Amorphous Silicon with scintillatiors located at plane 112. One such example is CXDI-50RF Available from Canon U.S.A., Inc., Lake Success, N.Y. The term "detector" will be used to include any of these technologies, including the combination of any image intensifier with any camera and including any type of a flat panel sensor or any other device converting x-ray to electronic signal. The terms "area" and "region" are used alternatively in the detailed description of the invention any they mean the same and are used as synonyms.

The term "x-ray source" will be used to provide a wide interpretation for a device having x-ray point source that does not necessarily have the shape of a tube. Although the term x-ray tube is used in the examples of the invention in convention with common terminology in the art, it is represented here that the examples of the invention are not limited to a narrow interpretation of x-ray tube and that any x-ray source can be used in these examples (for example even radioactive material configured to function as a point source).

Operator 122 is standing by the patient to perform the medical procedure while watching image 120.

The operator has a foot-switch 124. When pressing the switch, continuous x-ray radiation (or relatively high frequency pulsed x-ray as explained below) is emitted to provide a cine imaging 120. The intensity of x-ray radiation is typically optimized in a tradeoff of low intensity that is desired to reduce exposure to the patient and the operator and high intensity radiation that is desired to enable a high quality image 120 (high S/N). With low intensity x-ray radiation and thus low exposure of the image intensifier input area, the S/N of image 120 might be so low that image 120 becomes useless.

Coordinate system 126 is a reference Cartesian coordinate system with Y axis pointing into the page and X-Y is a plane parallel to planes such as that of collimator 104 and image intensifier input plane 112.

It is a purpose of the present invention to provide high exposure at the input area of the image intensifier in the desired ROI that will provide therefore a high S/N image there while reducing the exposure of other sections of the image intensifier area, at the cost of lower image quality (lower S/N). With this arrangement the operator can see a clear image in the ROI and get a good enough image for general orientation in the rest of the image area. It is also the purpose of this invention to provide more complex map of segments in the image where each segment results from a different level of x-ray radiation as desired by the specific application. It is also the purpose of the current invention to provide various methods to read the data off the image sensor. In the context of the examples provided throughout the detailed description of the invention, when S/N of one area is compared to S/N in another area the S/N are compared for pixels that have the same object (such as patient and operators hands and tools) transmittance. For example, when an area A is described as having lower S/N than area B it is assumed that the transmission of x-ray by the object to both areas is uniform over the area and is the same. For example, at the center of the area A only ½ of the radiation arriving at the object is transmitted through to the image intensifier then, S/N in area B is compared to area A for an area B that also only ½ of the radiation arriving at the object is transmitted through to the image intensifier. The S (signal) of area A is the average reading value of the area A (average over time or over the area if it includes enough pixels in the statistical sense. The S (signal) of area B is the average reading value of the area B (average over time or over the area if it includes enough pixels in the statistical sense. To simplify discussion scattered radiation is not considered in the detailed description of the invention. The affect of scattered radiation and means to reduce it are well known in the art.

In the examples below the noise statistics is assumed to be of Gaussian distribution which satisfies most practical aspects of implementation of the invention and serves well clear presentations of examples of the detailed description of the invention. This is not a limitation of the invention and, if desired, the mathematics presented in association to Gaussian statistics can be replaced by that of Poisson statistics (or other statistics) without degrading the scope of the invention. The noise values associated with each signal are represented by the standard deviation of the Poisson statistics for that signal, known in the art as Poisson Noise.

Also dose per pixel (DPP) throughout the detailed description of the invention is discussed in the same sense, i.e. the when the DPP of pixel A is compared to DPP of pixel B it is assumed the object transmission for both pixels is the same.

Figure 1B:
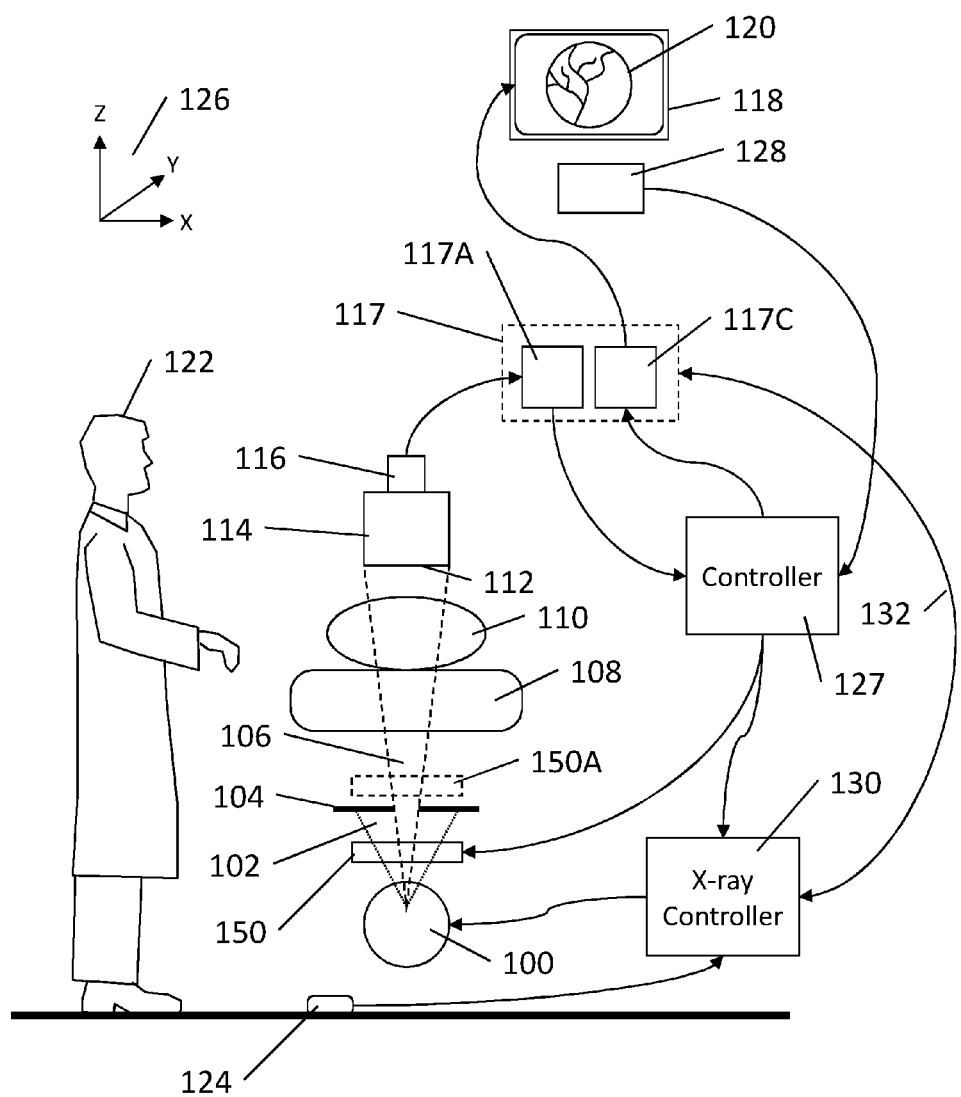
FIG. 1B is an illustration of an example of a layout of the system of FIG. 1A showing additional details of components of the system example of the invention.
Figure 27:
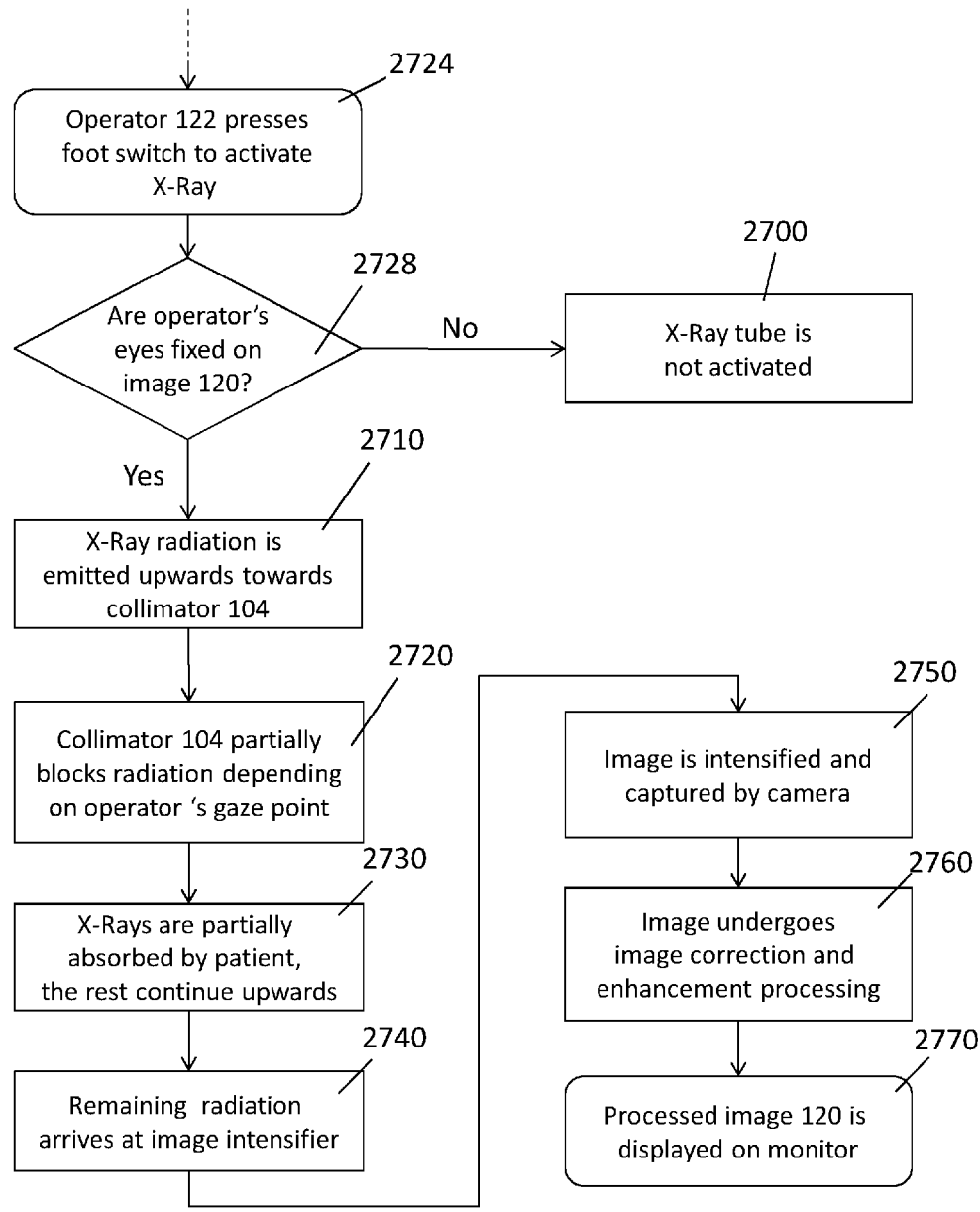
FIG. 27 is a flowchart referencing FIG. 1A, describing the basic multiple frame x-ray imaging process using an eye tracker.

An example of a more detailed layout of a multiple frame x-ray imaging clinical environment according to the present invention is described in FIGS. 1B and 27. Operator 122 presses foot switch 124 to activate x-ray (step 2724). Eye tracker 128 (such as EyeLink 1000 available from SR Research Ltd., Kanata, Ontario, Canada) or any alternative input device provides indication where operator 122 is looking (step 2728). This information is typically provided relative to monitor 118. This information, the "gazing point", may be provided for example in terms of (X,Z) coordinates, in the plane of monitor 118, using coordinate system 126. It would be appreciated that in this example the plane of monitor 118 and therefore also image 120 are parallel to the (X,Z) plane of coordinate system 126. Other coordinate systems are possible, including coordinate systems that are bundled to monitor 118 and rotate with monitor 118 when it is rotated relative to coordinate system 126.

The data from input 128 is provided to controller 127 which is basically a computer, such as any PC computer. If the controller 127 determines that the operator's gaze is not fixed on the image 120, the x-ray tube 100 is not activated (step 2700). Otherwise, in step 2710, x-ray tube 100 is activated and x-ray radiation is emitted towards collimator 104 (and/or 150/150A).

Box 150 in FIG. 1B represents a collimator according to the present invention, for example, the collimator of FIG. 5, FIG. 10A through FIG. 10C, FIG. 11A through FIG. 11D, FIG. 12A through 12B, FIG. 13A through FIG. 13B, FIG. 14A through 14B, FIG. 15A through 15D, FIG. 16A through 16D, FIG. 18A through 18C, FIG. 20A through 20B, FIG. 24A through 24B and FIG. 25.

Box 150 can be located under collimator 104, above collimator 104 as shown by numerical reference 150A or instead of collimator 104 (not shown in FIG. 1B). The collimators represented by boxes 150 and 150A are controlled by controller 127. X-ray emission is also controlled by controller 127, typically through x-ray controller 130. In one example, x-ray can be stopped even if operator 122 presses foot-switch 124 if the operator's gazing point is not within image 120 area. The collimator partially blocks radiation, depending on the determined operator's gazing point (step 2720). Part of the x-rays are absorbed by the patient 110 (step 2730) and the remaining radiation arrives at the image intensifier 114 (step 2740). In step 2750 the image is intensified and captured by a camera 116 and in step 2760 the captured image is transferred to the image processor 117 and in step 2770 the processed image is displayed on monitor 120.

Image processor 117 may assume many forms and may be incorporated in the current invention in different ways. In the example of FIG. 1B, image processor 117 includes two main sub units: 117A provides basic image correction such as pixel non-uniformity (dark offset, sensitivity, reconstruction of dead pixels etc), 117C provides image enhancement processing (such as noise reduction, un-sharp masking, gamma correction etc). In conventional systems, the image from sub-unit 117A is transferred for further processing in sub-unit 117C. The sub-units of image processor 117 can be supported each by a dedicated hardware but they can also be logical sub-units that are supported by any hardware.

In the example of FIG. 1B the image from camera 116 is corrected by image processing sub-unit 117A and then transferred to controller 127. Controller 127 processes the image as required from using any of the collimators represented by box 150 and returns the processed image to sub-unit 117C for image enhancement.

It would be appreciated that the image processing of controller 127 does not have to take place in controller 127 and it can be executed by a third sub-unit 117B (not shown in FIG. 1B) located between 117A and 117C. Sub-unit 117B can also be only a logical unit performed anywhere in image processor 117.

It would also be appreciated that x-ray controller 130 is presented here in the broad sense of system controller. As such it may also communicate with image processor 117 to determine its operating parameters and receive information as shown by communication line 132, It may control image intensifier 114, for example for zoom parameters (communication line not shown), it may control camera 116 parameters (communication line not shown), it may control the c-arm and bed position (communication line not shown) and it may control x-ray tube 100 and collimator 104 operation parameters (communication line not shown).

Figure 26:
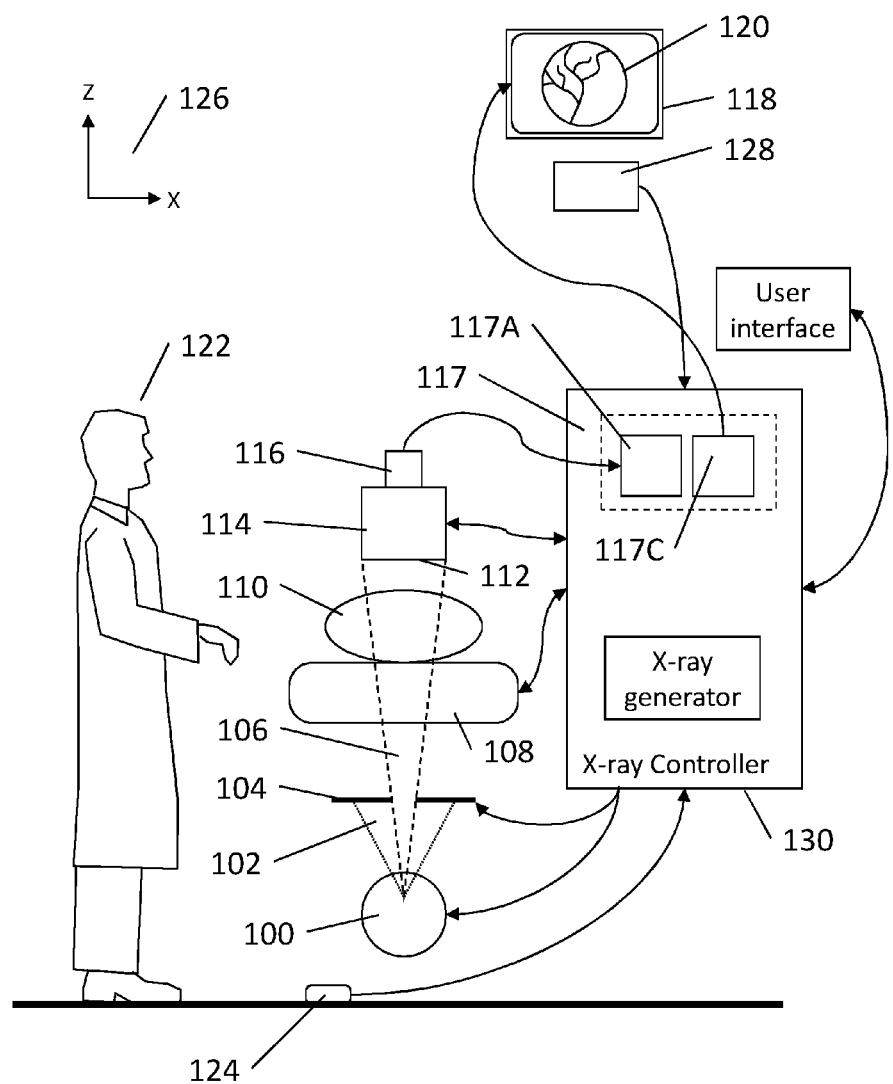
FIG. 26 is a simplified schematic illustration of an example layout of a multiple frame x-ray imaging clinical environment and system with the addition of an eye tracker.

There may be a user interface for operator 122 or other staff members to input requests or any other needs to x-ray controller 130 (not shown). Physically, part or all of image processor 117, controller 127 and x-ray generator (the electrical unit that drives x-ray tube 100) may all be included in x-ray controller 130. X-ray controller 130 may contain one or more computers and suitable software to support the required functionality. An example for such a system with an x-ray controller is mobile c-arm OEC 9900 Elite available from GE OEC Medical Systems, Inc., Salt Lake City, Utah USA. It would be appreciated that the example system is not identical to the system of FIG. 1B and is only provided as a general example. Part of these features are shown in FIG. 26.

Figure 2:
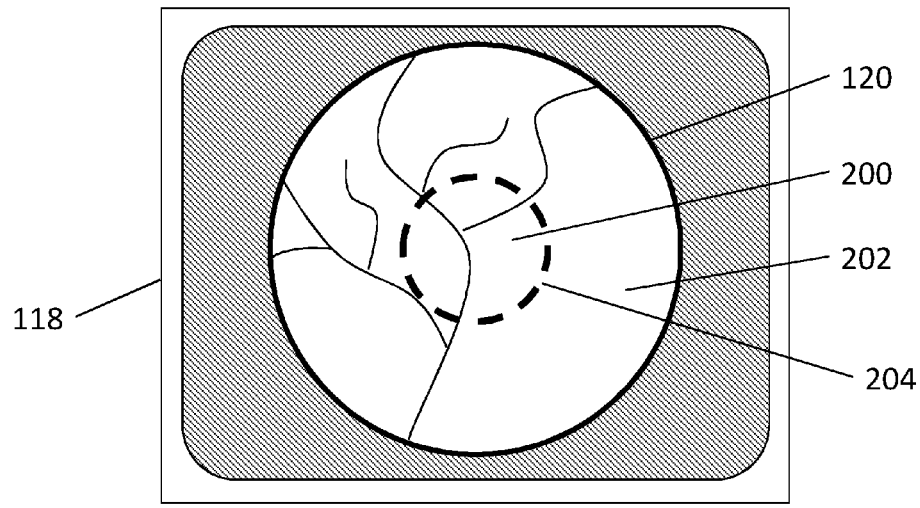
FIG. 2 is a schematic illustration of an example of image displayed on a monitor of a multiple frame x-ray imaging system.

Reference is made now to FIG. 2 illustrating an example of an image 120 displayed on monitor 118. In this example dashed circle line 204 indicates the border between segment 200 of the image and segment 202 of the image, both segments constitute the entire image 120. In this example it is desired to get a good image quality in segment 200 meaning higher x-ray DPP for segment 200 and it is acceptable to have a lower image quality in segment 202, meaning lower DPP for segment 202.

It would be appreciated that the two segments 200 and 202 are provided here only as one example of an embodiment of the invention that is not limited to this example and that image 120 can be divided to any set of segments by controlling the shape of the apertures in the collimators and mode of motion of the collimators. Such examples will be provided below.

It would be appreciated that DPP should be interpreted as the x-ray dose delivered towards a segment representing one pixel of image 120 to generate the pixel readout value used to construct image 120 (excluding absorption by the patient or other elements which are not a part of the system, such as the hands and tools of the operator).

Figure 3:
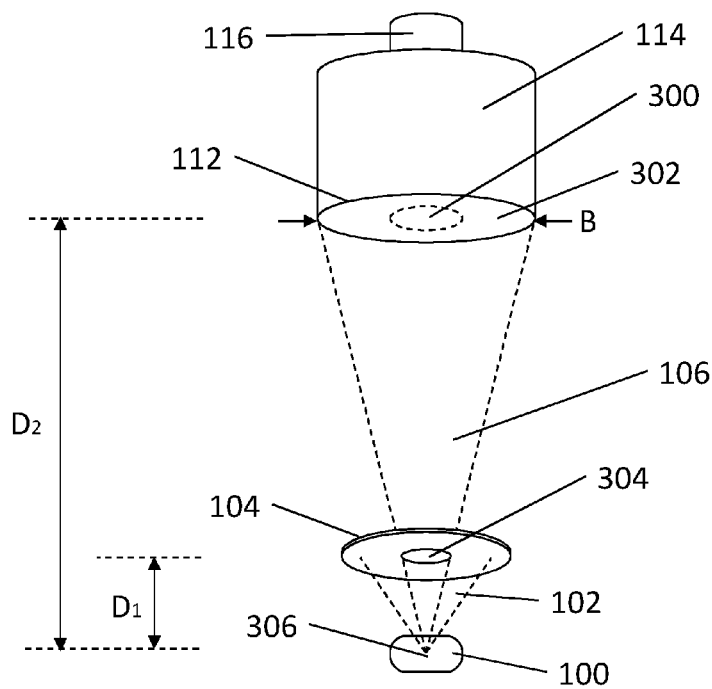
FIG. 3 is a schematic illustration of additional aspects of the system example of FIG. 1A.

Reference is made now to FIG. 3. A typical collimator 104 having a round aperture 304 is introduced to the x-ray path so that only x-rays 106 that are projected from focal point 306 of x-ray tube 100 and pass through aperture 304 arrive at the round input surface 112 of image intensifier 114 while other x-rays 102 are blocked by the collimator. This arrangement exposes the entire input area 112 of the image intensifier to generally the same DPP. Such an arrangement does not provide the function of one DPP to segment 300 that correlates with segment 200 of FIG. 2 and another DPP to segment 302 that correlates with segment 202 of FIG. 2. The diameter of input area 112 is B as indicated in FIG. 3.

D1 represents the distance from the x-ray focal point 306 to aperture 104. D2 represents the distance from the x-ray focal point 306 to image intensifier input surface 112.

Figure 4:
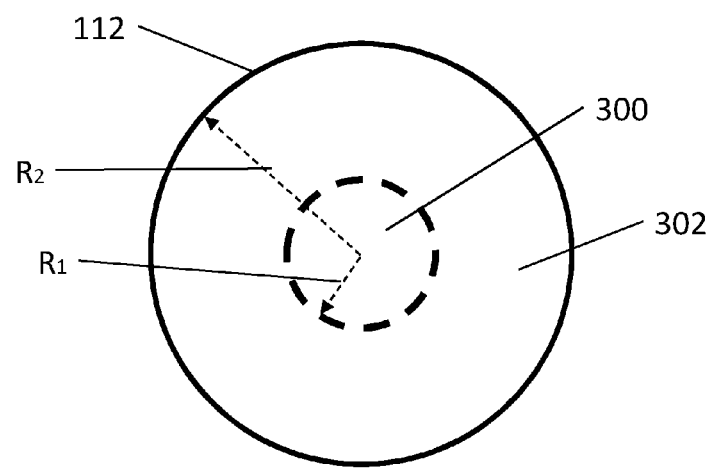
FIG. 4 is a schematic illustration of an example of x-ray exposure regions of the detector in reference to the parameters of FIG. 3.

Reference is made now to FIG. 4 that defined the segments of the current example of the image intensifier input surface 112 to support an example of the invention. In this example segment 300 is a circular area of radius R1 centered on circular input area 112 of the image intensifier. Segment 302 has an annulus shape with internal radius R1 and external radius R2. R2 is also typically the radius of the input area of the image intensifier.

Figure 5:
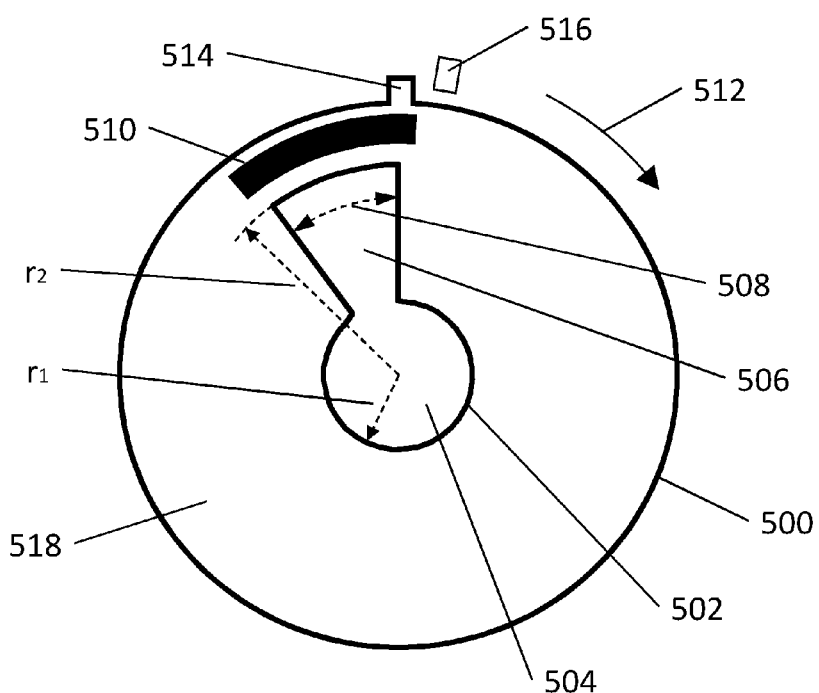
FIG. 5 is a schematic illustration of an example of a collimator according to the present invention.

Reference is made now to FIG. 5 that provides one embodiment of a collimator that functions to provide one DPP for segment 300 and another DPP for segment 302.

Collimator 500 is constructed basically as a round plate of x-ray absorbing material (such as lead, typically 1-4 mm thick), of a radius larger than r2. Aperture 502 of collimator 500 is constructed as a circular cut-out 504 of radius r1 at the center of the collimator and a sector cut-out 506 of radius r2 and angle 508. It would be appreciated that the term sector is used both to indicate a sector of a circular area and a sector of an annulus shaped area, as per the context.

In this example, r1 and r2 of aperture 502 are designed to provide R1 and R2 of FIG. 4. When collimator 500 is positioned in the location of collimator 104 of FIG. 4 r1 and r2 can be calculated using the following equations:

$r1 = R1/(D2/D1)$ $r2 = R2/(D2/D1)$

In this example angular span 508 is 36 degrees, 1/10 of a circle. Collimator 500 can rotate about its center as shown by arrow 512. Weight 510 can be added to balance collimator 500 and ensure that the center of gravity coordinates in the plane of the collimator coincide with the center of rotation, thus avoiding vibrations of the system that might result from an un-balanced collimator. Following a completion of one 360 degrees rotation, DPP for segment 302 is 1/10 of the DPP of segment 300.

It would be appreciated that angle 508 can be designed to achieve any desired of DPP ratios. For example, if angle 508 is designed to be 18 degrees, following one complete rotation of aperture 500 the DPP for segment 302 will be 1/20 of the DPP of segment 300. The discussion of the current example will be made in reference to angle 508 being 36 degrees. Following the completion of one rotation of collimator 500, camera 116 captures one frame of the data integrated by the sensor over the one complete rotation time of collimator 500, such a frame consists of the values read from the set of pixels of the camera sensor. This will be described in more details now, providing as an example a camera based on a CCD (charge coupled device) sensor such as TH 8730 CCD Camera available from THALES ELECTRON DEVICES, Vélizy Cedex, France.

In this example, synchronization of the camera 116 with collimator 500 rotation is made using tab 514 constructed on collimator 500 that passes through photo-sensor 516 such as EE-SX3070 available from OMRON Management Center of America, Inc., Schaumburg, Ill., U.S.A.

When tab 514 interruption signal is received from photo sensor 516, the lines of camera 116 sensor are transferred to their shift registers and the pixels start new integration cycle. The data of the previous integration cycle is read out from the camera. When tab 514 interrupts photo sensor 516 again, the accumulated signals are transferred again to the shift registers of camera sensor 116 to be read out as the next frame.

Through this method, one frame is generated for each collimator complete round. For each frame the DPP in segment 202 of image 120 is 1/10 the DPP in segment 200 of image 120.

Figure 6:
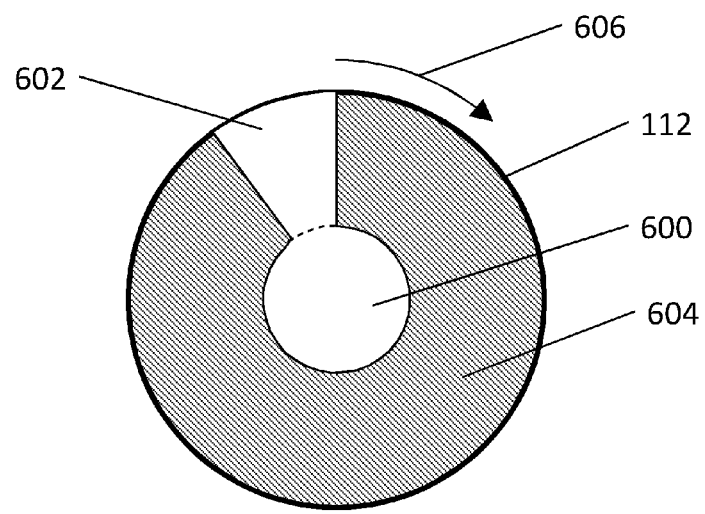
FIG. 6 is a schematic illustration of an example of the exposed region of the image intensifier at a certain rotation angle of the collimator of FIG. 5.
Figure 7:
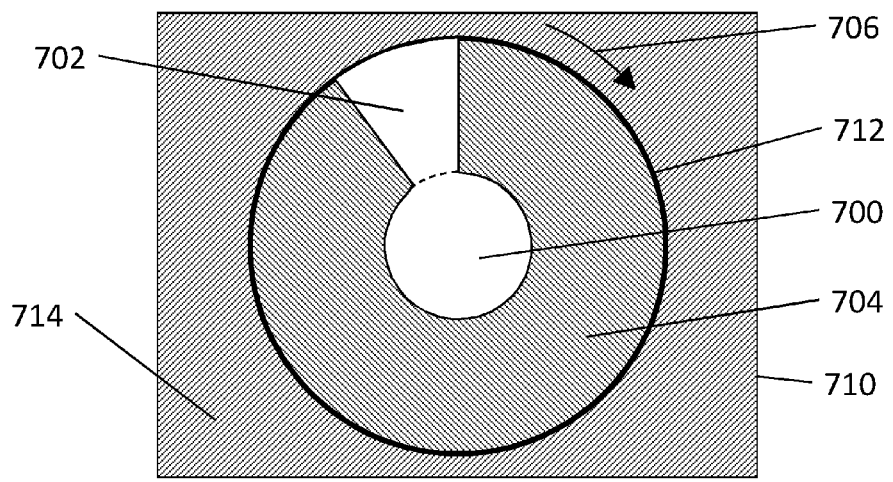
FIG. 7 is a schematic illustration of an example of the light exposure pattern of the sensor at a certain rotation angle of the collimator of FIG. 5.

To provide additional view of the above, reference is made to FIG. 6 that describes the exposure map of image intensifier input 112 at a momentary position of the rotating collimator 500. In this position circular area 600 and sector area 602 are exposed to radiation while the complementary sector 604 is not exposed to radiation being blocked by collimator 500. As collimator 500 rotates, sector area 602 and 604 rotate with it while circular area 600 remains unchanged. During one cycle of constant speed of rotation of collimator 500, each pixel outside of area 600 is exposed to x-ray for 1/10 of the time of a pixel in area 600 and thus, receives DPP that is 1/10 than a pixel of area 600. In FIG. 7 the equivalent optical image projected on the camera sensor 710 is shown, where area 700 of FIG. 7 is the equivalent of area 600 of FIG. 6, area 702 of FIG. 7 is the equivalent of area 602 of FIG. 6. The output image of image intensifier projection on sensor 710 is indicated by numerical indicator 712. 714 is a typical sensor area that is outside the range of the image intensifier output image.

For each frame, in addition to typical offset and gain correction to compensate per pixel linear response characteristics, a multiplication by a factor of 10 of the signal from pixels of segment 202 would be needed to generate an image 120 so that the brightness and contrast appearance of segment 202 would be similar to that of segment 200. This method described here in reference to a specific example will be called "normalization" of the pixels. Normalization scheme is made in accordance to the x-ray exposure scheme (i.e., collimator shape, speed and position).

To generate a cine of 10 frames per second (fps) collimator 500 has to be rotated as a speed of 10 rounds per second (rps). To generate a cine of 16 fps collimator 500 has to be rotated as a speed of 16 rps.

With each such rotation of 360 degrees a complete exposure of input area 112 is completed. An Exposure Cycle (EC) is therefore defined to be the smallest amount of rotation of collimator 500 to provide the minimal complete designed exposure of input area 112. In the example of collimator 500 of FIG. 5, EC requires a rotation of 360 degrees. For other collimator designs such as the one of FIG. 13A EC requires 180 degrees rotation and the one of FIG. 13B EC requires 120 degrees rotation.

Figure 28A:
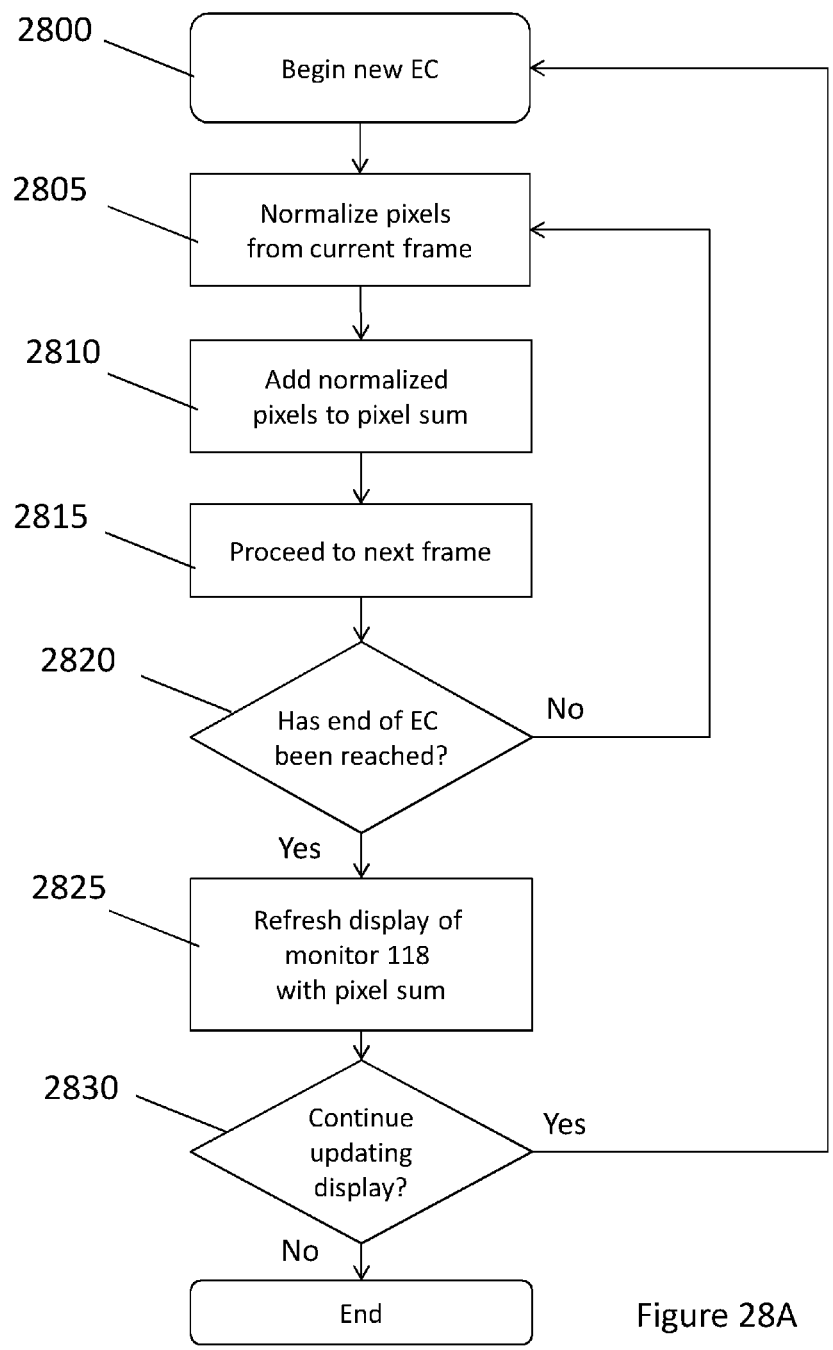
FIG. 28A is a flowchart describing a method for displaying the complete data from one EC using multiple frames, performing normalization on each frame separately.

It would be appreciated that the examples of collimators, x-ray projections on image intensifier input area 112, the images projected on the camera sensor (or flat panel sensor) and the images displayed on monitor 118 are described in a general way ignoring possible geometrical issues such as image up-side down due to lens imaging that might be different if a mirror is also used or the direction of rotation that is shown clockwise throughout the description but depending on the specific design and orientation of the observer might be different. It is appreciated that a person skilled in the art understands these options and has the proper interpretation for any specific system design. It would be appreciated that the camera frames reading scheme described above in reference to collimator 500 can be different:

1. The reading of the frame does not have to be at the instant that tab 514 interrupts photo sensor 516. This can be done at any phase of collimator 500 rotation as long as it is done at the same phase for every EC.
2. Reading more than one frame during one EC. It is desired however, that for each EC, an integer number of frames is read. By doing so, the read frames include the complete data of one EC which makes it easier to build one display-frame that can be presented on monitor 118 in few ways:
   a. Reference is made to FIG. 28A. In step 2800 a new EC begins.

Figure 28B:
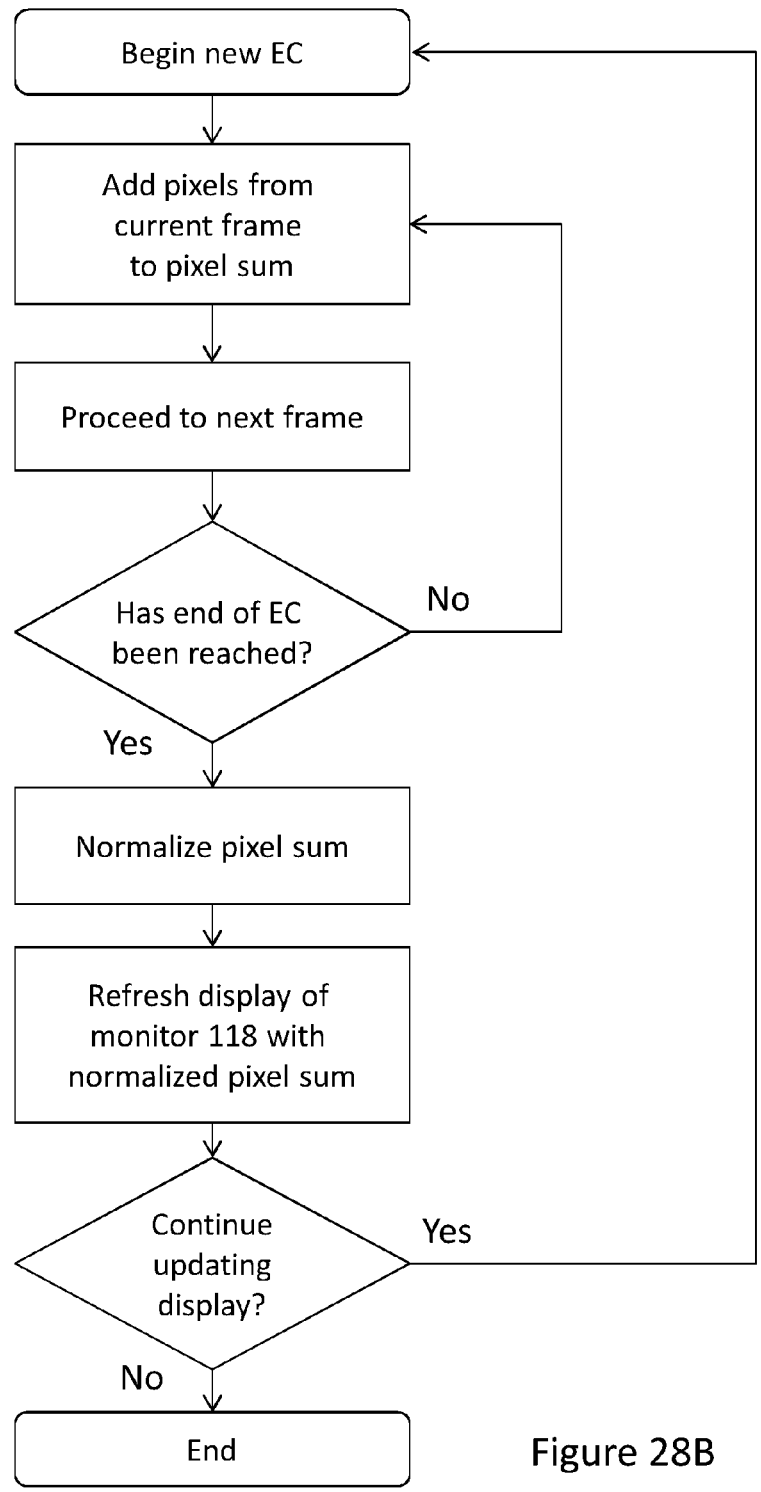
FIG. 28B is a flowchart describing a method for displaying the complete data from one EC using multiple frames, performing normalization after the frames have been summed.
Figure 28C:
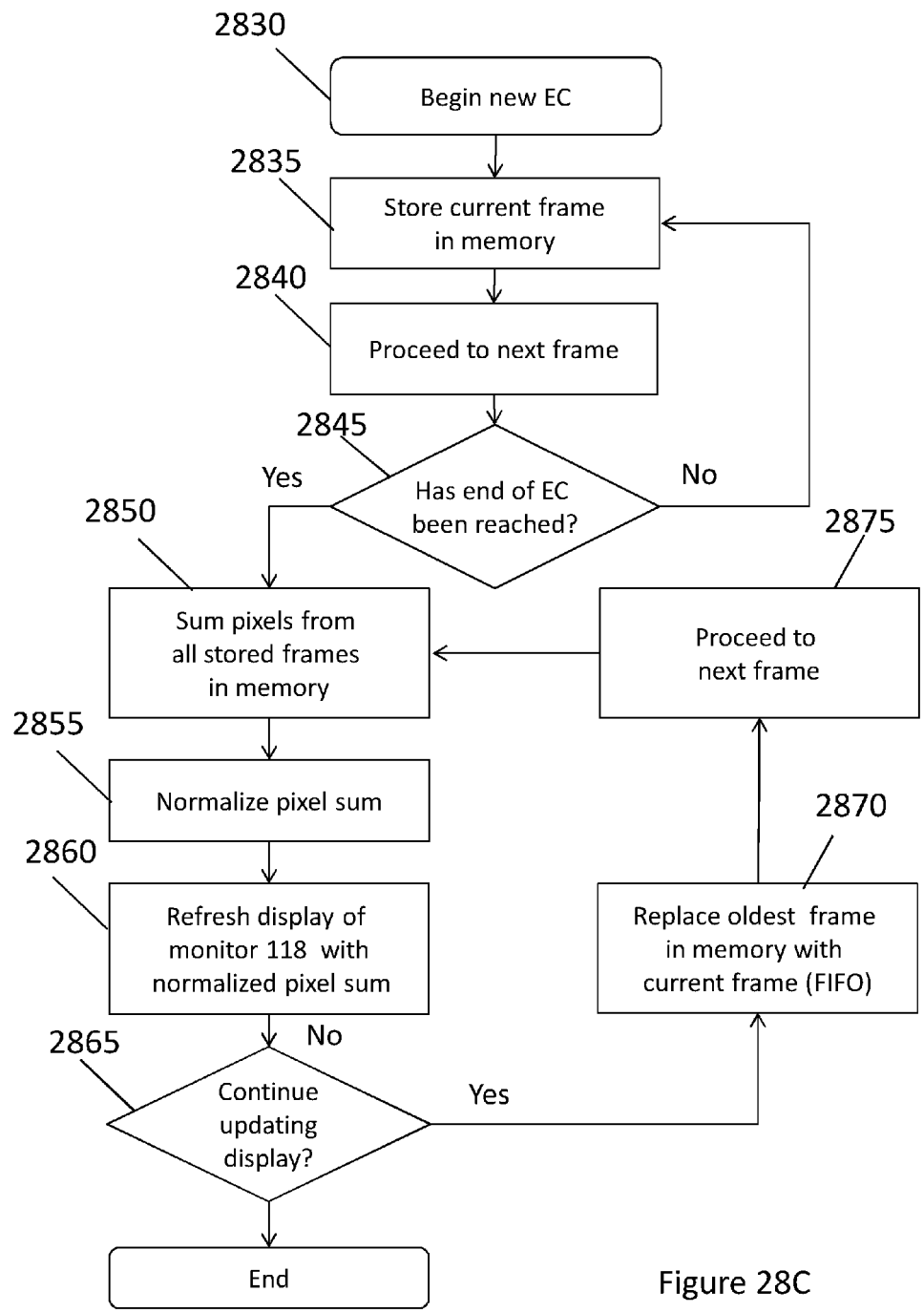
FIG. 28C is a flowchart describing a method for displaying the complete data from one EC using multiple frames, updating the display after every frame.

In step 2805 pixels from the current frame are normalized and added to the pixels sum (step 2810). In step 2815 next frame is considered. If the end of the EC has been reached, the displayed image is refreshed (step 2825) and the process returns to the beginning of a new EC. This process sums up the pixel values of all the frames of one EC to generate one complete exposure image. Then sums up the pixel values of all the frames of the next EC to generate next complete exposure image. This way, the picture on the monitor is replaced by a temporally successive image each time an EC is completed. Normalization of pixel values can be made for each frame separately or once only for the sum of the frames, as shown in FIG. 28B, or any other combination of frames.

b. Reference is made to FIG. 28C. For the example of this method we shall assume that the camera provides 8 frames during one EC. In step 2830 a new EC begins. In this example, all 8 frames numbered 1 to 8 are stored in frames storage (steps 2835-2845 and a first display-frame is generated from these frames as described above (summing the frames in step 2850 and normalizing pixel values in step 2855). The resultant image is then displayed on monitor 118. When frame 9 is acquired (after 1/8 EC), frame 1 is replaced by frame 9 in the frames storage (step 2870) and frames 9,2,3,4,5,6,7,8 are processed (summing, normalizing) to generate the second display-frame that can now be displayed on monitor 118 after 1/8 EC. After another 1/8 of an EC the next frame (frame 10) is acquired in step 2875 and stored in position of frame 2. Frames 9,10,3,4,5,6,7,8 are now processed to generate the third display-frame. This way, using a frames storage managed in the method of FIFO (first in first out) and generating display-frames with each new frame acquired from the sensor, a sequence of cine images are displayed for the user on monitor 118.

c. In another embodiment of the invention, summing the pixels of frames is made only for pixels that have been exposed to x-ray according to the criteria of collimator shape and motion during the integration time of the acquired frame. In example b above this would be 1/8 of the EC time. The pixels to be summed to create the image are (1) those from area 700 and (2) those in a sector of angle in the order of 2× (the angular span 508 of the collimator sector 506). The reason for 2× is that during 1/8 of the integration time the collimator rotates 1/8 of EC. A sector angle somewhat larger than 2• (angle 508) might be desired to compensate for accuracy limitations. This summing method reduces considerably the amount of pixels involved in the summing process and thus reduces calculation time and computing resources.

d. In another embodiment of the invention, the pixel processing is limited to those pixels specified in c above. This processing method reduces considerably the amount of pixels involved in the processing and thus reduces calculation time and computing resources.

e. In another embodiment of the invention, the storing of pixels is limited to those pixels specified in c above. This storing method reduces considerably the amount of pixels involved in the storage and thus reduces storage needs.

f. In another embodiment of the invention, any of the methods described in this section (a—as a general concept, b—as a specific example of a, c, d and e) can be combined to an implementation that uses any combination of the methods or few of them.

3. Reading one frame during more than one EC. In yet another embodiment, the collimator can be operated to provide an integer number of EC per one frame received from the sensor. For example, after 2 EC made by the collimator, one frame is read from the sensor. After normalizing pixel values of this frame, it can be displayed on monitor 118.

It would be appreciated that in many designs the frame rate provided from the sensor is dictated by the sensor and associated electronics and firmware. In such cases the speed of rotation of collimator 500 can be adjusted to the sensor characteristics so that one EC time is the same as the time of receiving an integer number of frames from the sensor (one frame or more). It is also possible to set the rotation speed of the collimator so that an integer number of EC is completed during the time cycle for acquiring on frame from the sensor.

The description of frames reading above is particularly adequate to CCD like sensors, whether CCD cameras mounted on image intensifier or flat panel sensors used instead of image intensifiers and cameras and located generally at plane 112 of FIG. 3. The specific feature of CCD is capturing the values of the complete frame, all the pixels of the sensor, at once. This is followed by sequential transfer of the analog values to an analog to digital convertor (A/D). Other sensors such as CMOS imaging sensors read the frame pixels typically one by one in what is known as a rolling shutter method. The methods of reading the sensor frames in synchronization with the collimator EC is applicable to such sensors as well regardless of the frames reading methods. The "random access" capability to read pixels of sensors such as CMOS sensors provides for yet another embodiment of the present invention. Unlike a CCD sensor, the order of reading pixels from a CMOS sensor can be any order as desired by the designer of the system. The following embodiment uses this capability. In this context, CMOS sensor represents any sensor that supports pixel reading in any order.

Figure 8:
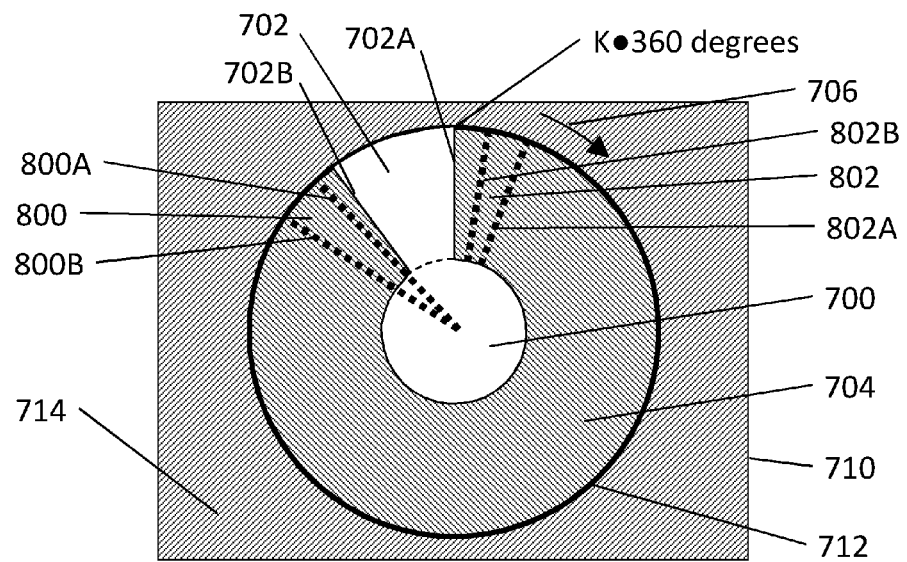
FIG. 8 is a schematic illustration of an example of reading process of pixel values of the sensor.
Figure 29:
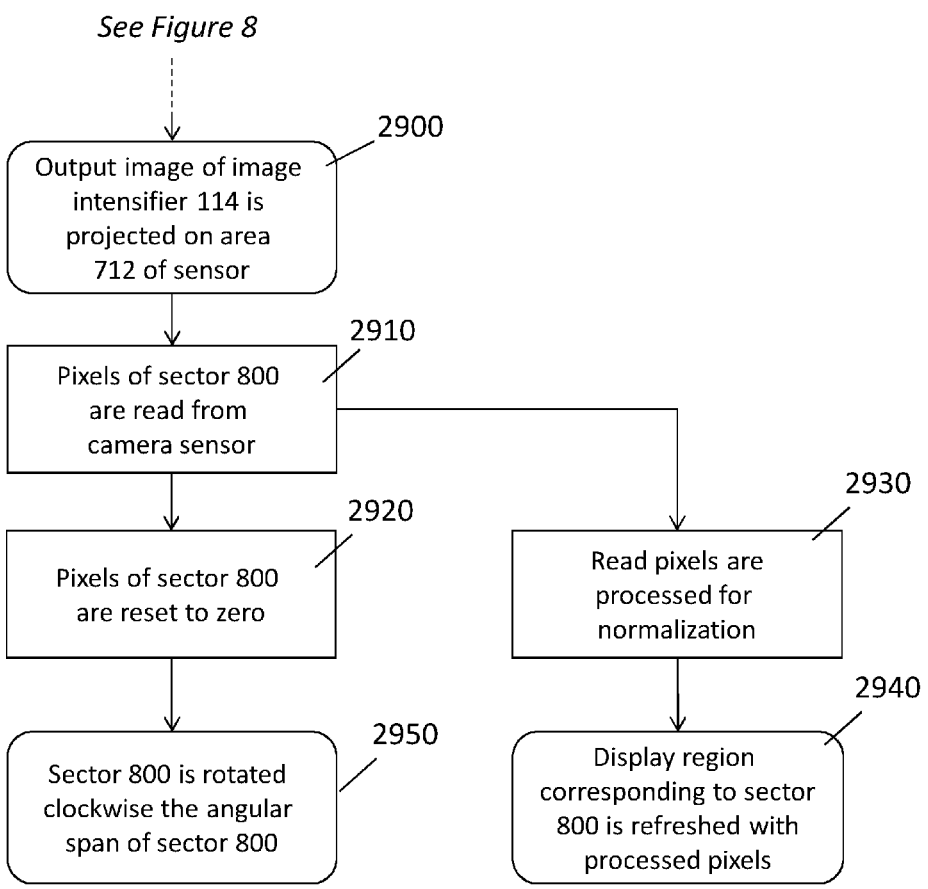
FIG. 29 is a flowchart referencing FIG. 8, describing the process of reading pixel values of the sensor.

Reference is made now to FIGS. 8 and 29. The embodiment of FIG. 8 is also described using an example of image intensifier and a CMOS camera but it would be appreciated that the method of this embodiment is applicable also to flat panel sensors and other sensors capable of random access for pixel reading.

In step 2900 the output image of image intensifier 114 is projected on area 712 of sensor 710. In accordance to the momentary position of rotating collimator 500, circle 700 and sector 702 are momentary illuminated in conjunction with collimator 500 position and sector 704 and sector 714 are not illuminated. Sectors 702 and 704 rotate as shown by arrow 706 in conjunction with the rotation of collimator 500.

For the purpose of this example, pixels before a radial line such as 702A or 800A are pixels which their centers are on the radial line or in direction clockwise from the radial line. Pixels that are after the radial line are pixels with centers that are in direction anticlockwise from the radial line. Sector 702 for example includes pixels that are after radial line 702A and also before radial line 702B. For example, in an embodiment mode where frame is read from the sensor once in an EC, the pixels adjacent to radial line 702A have just started to be exposed to the output image of the image intensifier and pixels adjacent to radial line 702B have just completed to be exposed to the output image of the image intensifier. Pixels in sector 702 are partially exposed per their location between 702A and 702B. In this example, the pixels in sector between radial lines 702B and 800B has not been read yet after being exposed to the image intensifier output.

In the current example of this embodiment, the instant angular position of radial line 702A is K•360 degrees (K times 360, K is an integer indicating the number of EC from the beginning of rotation). Angular span of section 702 is 36 degrees per the example of collimator 500. Therefore radial line 702B is at angle K•360−36 degrees. At this position of the collimator, a reading cycle of the pixels of sector 800 starts (step 2910). Radial line 800A is defined to ensure that all pixels after this radial line have been fully exposed. This angle can be determined using R1 of FIG. 5 and the pixel size projected on FIG. 5. To calculate a theoretical minimum angular gap between 702B and 800A to ensure that also the pixels adjacent to 800A have been fully exposed one should consider an arch of radius R1 in the length that has a chord of ½ pixel diagonal in length. This determines the minimum angular span between 702B and 800A to ensure full exposure to all the pixels in sector 800. In a more practical implementation, assuming that area 712 is about 1,000 pixels vertically and 1,000 pixels horizontally, and that R1 is in the order of ¼÷½ of R2 (see FIG. 4) and considering tolerances of such designs and implementation, a useful arch length of radius R1 would be, for example, the length of 5 pixels diagonal. This means the angular span between 702B and 800A is about 2.5 degrees. That is, at the instant of FIG. 8 the angular position of radial line 800A is K•360−(36+2.5) degrees.

In this specific example of the present embodiment, the angular span of sector 800 is also selected to be 36 degrees. Therefore, at the instant of FIG. 8 the angular position of radial line 800B is K•360−(36+2.5+36) degrees.

In FIG. 8 the angular span of sector 800 is drawn to demonstrate a smaller angle then the angular span of sector 702 to emphasize that the angles need not to be the same and they are the same in the example provided here in the text just for the purpose of the specific example of the embodiment.

Having determined the geometry of sector 800, the pixels of that sector are read now from the camera sensor. In a typical CMOS sensor the reading of each pixel is followed by a reset to that pixel (step 2920) so that the pixel can start integration signal from zero again. In another embodiment, in a first phase all the pixels of sector 800 are readout and in a second phase the pixels are reset. The reading and reset cycle of sector 800 has to be finished within the time it takes to sector 702 rotate an angular distance equal to the angular span of sector 800 (step 2950) to enable the system to be ready on time to read the next sector of the same angular span as sector 800 but is rotated clockwise the amount of angular span of sector 800 relative to the angular position of sector 800. In this example: 36 degrees.

In the above example, with collimator 500 rotating at 10 rps, sector 800 of 36 degrees span assumes 10 orientations through one EC, the orientations are 36 degrees apart and pixel reading and resetting cycles are made at a rate of 10 cps (cycles per second).

It would be appreciated that this embodiment can be implemented in different specific designs.

For example, the angular span of sector 800 might be designed to 18 degrees while that of sector 702 is still 36 degrees and collimator 500 is rotating at 10 rps.

In this example, sector 800 assumes 20 orientations through one EC, the orientations are 18 degrees apart and pixel reading and resetting cycles are made at a rate of 20 cps (cycles per second).

In yet another embodiment, the dark noise accumulated by the pixels in sector 704 that are after radial line 800B and before radial line 802A is removed by another reset cycle of the pixels located in sector 802 (after radial line 802A and before radial line 802B). This reset process is ideally made in a sector 802 specified near and before sector 702. The reset of all pixels of sector 802 has to be completed before radial line 702A of rotating sector 702 reaches pixels of sector 802. Otherwise, the angular span and angular position of reset sector 802 are designed in methods and considerations analog to those used to determine sector 800.

Pixels read from sector 800 should be processed for normalization (step 2930) and can be used to generate display-frames (step 2940) in ways similar to those described in section 2 above "Reading more than one frame during one EC" Where the current embodiment only the sector pixels are read, stored and processed and not the complete sensor frame.

In this embodiment, after pixel normalization of the last sector read, the processed pixels can be used to replace directly the corresponding pixels in the display-frame. This way the display-frame is refreshed in a mode similar to a radar beam sweep, each time the next sector of the image is refreshed. Following 360/(angular span of the readout sector) refreshments, the entire display-frame is refreshed. This provides a simple image refreshment scheme.

Figure 9:
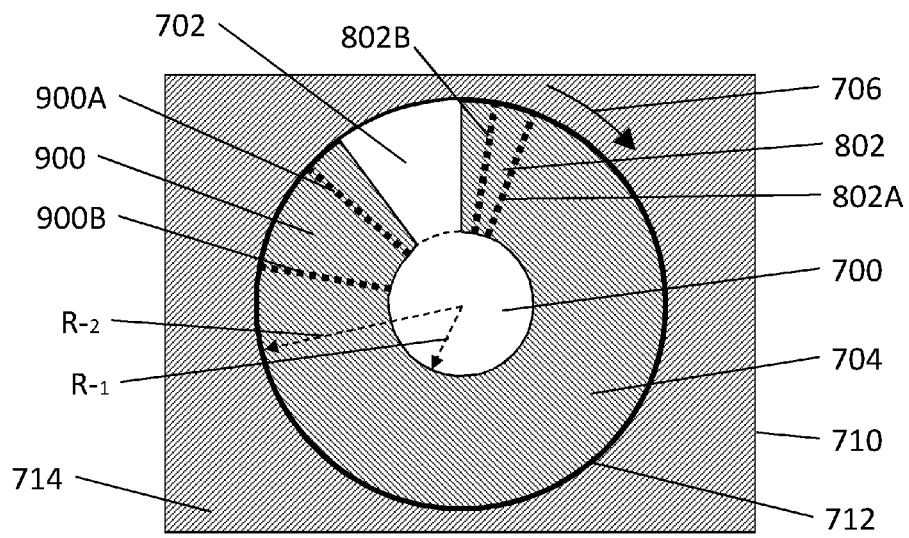
FIG. 9 is a schematic illustration of an example of reading process of pixel values of the sensor.

Attention is made now to FIG. 9. Unlike FIG. 8 where the reading sector included the complete set of pixels located after radial line 800A and before radial line 800B, in the present invention the reading area geometry is divided to two parts: circular area 700 and sector 900. Sector 900 of the embodiment of FIG. 9 contains the pixels that are after radial line 900A and are also before radial line 900B and are also located after radiuses R–1 and before R–2. In this example pixels before a radius are those with distance from the center smaller or equal to radius R and pixels after a radius R are those with distance from the center larger then R. The pixels of area 700 are all those pixels located before R–1.

In this embodiment, the pixels of section 900 are read and handled in using the same methods described in reference to the embodiment of FIG. 8. The same holds also for reset sector 802.

The pixels of area 700 are handled differently.

In one implementation of the current embodiment, The pixels in area 700 can be read once or more during one EC and handled as described above for the embodiment of reading the entire CMOS sensor or area 700 can be read once in more then one EC and handled accordingly as described above for the embodiment of reading the entire CMOS sensor.

It would be appreciated that for each reading method the normalization process of the pixels must be executed to get a display-frame where all the pixels values represents same sensitivity to exposure.

Attention is made now to FIG. 10 that provides one example for the design of a collimator of the present invention combined with a motion system aimed to provide the rotation function of collimator 500.

Figure 10A:
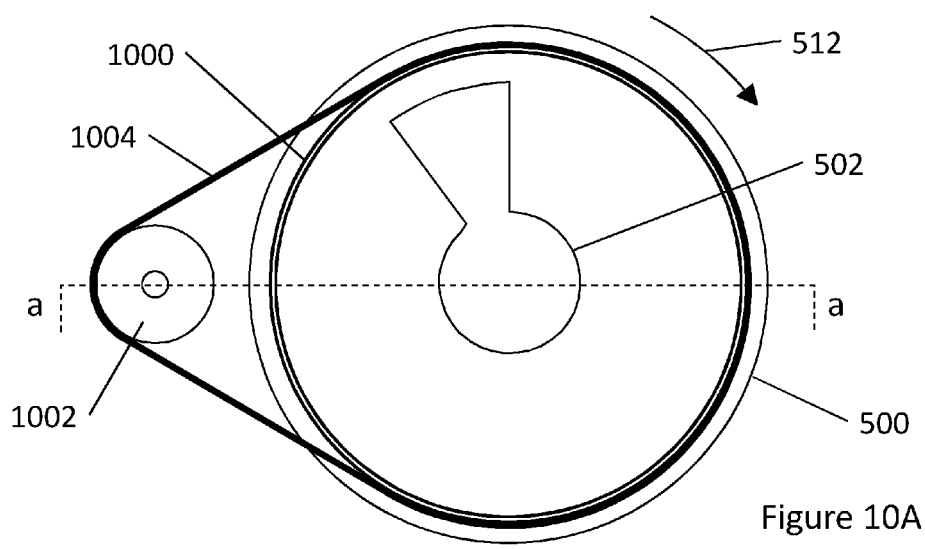
FIG. 10A is a schematic illustration of a top view of an example of a collimator of the invention.

FIG. 10A is a top view of the collimator and the rotation system of this example.

Figure 10B:
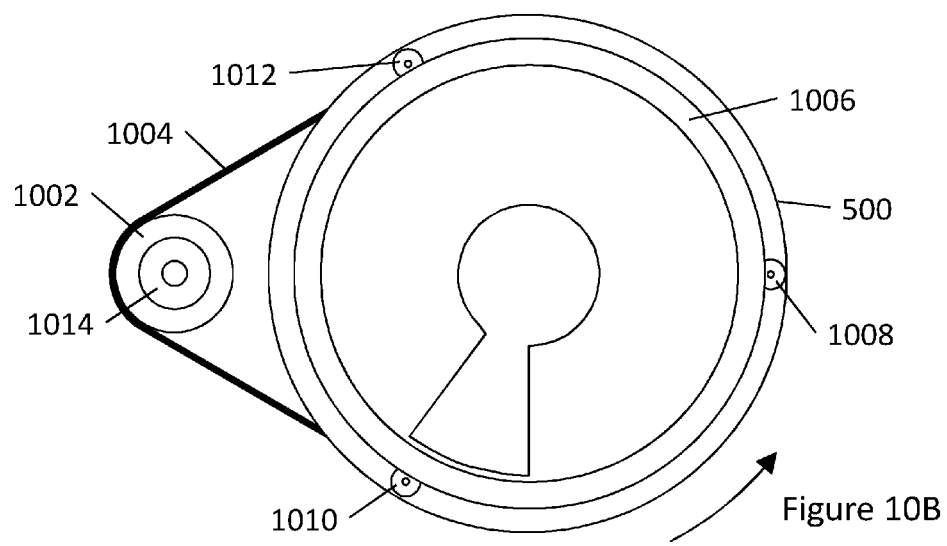
FIG. 10B is a schematic illustration of a bottom view of the example collimator of FIG. 10A.

FIG. 10B is a bottom view of the collimator and the rotation system of this example.

Figure 10C:
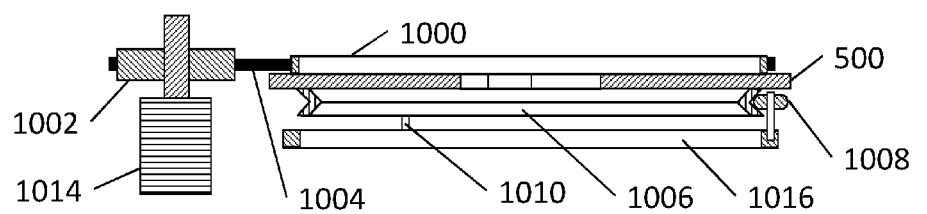
FIG. 10C is a schematic illustration of a cross-section view of the example collimator of FIG. 10A.

FIG. 10C is a view of cross-section a-a of FIG. 10A.

FIG. 10A is showing collimator 500 and aperture 502 (other details are removed for clarity). Pulley 1000 is mounted on top of collimator 500 in a concentric location to the collimator. Pulley 1002 is mounted on motor 1012 (see motor in FIG. 10B and FIG. 10C). Belt 1004 connects pulley 1000 with pulley 1002 to transfer the rotation of pulley 1002 to pulley 1000 and thus to provide the desired rotation of collimator 500. The belt and pulley system example 1000, 1002 and 1004 presents a flat belt system but it would be appreciated that any other belt system can be used including round belts, V-belts, multi-groove belts, ribbed belt, film belts and timing belts systems. FIG. 10B showing the bottom side of FIG. 10A displays more components not shown before. V-shape circular track 1006 concentric with collimator 500 is shown (see a-a cross section of 1006 in FIG. 10C). Three wheels 1008, 1010 and 1012 are in contact with the V-groove of track 1006. The rotation axes of the 3 wheels are mounted on an annulus shaped static part 1016 (not shown in FIG. 10B) that is fixed to the reference frame of the x-ray tube. This structure provides a support of collimator 500 in a desired position in reference to the x-ray tube (for example the position of collimator 104 of FIG. 3) while, at the same time provides 3 wheels 1008, 1010 and 1012 with track 1006 for collimator 500 to rotate as desired.

The rotation of motor 1014 is transferred to collimator 500 by pulley 1002, through belt 1004 and pulley 1006. Collimator 500 then rotates being supported by track 1006 that slides on wheels 1008, 1010 and 1022.

It would be appreciated that the rotation mechanism described here is just one example for a possible implementation of rotation mechanism for a rotating collimator. Rotation mechanism might instead use gear transmission of any kind including spur, helical, bevel, hypoid, crown and worm gears. The rotation mechanism can use for 1002 a high friction surface cylinder and bring 1002 in direct contact with the rim of collimator 500 so that belt 1004 and pulley 1000 are not required. Another implementation may configure collimator 500 as also a rotor of a motor with the addition of a stator built around it.

In the description of the collimator of FIG. 5, tab 514 and photo sensor 516 were presented as elements providing tracing of the angular position of collimator 500 for the purpose of synchronization between the collimator angular position and the sensor reading process. These elements were presented as one implementation example. The embodiment means for tracing the rotational position can be implemented in many other ways. In the example of FIG. 10, motor 1002 might have a attached encoder such as available from Maxon Precision Motors, Inc, Fall River, Mass., USA. Simple encoder can be constructed by taping a black and white binary coded strip to the circumference of collimator 500 and reading the strip using optical sensors such as TCRT5000 Reflective Optical sensor available from Newark, http://www.newark.com.

Collimator 500 was described hereinabove as having a fixed aperture that cannot be modified after manufacturing of the collimator.

It would be appreciated that in other embodiment of the inventions, mechanical designs of collimator assemblies can be made to accommodate exchangeable collimators. This way, different apertures can be mounted to the collimator assembly per the needs of the specific application.

In additional implementation example of the invention, the collimator can be designed to have a variable aperture within the collimator assembly. This is demonstrated in reference to FIG. 11.

Figure 11A:
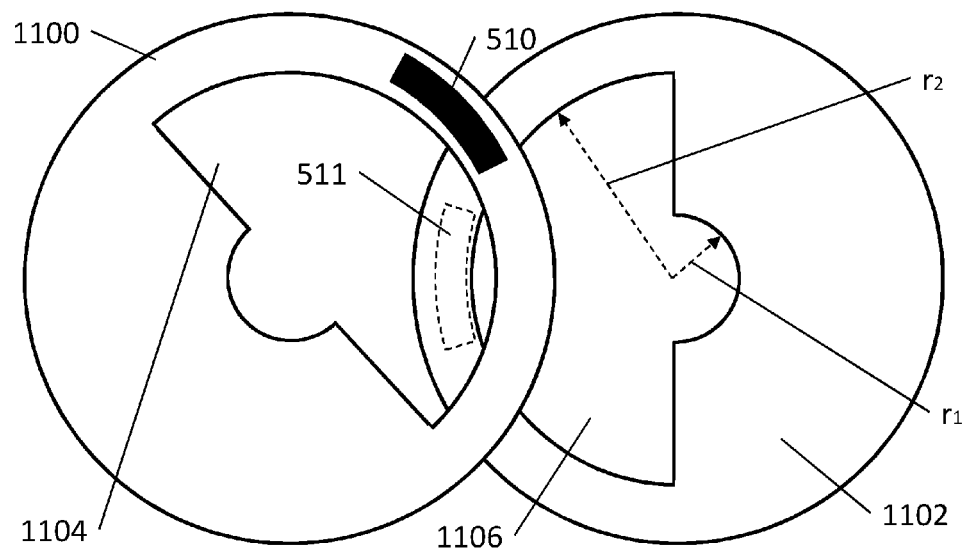
FIG. 11A is a schematic illustration of the main parts of another example of a collimator of the invention.

The collimator of FIG. 11 is constricted from two superimposed collimators shown in FIG. 11A. One collimator is 1100 with aperture 1104 and balancing weight 510 to bring the center of gravity of this collimator to the center of rotation of this collimator. The second collimator is 1102 with aperture 1105 and balancing weight 511 to bring the center of gravity of this collimator to the center of rotation of this collimator. In both collimators the aperture geometry is the combination of central circular hole of radius r1 and sector hole of radius r2 and sector angular span of 180 degrees. Actually, collimator 1102 is of the same general design as collimator 1100 and it is flipped upside down.

Figure 11B:
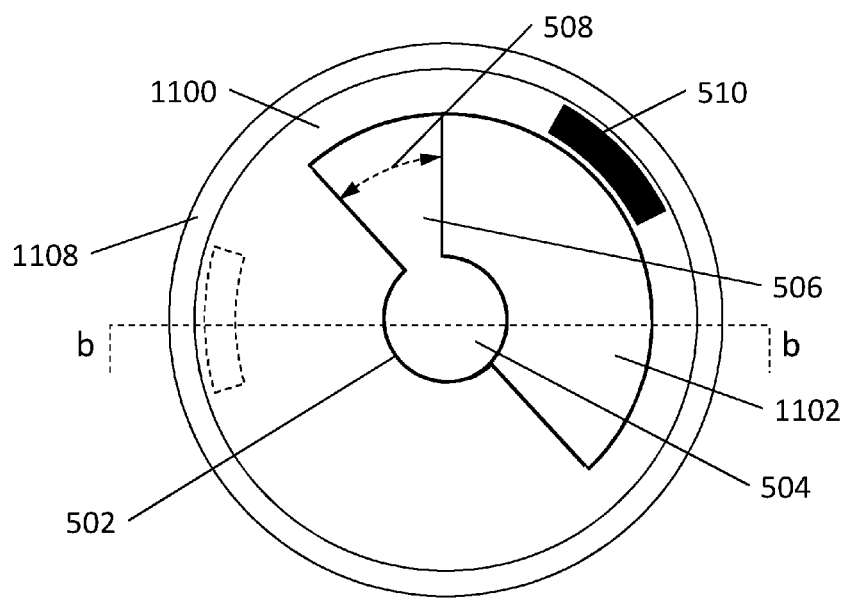
FIG. 11B is a schematic illustration of the parts of FIG. 11A in the operative configuration.
Figure 11C:
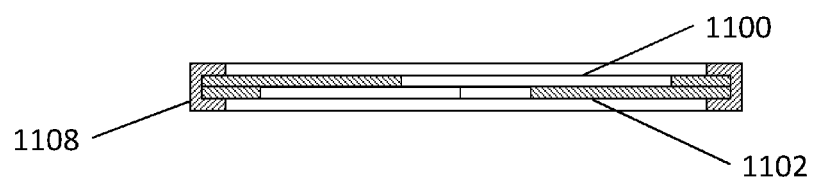
FIG. 11C is a schematic illustration of a cross section of FIG. 11B.
Figure 11D:
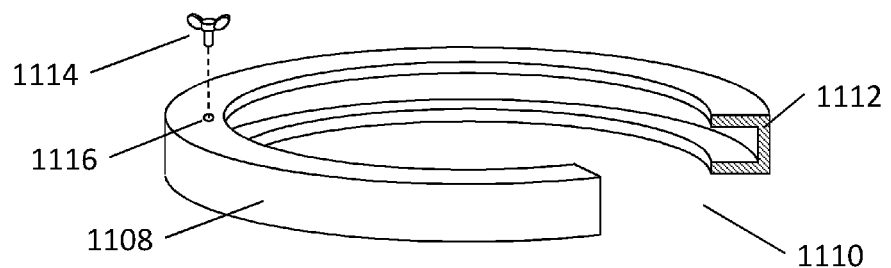
FIG. 11D is a schematic illustration of parts of the collimator example of FIG. 11B.

When collimators 110 and 1102 are placed concentric one on top of the other as shown in FIG. 11B we get a combined aperture which is the same as that in collimator 500 of FIG. 5. By rotating collimator 1100 relative to collimator 1102, the angular span of sector 508 can be increased or decreased. In this example the angular span of sector 508 can be set in the range of 0÷180 degrees. In this example, ring 1108 holds collimators 1100 and 1102 together as shown also in FIG. 11C which is cross-section b-b of FIG. 11B. Reference is made to FIG. 11C now (weights 510 and 511 are not shown in this cross-section drawing). In this example of the invention, ring 1108 is shown holding together collimators 1100 and 1102, allowing them to be rotated one relative to the other to set the angular span 508 of sector 506 as desired. An example for a locking mechanism to hold collimators 1100 and 1102 is the relative desired orientation is described in FIG. 11D. In FIG. 11D ring 1108 is shown without collimators 1100 and 1102 for clarity. A section 1110 is cut-out in the drawing to expose the u-shape 1112 of ring 1108, inside which collimators 1100 and 1102 are held. Screw 1114 that fits into threaded hole 1116 is used to lock collimators 1100 and 1102 in position after the desired angular span 508 has been set. To change angular span 508 the operator can release screw 1114, re-adjust the orientation of collimators 1100 and/or 1102 and fasten screw 1114 again to set the collimators position. The example of FIG. 11, including the manual adjustment of angular span 508 is provided as one example of implementation of the invention. Many other options are available. One more example is shown in reference to FIG. 12. In this example, angular span 508 can be controlled by a computer. The mechanism of FIG. 12 is manly a structure containing two units similar to the unit of FIG. 10 with few changes including the removal of pulley 1000 using instead the rim of the collimator as a pulley. Balance weights 510 and 511 are not shown here for clarification of the drawing.

Figure 12A:
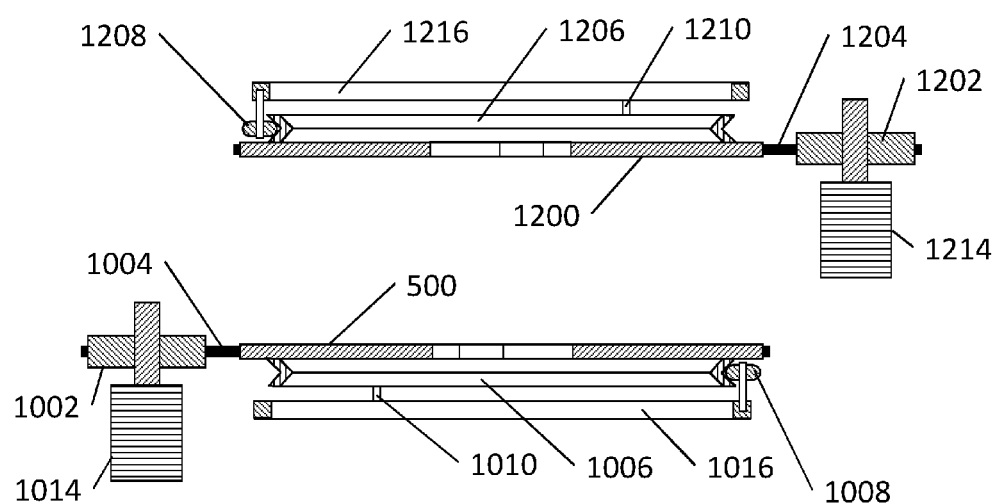
FIG. 12A is a schematic illustration of the main modules of another example of a collimator of the invention.
Figure 12B:
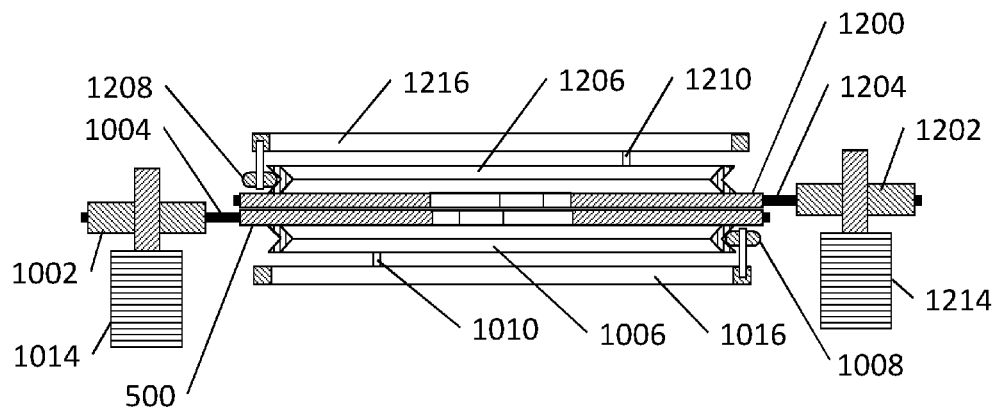
FIG. 12B is a schematic illustration of the modules of FIG. 12A in the operative configuration.

In FIG. 12A, the bottom unit that includes collimator 500 is essentially the assembly of FIG. 10 with pulley 1000 removed and using instead the rim of the collimator 500 as a pulley. In the top unit that includes collimator 1200, the assembly is same as the bottom assembly when the bottom assembly is rotated 180 degrees about an axis vertical to the page with the exception that motor 1214 was rotated another 180 degrees so that it is below the pulley, same as motor 1014. This is not a compulsory of this example but in some design cases it might help to keep the space above the assembly of FIG. 12 clear of unwanted objects. FIG. 12B is showing now these 2 assemblies brought together so that collimators 500 and 1200 are near each other and concentric. In the assembly of FIG. 12B each of the collimators 500 and 1200 can be rotated independently. For each collimator the angular position is known through any encoding system, including the examples provided above. In one example of usage of the assembly of FIG. 12B, angular span 508 is set when collimator 500 is at rest and collimator 1200 is rotated until the desired angle 508 is reached. Then both collimators are rotated at the same speed to provide the x-ray exposure pattern examples as described above. It would be appreciated that it is not required to stop any of the collimators to adjust angle 508. Instead, during the rotation of both collimators, the rotation speed of one collimator relative to the other can be changed until the desired angle 508 is achieved and then continue rotation of both collimators at the same speed.

It would be appreciated that a mechanism with capabilities such as the example of FIG. 12B can be used to introduce more sophisticated exposure patterns. With such mechanisms angle 508 can be changed during an EC to generate multiple exposure patterns. For example angle 508 may be increased for the first half of the EC and decreased for the second half of the EC. This creates an exposure pattern of 3 different exposures (it is appreciated that the borders between the areas exposed through sector 506 is not sharp and the width of these borders depend on angle 508 and the speed of changing this angle relative to the speed of rotation of the collimators.

It would also be appreciated that any of the collimators of the invention can be rotated at a variable speed through the EC and affect the geometry of exposure. For example, collimator 500 of FIG. 5 can rotate at one speed over the first 180 degrees of the EC and twice as fast during the other 180 degrees of the EC. In this example the area exposed through sector 506 during the first half of the EC has twice the DPP than the area exposed through sector 506 during the second half of the EC, with gradual DPP change over the boundary between these two halves. The central area exposed through circular aperture 504 has a $3^{rd}$ level of DPP. Other rotation speed profiles can generate other exposure geometries. For example 3 different rotation speeds over 3 different parts of the EC will generate 4 areas with different DPP.

The examples provided above presented collimators with apertures having similar basic shapes consisting of central round opening combined with a sector-shaped opening. These examples were used to present many aspects of the invention but the invention is not limited to these examples.

Figure 13A:
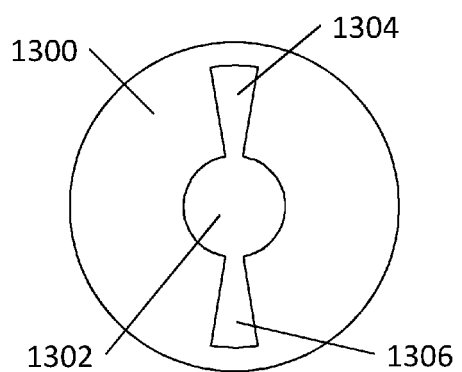
FIG. 13A is a schematic illustration of another example of a collimator of the invention.

Reference is made now to FIG. 13A showing another example of an aperture of the invention. In this example the aperture of collimator 1300 is constructed of a circular hole 1302 concentric with the collimator rim, a sector-shaped hole 1304 and a sector shaped hole 1306 in opposite direction to 1304 (the two sectors are 180 degrees apart). If it is desired, for example that annulus area of FIG. 6 (that includes sectors 602 and 604) will be exposed to DPP that is 1/10 than the DPP of area 600 of FIG. 6 then each of the sectors 1304 and 1306 can be set to 18 degrees and then one EC can be achieved with only 180 degrees rotation of collimator 1300 comparing to 360 degrees required for the collimator of FIG. 5. Also, for 10 fps the rotation speed of collimator 1300 should be 5 rps and not 10 rps as in the case of collimator 500 of FIG. 5. Furthermore, balance weight such as 510 of FIG. 5 is not required for collimator 1300 of FIG. 13A since it is balanced by its' geometry.

Figure 13B:
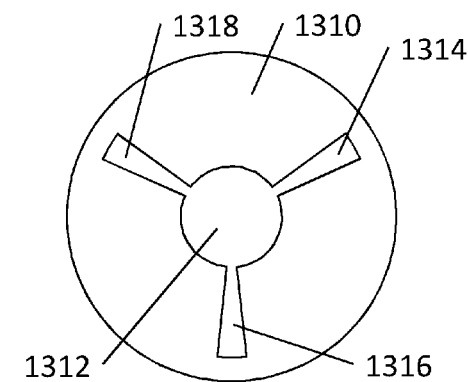
FIG. 13B is a schematic illustration of another example of a collimator of the invention.

Another example of a collimator according to the invention is provided in FIG. 13B. The aperture of collimator 1310 is constructed of a circular hole 1312 concentric with the collimator rim, a sector-shaped hole 1314, a sector-shaped hole 1316 and a sector shaped hole 1318 the three sectors are 120 degrees apart. If it is desired, for example that annulus area of FIG. 6 (that includes sectors 602 and 604) will be exposed to DPP that is 1/10 than the DPP of area 600 of FIG. 6 then each of the sectors 1314, 1316 and 1318 can be set to 12 degrees and then one EC can be achieved with only 120 degrees rotation of collimator 1310 comparing to 360 degrees required for the collimator of FIG. 5. Also, for 10 fps the rotation speed of collimator 1300 should be 10/3 rps and not 10 rps as in the case of collimator 500 of FIG. 5. Furthermore, balance weight such as 510 of FIG. 5 is not required for collimator 1310 of FIG. 13B since it is balanced by its' geometry.

It would be appreciated that relations and methods for rotating the collimator examples of FIG. 13A and FIG. 13B and reading pixel values from the image sensor described above in relation to the collimator example of FIG. 5 are fully implantable with the examples of the collimators of FIG. 13A and FIG. 13B with adjustments that are obvious for a person skilled in the art. For example, for the collimator of FIG. 13B and a CMOS camera pixel reading sector 800 of FIG. 8 can be complemented by additional 2 pixel reading sectors, each in conjunction to one of the 2 additional aperture sectors of FIG. 13B.

Some of these changes and comparison are indicated in the following table that presents an example of differences in features and implementation between the 3 different examples of collimators.

| Collimator | FIG. 5 | FIG. 13A | FIG. 13B | Comments |
|---|---|---|---|---|
| Central round aperture | Yes | Yes | Yes | |
| # of aperture sectors | 1 | 2 | 3 | |
| Sectors angular span | 36 deg | 18 deg | 12 deg | For 1:10 DPP ratio |
| Sectors angular separation | NA | 180 deg | 120 deg | |
| EC rotation | 360 deg | 180 deg | 120 deg | |
| rps | 10 | 5 | 10/3 | For 10 fps |
| fps at 10 rps | 10 | 20 | 30 | |

FIG. 11 and FIG. 12 provides an example on how collimator 500 of FIG. 5 can be contracted in a way that enables variable angle span 508 of sector 506.

FIG. 14 provides an example how the collimator of FIG. 13A can be constructed so that the angle span of sectors 1304 and 1306 can be adjusted as desired.

Figure 14A:
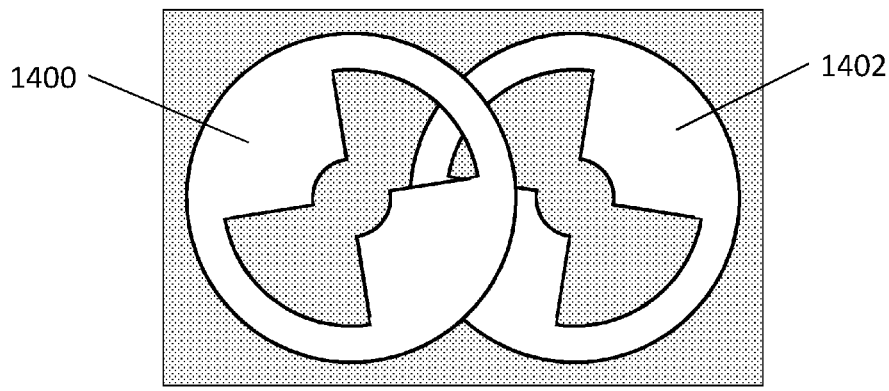
FIG. 14A is a schematic illustration of the main parts of another example of a collimator of the invention.
Figure 14B:
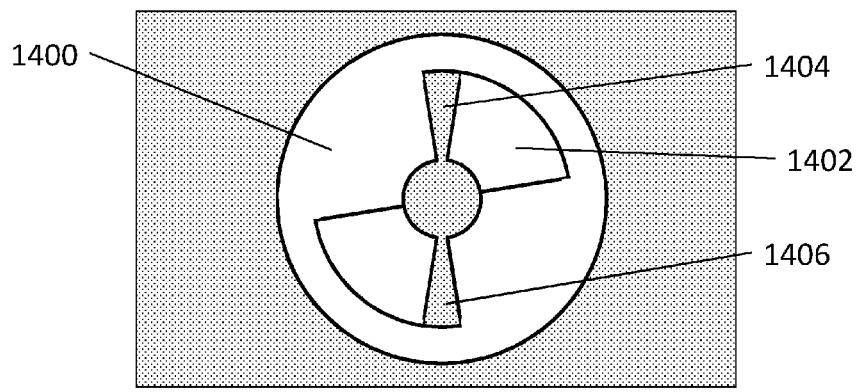
FIG. 14B is a schematic illustration of the parts of FIG. 14A in the operative configuration.

In FIG. 14A presents an example of 2 collimators 1400 and 1402. The gray background rectangle is provided for a better visualization of the collimators solid area and the aperture holes and they are not a part of the structure. Same is for FIG. 14B. Each of the collimators have an aperture made of a circular hole concentric with the collimator rim and two sectors holes, each sector has an angular span of 90 degrees and the sectors are 180 degrees apart. When collimators 1400 and 1402 are placed one on top of the other and concentric, the combined collimator of FIG. 14B is provided. The aperture size and shape of the collimator in FIG. 14B is the same as the size and shape of the aperture of the collimator of FIG. 13A. In the case of the assembly of FIG. 14B however, the angular span of aperture sectors 1404 and 1406 can be modified by rerating collimators 1400 and 1402 relative to each other. This can be done using any of the methods described above in reference to FIG. 11 and FIG. 12.

It would be appreciated that similar designs can provide for variable angular span of the aperture sectors of collimator 1310 of FIG. 13B and other aperture designs.

In the aperture design above, the aperture shape was designed to provide, at a constant rotation speed two areas with two different DPP.

Figure 15A:
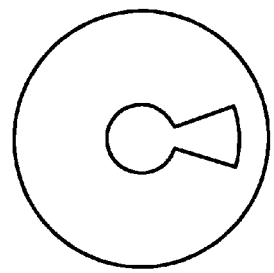
FIG. 15 is a schematic illustration of another 4 example of another collimator of the invention and a qualitative exposure generated by the collimator as a distance from the center of rotation.
Figure 15A:
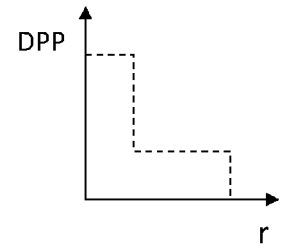
Figure 15B:
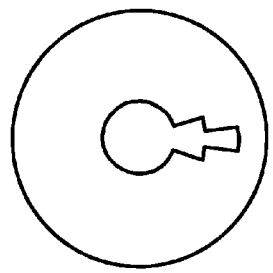
Figure 15B:
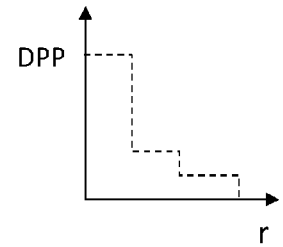
Figure 15C:
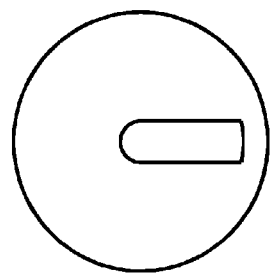
Figure 15C:
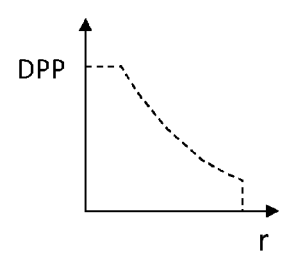
Figure 15D:
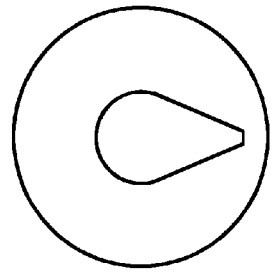
Figure 15D:
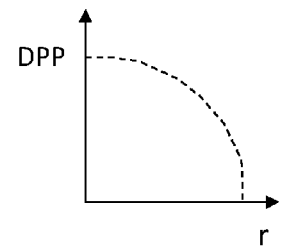

FIG. 15A represents such a collimator and also a qualitative exposure profile showing two levels of DPP for different distances from the center –r. Other apertures can be designed to provide any desired exposure profiles. Some examples are shown in FIG. 15B, FIG. 15C and FIG. 15D. All the collimators of FIG. 15 have aperture design aimed at rotation of 360 degrees for one EC.

Figure 16A:
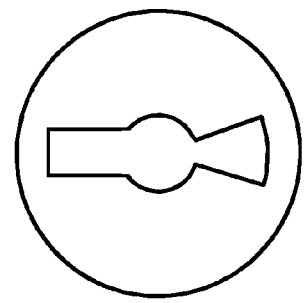
FIG. 16 is a schematic illustration of another 4 example of another collimator of the invention.
Figure 16B:
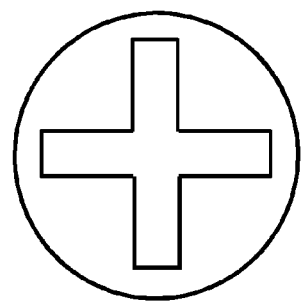
Figure 16C:
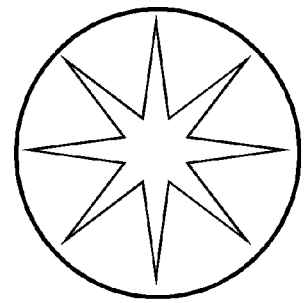
Figure 16D:
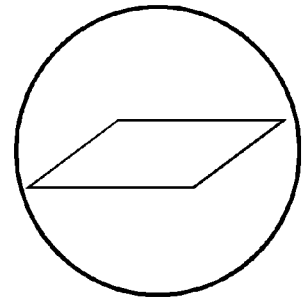

The features of the apertures in the collimators of FIG. 15 can be combined with the features of the apertures in the collimators of FIG. 13. Examples for such combinations are shown in FIG. 16 showing 4 collimators with 4 different aperture designs. In FIG. 16A the left and right halves of the aperture are not symmetrical and one EC requires 360 degrees rotation. FIG. 16B offers a collimator with an aperture providing an exposure profile similar (but not identical) to that of FIG. 15C but one EC consists of 90 degrees rotation only. FIG. 16C offers a collimator with an aperture providing an exposure profile similar (but not identical) to that of FIG. 15D but one EC consists of 360/8=45 degrees rotation only. FIG. 16D offers a collimator with an aperture providing an exposure profile similar (but not identical) to that of FIG. 15D also but one EC consists of 180 degrees rotation only.

Following these examples it is appreciated the invention may be implemented in many designs and it is not limited to a particular design provided hereinabove as an example.

Pixel Correction:

As explained above, pixels with different DPP per the collimator design and use are normalized to provide a proper display-frame. Normalization scheme is made in accordance to the x-ray exposure scheme (i.e., collimator shape, speed and position). Such normalization can be done on the basis of theoretical parameters. For example, in reference to FIG. 7 and FIG. 5, with collimator 500 rotating as a constant speed, the pixels of the annulus incorporating sectors 702 and 704 receive 1/10 the dose of circular area 700 (in this example the angular span 508 of sector 506 is 36 degrees). For simplicity of this example it is assumed that one frame is read from the sensor every time an EC is completed (i.e., collimator 500 completes a rotation of 360 degrees). It is also assumed that all sensor pixels are of the same response to the image intensifier output and that the image intensifier has uniform response and the x-ray beam from the x-ray tube is uniform. The only built-in (i.e. system level) source of differences between the pixels is from the collimator and the way it is operated. In this example the normalization based on the system design would be a multiplication of pixels by one or 2 factors that will compensate for the difference in DPP.

In one normalization example the values from the pixels of the annulus incorporating sectors 702 and 704 can be multiplied by 10. In another normalization example the values from the pixels of circular area 700 can be multiplied by 1/10. In yet another normalization example the values from the pixels of the annulus incorporating sectors 702 and 704 can be multiplied by 5 and the values from the pixels of circular area 700 can be multiplied by 1/2. It would be appreciated that description, explanations and examples of this invention, multiplication and division are completely equivalent and expressions like "multiplying by 1/10" is completely equivalent to expressions like "divide by 10" and whenever multiplication by a value is mentioned it means also the division by reciprocal value alternative and vise-versa. The same holds for multiplication and division symbols used in equations. For example A/B represents also A•C where C=1/B.

The example above is relatively simple since the normalization scheme incorporates 2 knows areas with two known DPP. The situation can become relatively more complicated with different collimators or collimator motion scheme.

In the following example a change is introduced to the rotation of collimator 500. Instead of constant rotation speed a variable rotation speed is used as presented in the following table for one EC (in the case of collimator 500: 360 degrees):

| Sector # | EC range (degrees) | Angular rotation status |
|---|---|---|
| 1 | 0-150 | Constant speed 1 |
| 2 | 150-180 | Constant positive acceleration |
| 3 | 180-330 | Constant speed 2 |
| 4 | 330-360 | Constant negative acceleration |

This rotation pattern together with the convolution with the image pixels, especially in the acceleration sectors, makes it more difficult to estimate normalization the factors.

In the example of the collimators of FIG. 15C and FIG. 15D, many "pixel rings" (pixels at a certain distance from the center) need a suitable normalization factor. Production tolerances of the system that are not included in the theoretical estimation of the normalization factors might result in errors that will show up as ring patterns in the image displayed on monitor 118.

The following calibration method provides calibration that removes the need for theoretical estimation of the factors and also compensates for production tolerances.

In this example any collimator of the invention can be used and any rotation pattern that is fixed per EC can be used.

The multiple frame x-ray imaging system is set to include all the fixed element relevant to the imaging process (x-ray tube, the desired x-ray operation mode i.e. voltage and current, possible x-ray filter, collimator, patient bed, image intensifier, camera) but none of the variable parts (the patient, the operator's hands and tools).

According to this calibration method, the desired collimator is rotated in the desired pattern. A set of raw frame is acquired (using any of the example methods mentioned above). A raw frame is a frame resulting from an integer number of one or more EC with all the pixels of are 712 (FIG. 7), without any manipulation of the pixels. The number of raw frames acquired should be enough to get a relatively good S/N on an average raw frame that is the average of the acquired raw frames. An average raw frame with S/N that is 10 times higher than that of the raw frame is typically sufficient and this can be achieved by averaging 100 raw frames. It would be appreciated that more or less raw frames can be used, depending on the desired quality of the normalized frame.

One average raw frame is created with x-ray off and another with x-ray on. For this example we assume that the brightness value for each pixel for display purpose ranges from zero to 255. We also select to display a theoretical noiseless frame in the range 5÷250 (darkest noiseless pixel is displayed at value 5 and the brightest exposed noiseless pixel is displayed at value 250. This enables noise that brings the pixel values to the range 0÷4 and 251÷255 contribute its statistics appearance to the displayed-frame). The correction for each pixel i of raw frames j, Pij (j is a frame number index in this example) is calculated using the values of the pixels of the average raw frame made with x-ray radiation on, Ai, and values of the pixels of the average raw frame made with x-ray radiation off, Bi, to produce the corrected pixel Dij as follows:

$$Dij=(Pij-Bi)•(245/Ai)+5 \quad \text{(Equation 1)}$$

In yet a somewhat more simple approach the correction might ignore noise visual aspects at the dark and bright level and simply correct to the display range 0÷255 as follows:

$$Dij=(Pij-Bi)•(255/Ai) \quad \text{(Equation 2)}$$

It would be appreciated that the correction suggested above is linear and works best for systems with relatively linear response of the image intensifier and the camera.

For systems with non linear response, more complicated correction schemes may be used such as bi-linear correction. In this example the range of the values of the pixels is divided roughly to 2 ranges. The current of the x-ray can be reduced, for example to ½ its' normal operation mode so that the DPP is reduced to ½. It is appreciated that the reduced current level depends on the nature of the non linearity and optimal bi-linear correction might require other than ½ of the x-ray current. It would also be appreciated that DPP can be reduced also in other ways such aluminum plates placed right after the collimator.

In this example, with ½ the x-ray current, another set of raw frames is acquired. It would be appreciated that the S/N of these raw frames is lower than that of the raw frames of the standard x-ray current for the specific application. This can be compensated by using more raw frames to generate the average raw frame for ½ the x-ray current, for example 200 raw frames. Let Mi represent the values of the pixels of the average raw frame made with ½ x-ray current radiation on The correction example of Equation 2 is implemented in this example as follows:

For Pij with values less or equal 127

$$Dij=(Pij-Bi)•(127/Mi) \quad \text{(Equation 3)}$$

For Pij with values higher than 127

$$Dij=(Pij-Bi)•(255/Ai) \quad \text{(Equation 4)}$$

It would be appreciated that the x-ray current for Mi might be set to a different level (for example ¼ of the standard current for the specific application) and the equations will assume the form:

For Pij with values less or equal 63

$$Dij=(Pij-Bi)•(63/Mi) \quad \text{(Equation 5)}$$

For Pij with values higher than 63

$$Dij=(Pij-Bi)•(255/Ai) \quad \text{(Equation 6)}$$

It would also be appreciated that if the non-linearity of the pixels is similar between the different pixels within the operating range of the system (that is differences in non linear response are relatively small) correction for non linearity, in most cases is not required. If the application does not require linear response and it is only desired to reduce pixels response non uniformity affects on the displayed frame, then one may skip non-linearity correction. All pixels corrections can be skipped if the noise pattern resulting from this does not disturb the application. The correction can be made at different sophistication levels (linear, bi-linear, tri-linear, polynomial interpolation and so on) or not at all, as suitable for the application.

Variable ROIs and variable rotation speed profiles:

In the above examples different rotation profiles with different rotation speeds were described. In the following example rotation profiles of variable speed will be described in the context of ROI in the image. In the examples of the collimators above, a central circular area (such as 600 of FIG. 6 and 700 of FIG. 7) was presented as the ROI and therefore receiving more DPP than the annulus of sectors 702 and 704 that receive lower DPP. This is the trivial case and typically the central area of the image is also the ROI, where the more important part of the image is located. The higher DPP results in higher S/N in this area and therefore provides a better image quality in that area (such as better distinguishable details). Normally, during, for example of a catheter insertion procedure, the patient's bed is moved during the process to keep the tip of the catheter in the range of area 700. Yet, sometimes the area of highest interest in the image moves out of area 700. For example, in reference to FIG. 17A, to the area denoted by numerical indicator 1700. This might be a result of many reasons such as (1) the catheter tip has moved to area 1700 and the patient has not been moved to bring the catheter tip to area 700 (2) the operator is looking at area 1700 for any reason. This new ROI information can be fed as input to the system in many ways including automatic follow-up of the catheter tip or follow-up of the area at which the operator looks using an eye tracker device (such as EyeLink 1000 available from SR Research Ltd., Kanata, Ontario, Canada) to indicate the desired ROI location to be in conjunction with the gazing point of the user or by using a computer mouse to indicate the desired ROI location.

With angular span of aperture sector 702 and at a constant rotation speed of collimator 500, the DPP in the annulus outside area 700 is 1/10 of the DPP inside circular area 700 and S/N in the annulus outside area 700 is $1/10^{1/2}$ of that of area 700, resulting in a lower image quality. To overcome this and maintain refreshment rate of the displayed frames of 10 fps with collimator 500 EC of 1/10 of a second as in the basic example of the invention, the rotation profile can be modified so that the collimator rotation speed in sector 1702 (FIG. 17B) that contains area 700 is reduced to 1/10 of the uniform speed and the rotation speed at the rest of the EC is increased to maintain EC of 1/10 of a second.

Figure 30:
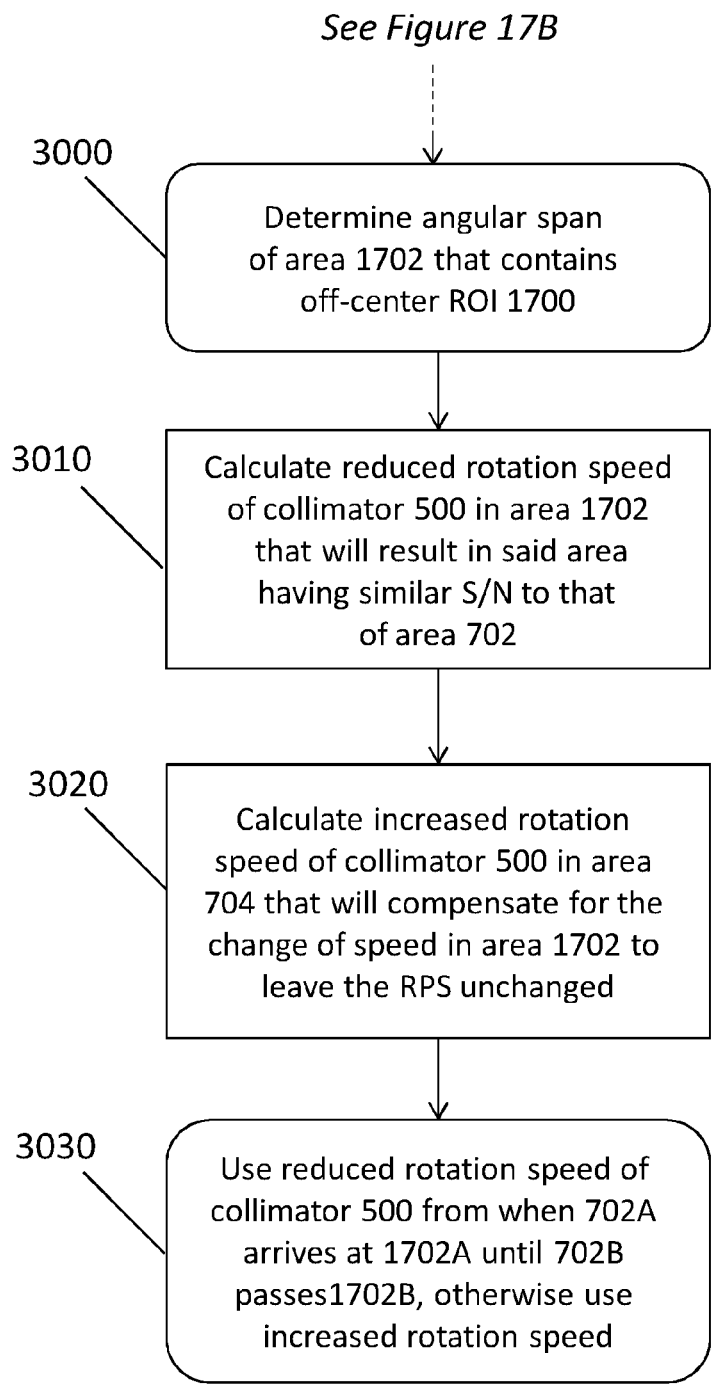
FIG. 30 is a flowchart referencing FIG. 17B, describing the change in rotation speed profile of a collimator to incorporate an ROI that is not in the center of the display.

This will be explained now in reference to FIG. 17B, and the corresponding flowchart in FIG. 30 with example of actual numbers.

Let us assume that the angular span of sector 1702 that just contains area 1700 is 54 degrees (step 3000). The first edge of sector 1702 is 1702A and is located at angular position 63 degrees and the second edge of sector 1702 is 1702B and is located at angular position 117 degrees. That is, sector 1700 is centered on angular position 90 degrees.

In step 31010, the reduced rotation speed of collimator 500 is calculated for area 1702, that will result in area 1702 having similar S/N to that of area 702. In this example, when edge 702A of sector 702 approaches angle 63 degrees (the location of 1702A) the rotation speed of collimator 500 is reduced to 1 rps. This rotation speed is maintained until edge 702B of sector 702 reaches the position of edge 1702B (117 degrees). From this point the rotation speed of collimator 500 is increased again. In step 3020 the increased rotation speed of collimator 500 in area 704 is calculated, that will compensate for the change of speed in area 1702, to leave the total rps unchanged. For simplicity it will be assumed that acceleration and deceleration are extremely high and therefore acceleration and deceleration times are definitely negligible for this example. Per the explanation above, collimator 500 rotation profile then includes 54+36=90 degrees (¼ of the EC rotation) at a speed of 1 rps. To compensate for this and complete the EC at an average of 10 rps the rotation speed of collimator 500 at the rest ¾ of the EC rotation must be increased to Xrps, satisfying the following equation:

$$1\text{rps} \cdot 1/4 + X\text{rps} \cdot 3/4 = 10\text{rps} \qquad \text{(Equation 7)}$$

Therefore:

$$X\text{rps} = (10\text{rps} - 1\text{rps} \cdot 1/4)/(3/4) = 13\text{rps} \qquad \text{(Equation 8)}$$

That is, during the rest of the 270 degrees rotation of the EC, the rotation speed should be 13 rps.

With this rotation profile sector 1702 is exposed to the same DPP as area 700 and the S/N of area 1700 is also the same as area 700 as desired.

It would be appreciated that in the sector range outside sector 1702, for which the collimator rotation speed is increased to 13 rps, the DPP is reduced below that of the DPP of constant rotation speed to 1/13 the DPP of area 700.

It would also be appreciated that area 1700 was presented here as an example do demonstrate the design of rotation profile according to different ROI geometries. Area 1700 might be different in shape and location and it might be possible that more than one ROI is added to the basic ROI of circle 700. Such variations are handled with profile variations of the same concept described above.

It would also be appreciated that acceleration and deceleration mentioned above might take unreliable part of the EC and must be accounted for. Let us assume in the next example that acceleration and deceleration occupy 45 degrees of rotation each and that they are uniform. In this case acceleration has to start 45 degrees before edge 702A arrives at the position of edge 1702A and deceleration starts when edge 702B arrives at the position of 1702B. All other parameters of the system are the same. If X indicates the rotation speed during the 180 degrees of EC and Y is the average rotation speed during each of the 45 degrees acceleration deceleration sectors then the following equation needs to be satisfied to maintain EC of 0.1 s (or average rotation speed of 10 rps):

$$1\text{rps} \cdot 1/4 + 2 \cdot Y\text{rps} \cdot 1/8 + X\text{rps} \cdot 1/2 = 10\text{rps} \qquad \text{(Equation 9)}$$

Given constant acceleration and deceleration between 1 rps and 10 rps, Y=(1+10)/2=5.5 and the high rotation during 180 degrees is 16.75 rps. It would be appreciated that this approach presented through the example above is applicable also to other acceleration profiles, other collimators and other operation schemes (such as different fps rates). It would also be appreciated that pixel correction methods described above are fully applicable also to variable rotation speed profiles, Different Refreshment Rates for Different Areas of the Image:

It has been presented above (with the example of collimator 500 of FIG. 5 and operation mode of constant rotation speed of the collimator at 10 rps and display-frame refreshment rate of 10 fps) that the DPP of circular area 700 of FIG. 7 is 10 times higher than the DPP of the annular area constructed of sectors 702 and 704 (to be denoted "annulus" for short). Therefore the S/N in area 700 is also $10^{1/2}$ better than the S/N in the annulus area. The refreshment rate of the entire image 120 (FIG. 2) is the same: 10 fps. The temporal resolution of the entire frame is 0.1 second (s). In the previous example, each display-frame was constructed from the data of one frame acquired from camera 116. Area 200 on the display 118 is equivalent to area 700 on the sensor. Area 200 is exposed to 10 times the DPP of area 202 and the S/N in area 200 is $10^{1/2}$ better than the S/N the annulus area 202. With each EC of collimator 500 the data is read from sensor 714, processed and displayed on monitor 118. The complete image 120 is refreshed then every 0.1 s.

In the following example of the invention it is desired to improve the S/N of annulus 202.

In a first example, while area 200 is refreshed every 0.1 s with the data read from sensor 714, annulus 202 is refreshed only every 1 s. During this 1 s, the data received from sensor 714 for pixels of annulus 202 is used to generate an annulus image that is the sum of the 10 previous frames. In a simplified form, all 10 frames indexed j=1 to 10 are stored. Then for each pixels i in the range of annulus 202 the sum of values is calculated: Pni=Σpij. Pni are then corrected and displayed where n is index number for every set of 10 frames. Therefore for j=1 to 10, the pixels of the sum frames is P1$i$. For frames j=11 to 20, the pixels of the sum frames is P2$i$. For frames j=21 to 30, the pixels of the sum frames is P3$i$ and so on. With this example therefore we get a display of image 120 where the S/N of annulus 202 is similar to that of area 200 although annulus 202 receives 1/10 of the DPP in every unit time of area 200. The compromise is that annulus 202 is refreshing every 1 s comparing to every 0.1 s of area 200 and the temporal resolution of annulus 202 is 1 s comparing to 0.1 s of area 200.

In a second example, after the first 10 frames indexed j=1 to 10 were acquired and stored and displayed as the sum of the pixels for annulus 202, refreshment of annulus 202 is made in a different way. Instead of keeping the display of annulus 202 for 1 s until j=11 to 20 are acquired, the displayed image is refreshed after 0.1 s as follows:

Frame j=11 is acquired and stored instead of frame 1. Therefore the previously stored frames 1,2,3,4,5,6,7,8,9,10 the following frames are stored: 11,2,3,4,5,6,7,8,9,10. This set of frames is handled in the same way as the pervious set and annulus 202 is refreshed. After additional 0.1 s frame indexed 12 is acquired and is stored instead of the frame indexed 2: 11,12,3,4,5,6,7,8,9,10. The set is now processed in the same way and annulus 202 display is refreshed. This process repeat itself and as a result annulus area is refreshed every 0.1 s, same as area 200. The temporal resolution of annulus 202 is still 1 s comparing to area 200 with temporal resolution of 0.1 s. The S/N in annulus 202 is similar to the S/N of area 200. In a third example, an intermediate approach is presented. Following the first example, instead of summing pixels of 10 frames and refreshing annulus 202 every 1 s, summing can be done every 5 frames and refreshment od annulus 202 can be made every 0.5 s. The S/N of annulus 202 is now $1/2^{1/2}$ of the S/N of Area 200 but still better than $1/10^{1/2}$ of the basic example of collimator 500 and the temporal resolution is only 0.5 s comparing to 1 s of the first example of this method.

It would be appreciated that also in the second example an intermediate approach can be used where, instead of replacing each time one of 10 frames, the replacement is of one frame in a set of 5 frames: 1,2,3,4,5 then 6,2,3,4,5 then 6,6,3,4,5 and so on. Here we gain again the refreshment of annulus 202 every 0.1 s but with temporal resolution of 0.5 s and S/N of annulus 202 is now $1/2^{1/2}$ of the S/N of Area 200 but still better than $1/10^{1/2}$ of the basic example of collimator 500.

Figures 18A, 18B:
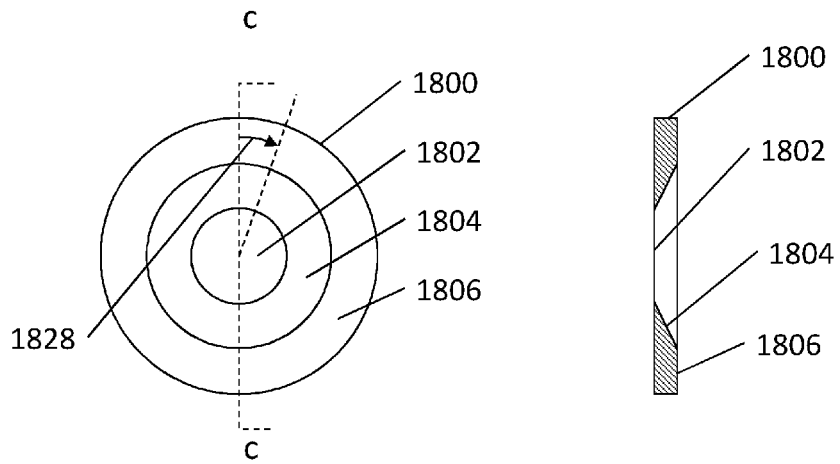
FIG. 18 is a schematic illustration of an example of a non rotating collimator and the effect it has on an image displayed on the monitor.

It will be appreciated that this method can be implemented also for collimators that are not rotating collimators such as the one of FIG. 18. FIG. 18A provides a top view of the collimator and FIG. 18B is cross section c-c of FIG. 18A.

Figure 18C:
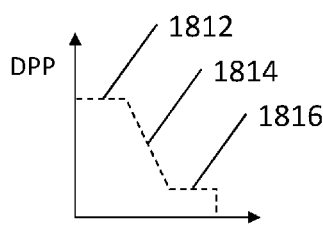

Collimator 1800 provides a similar function of x-ray reduction as other collimators of the invention. It has an aperture 1802 that allows all the radiation in that area pass through, annulus 1806 that reduces the radiation passing through the area at amount depending on the material (typically aluminum) and the thickness of the material and annulus 1804 with thickness changing as a function of the distance from the center, starting at thickness zero on the side of aperture 1802 ending at the thickness of annulus 1806 on the side of annulus 1806. FIG. 18C provides a schematic DPP graph as a function of distance from the center: r.

It is assumed that beyond annulus 1806 radiation is fully blocked. For the purpose of the description of this example radiation that is scattered from collimator 1800 is ignored. For this example it is also assumed that DPP passing through annulus 1806 is 1/10 the DPP passing through aperture 1802. Frame rate is 10 fps and display-frame refreshment rate is 10/s. As described in the above examples S/N of the image part associated with annulus 1806 is $1/10^{1/2}$ of the S/N associated with aperture 1802. To display an image where the S/N of the area associated with annulus 1806 is similar to the S/N in the area associated with aperture 1802 any of the methods above can be used.

Figure 18D:
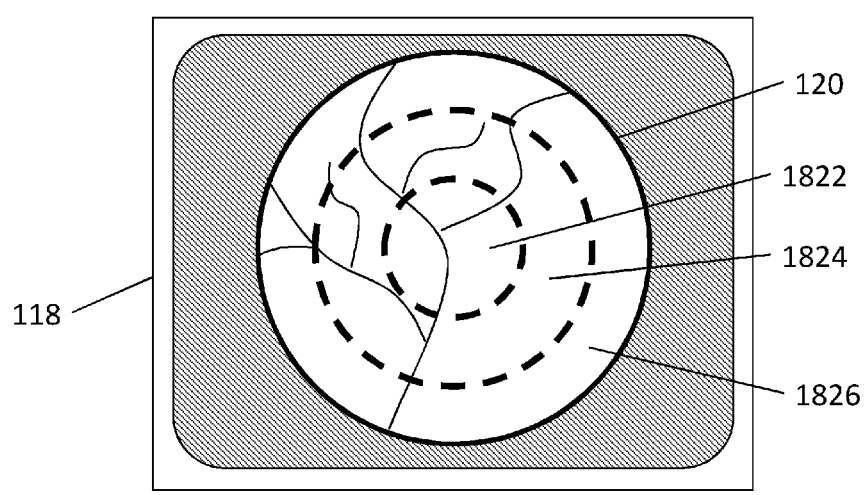

FIG. 18D provides a representation of monitor 118 with the displayed frame associated with collimator 1800. Circle 1822 is the area associated with radiation arriving through aperture 1802 of collimator 1800. Annulus 1824 is the area associated with radiation arriving through annulus 1804 of collimator 1800. Annulus 1826 is the area associated with radiation arriving through annulus 1806 of collimator 1800. It would be appreciated that while the example of annulus 1804 in FIG. 18B is linear change of thickness, the example of change in radiation of 1814 in FIG. 18C is of a non-linear thickness change. That is, many different functions can be used to generate gradient in thickness 1804 to suit the desired gradual change in radiation between annulus 1800 and annulus 1806 of FIG. 18B.

In a first example, while area 1822 is refreshed every 0.1 s with the data read from sensor 714, annulus 1826 is refreshed only every 1 s. During this 1 s, the data received from sensor 714 for pixels of annulus 1826 is used to generate an annulus image that is the sum of the 10 previous frames. In a simplified form, all 10 frames indexed j=1 to 10 are stored. Then for each pixels i in the range of annulus 1826 the sum of values is calculated: Pni=Σpij. Pni are then corrected and displayed where n is index number for every set of 10 frames. Therefore for j=1 to 10, the pixels of the sum frames is P1$i$. For frames j=11 to 20, the pixels of the sum frames is P2$i$. For frames j=21 to 30, the pixels of the sum frames is P3$i$ and so on. With this example therefore we get a display of image 120 where the S/N of annulus 1826 is similar to that of area 1822 although annulus 1826 receives 1/10 of the DPP in every unit time of area 1822. The compromise is that annulus 1826 is refreshing every 1 s comparing to every 0.1 s of area 1822 and the temporal resolution of annulus 1826 is 1 s comparing to 0.1 s of area 1822.

For annulus 1824, we shall use here the example where the DPP decreases linearly over the width of annulus 1820 from DPP of 1822 to 1/10 of this DPP, the DPP of annulus 1826.

In this example one may divide annulus 1824 to 8 annuluses of equal radius step so that the average DPP in the smallest annulus #1 is 9/10 of 1822, the average DPP in the next annulus #2 is 8/10 of 1822, annulus #3 is 7/10 and so on until the last annulus #8 that has 2/10 DPP of 1822.

Whenever a value is mentioned in reference to the above segments (annuluses #1 through #8) the value is the average value of that segment in consideration of the thickness variation of the collimator over that segment. When the purpose is to provide on the entire displayed image 120 the same S/N and keep temporal resolution of up to 1 s, it can be done in a simple way for annulus #5 (½ DPP than in area 1822) and annulus #8 (⅕ DPP of area 1822) since the ratio of DPP in area 1822 and the DPP in annulus #5 is an integer. The same is the case for annulus #2.

In the case of annulus #5 adding 2 temporally successive frames as described in any of the above methods (with adequate pixel correction as described above) provides S/N similar to area 1822. Temporal resolution in this example is 0.2 s.

In the case of annulus #8 adding 5 temporally successive frames as described in any of the above methods (with adequate pixel correction as described above) provides S/N similar to area 1822. Temporal resolution in this example is 0.5 s.

For other annuluses (#1, #3, #4, #6, #7 and #8) the ratio of DPP in area 1822 and the DPP in any of these annuluses is not an integer. Therefore adding pixels of an integer number of frames (up to 10 considering the desired limit of not more than 1 s temporal resolution) will exceed the desired S/N or be less than the desired S/N.

Figure 31:
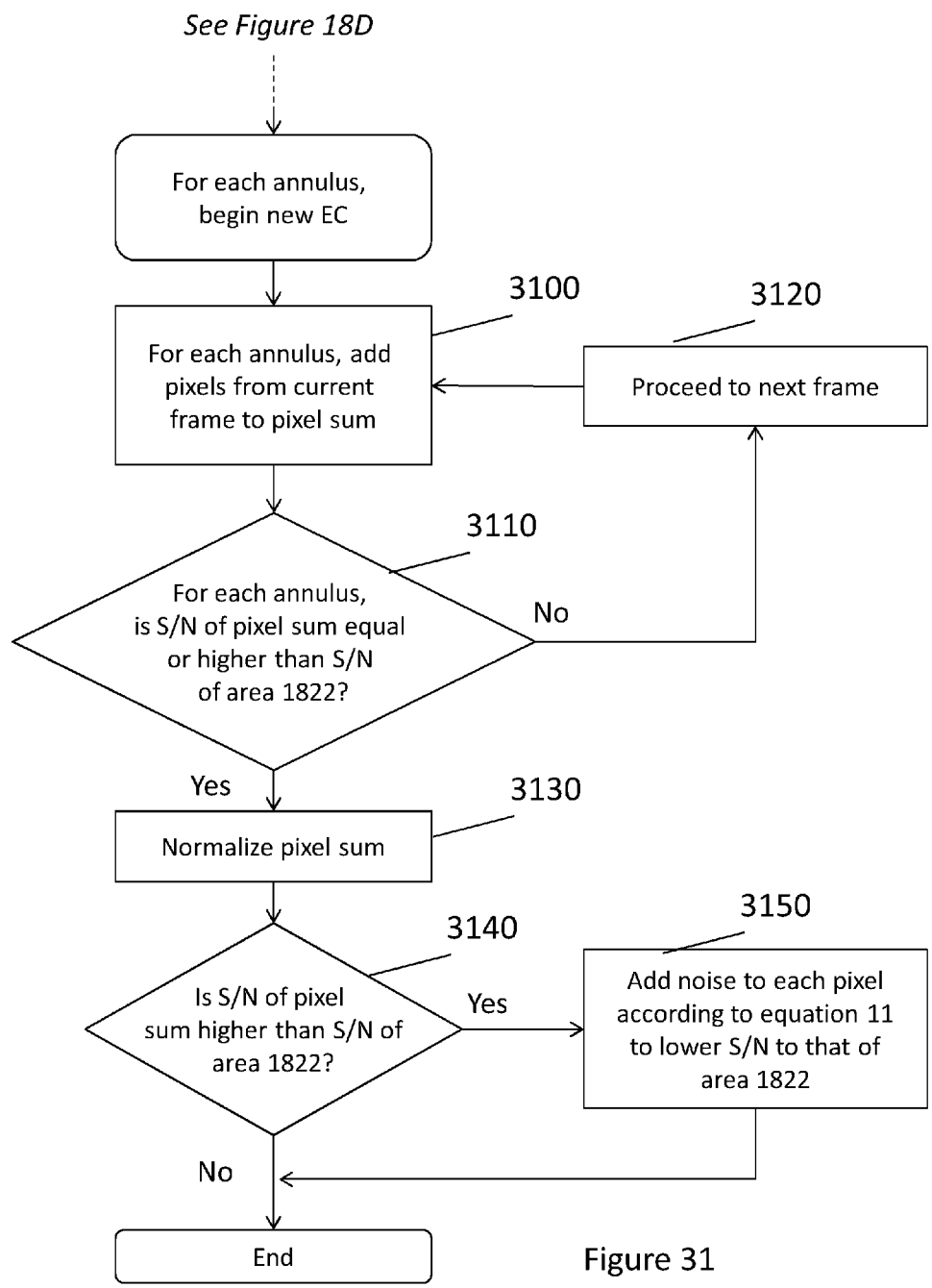
FIG. 31 is a flowchart referencing FIG. 18D, describing the adjustments necessary to achieve homogenous S/N across variable collimator annulus widths.

To achieve the desired S/N under the requirements of this example, the following method (which is described by flowchart in FIG. 31) can be applied:

1. For each annulus #m add the minimum number of pixels of temporally successive frames that provide S/N equal or higher to the S/N of area 1822 (steps 3100-3120).
2. Execute pixel correction (offset, normalization and so on as described above) (step 3130).
3. Add noise to each pixel in annulus #m compensate for the cases of S/N higher than in area 1822 (steps 3140-3150).

The above steps will be discussed in more details in reference to annulus #1. The DPP in annulus #1 is 9/10 the DPP of area 1822. The S/N in annulus #1 is $(9/10)^{1/2}$ of the S/N in area 1822. Therefore, according to step 1 above we need to add pixels of 2 temporally successive frames in the area of annulus #1 to make the S/N of the pixels in annulus #1 equal or higher than that of area 1822.

By adding the pixels of 2 temporally successive frames in the area of annulus #1 the effective DPP in the resultant frame in annulus 1 is 18/10 of the DPP in area 1822. The S/N in annulus #1 is now $(18/10)^{1/2}$ of the S/N in area 1822. To compensate for the too high S/N (and therefore result in possible visual artifacts in image 120, a Gaussian noise is added to each pixel to satisfy the equation:

$$(N_{1822})^2 = (N_{\#1})^2 + (N_{add})^2 \quad \text{(Equation 10)}$$

Where N1822 is the noise associated with a specific pixel in area 1822 for a specific object transmission, $N_{\#1}$ is the noise associated with the pixel that is the sum of 2 temporally successive pixels in annulus #1 (sum-pixel), having the same object transmission and after the sum-pixel has gone through pixel correction process (including, in the simplest correction form, dividing the value of the summed pixels by 1.8 to bring the affective DPP from 18/10 to 10/10—the same as in area 1822) and $N_{add}$ is the noise to be added to the sum-pixel to bring its' S/N to the same level as the equivalent pixel in area 1822.

In the example above, since the number of x-ray photons in the sum pixel of annulus #1 is 1.8 of the equivalent pixel (same object transmission) of area 1822, the noise of the sum-pixel is $(1.8)^{1/2}$ of the equivalent pixel in area 1822 and the S/N is also $(1.8)^{1/2}$ of the equivalent pixel in area 1822.

To calculate the amount of $N_{add}$ we use equation 10 in the form:

$$N_{add} = ((N_{1822})^2 - (N_{\#1})^2)^{1/2} \quad \text{(Equation 11)}$$

With the pixel correction division by 1.8.
Using numbers:

$$N_{add} = (1^2 - ((1.8^{1/2})/1.8)^2)^{1/2}$$

$$N_{add} = 0.667$$

Therefore, by adding this Poisson noise to the sum pixel we provide to that pixel a noise that is similar to the equivalent pixel in area 1822.

It is appreciated that all examples are calculated on a relative basis and therefore the pixel of area 1822 is 1.

It would be appreciated that the noise values in equation 10 are dependent on the pixel value and are typically the square rout of the pixel average level.

The same correction method is applicable to all the segments of annulus 1824 with suitable adjustments.

It would be appreciated that adding pixels of successive frames can be done by adding new frames each time before display-frame refreshment or using the FIFO method as described above.

It would be appreciated that dividing annulus 1824 to 8 segments (Annulus #1 through annulus #8) is provided as an example only. The higher the number of segments, the more uniform the S/N is over annulus 1824. Yet, the visibility of the non uniformity of the S/N adjustment is obscured by the S/N of the image therefore, above a certain number of segments the visual contribution of more segments is low and might be undistinguishable to the operator. Therefore one may limit the number of annulus segments in accordance to the S/N statistics of the image in the specific procedure.

The same methods for handling the non-uniform DPP regions such as annulus 1824 of the collimator example 1800 can be used also for collimators of the present invention such as those of FIG. 15C, FIG. 15D and all the collimators of FIG. 16 that also produce non-uniform DPP regions. These methods can be used with any collimator that generates different exposure regions, regardless of the method used by the collimator, whether the different exposure regions are generated by the shape of the collimator, by a motion of the collimator or by combining shape and motion. In all cases of motion of the collimator cycles of the same motion pattern simplify the image enhancement as described above but it is not a requirement to allow the image enhancement described above.

In the above example, in reference to the image area 1826 (FIG. 18D) corresponding with annulus 1806 (FIG. 18A), the discussion referred to basic processing of image area 1826: since the radiation there is 1/10 of the radiation in area 1822, one can sum last 10 frames in area 1826 to generate a processed 1826 area with S/N similar to that of area 1822.

In another approach, one may compromise S/N goal in area 1826 for adding less frames. For example, one may prefer summing only 5 frames and get S/N that is 0.71 of the S/N of area 1822 but, by doing so, improve temporal resolution of area 1826 by a factor of 2 compared to the case of summing 10 frames.

To compensate for the resulting ½ brightness in this example, each pixel value in area 1826 can be multiplied by 2. More generally, if one needs to sum M frames to get the brightness that is in conjunction with the brightness of area 1822, and instead m frames are summed (m can be any positive number), the pixel values of the pixels in area 1826 should be multiplied by M/m.

It would also be appreciated that the number of summed frames does not have to be an integer. For example, 4.5 frames can be summed. In this example FRMn is the last frame, FRMn−1 is the previous frame and so on. Summing last 4.5 frames can assume the form (for each pixel):

$$SUM=(FRMn)+(FRMn-1)+(FRMn-2)+(FRMn-3)+0.5\times(FRMn-4)$$

Brightness adjustment then uses the factor 10/4.5.

In some cases, due to the spectral change in radiation that goes through annulus 1806 (and also 1804), the x-ray in that area experiences a lower absorption coefficient when passing through the patient. Therefore, although when no patient or other absorbing matter is present the radiation for area 1826 is 1/10 that of the radiation for area 1822, when an absorbing object is present the effective radiation for area 1826 relative to that for area 1822 is higher than 1/10. It might be, for example, 1/8. In such a case, adding 8 last frames satisfies both the S/N and brightness criteria (being similar to that of area 1822). This can be used to sum less frames, especially in dark areas (high absorption coefficient).

Figure 17A:
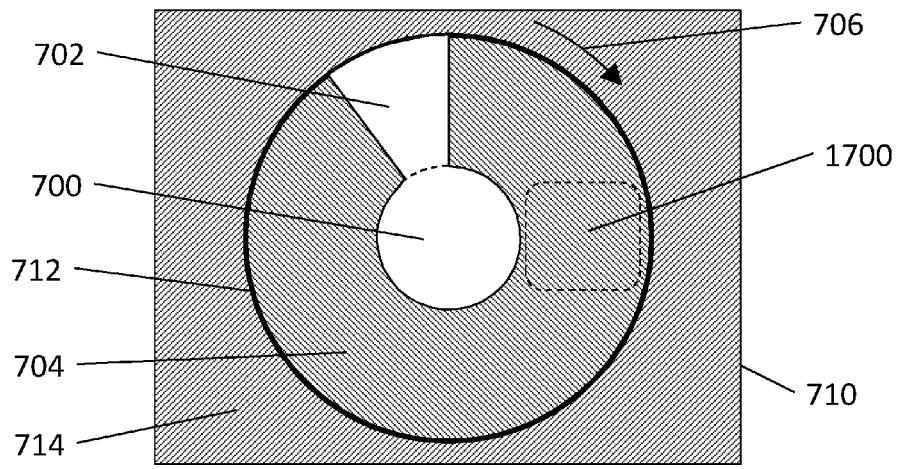
FIG. 17A is a schematic illustration of an example of ROI that is not generally located around the center of rotation.
Figure 17B:
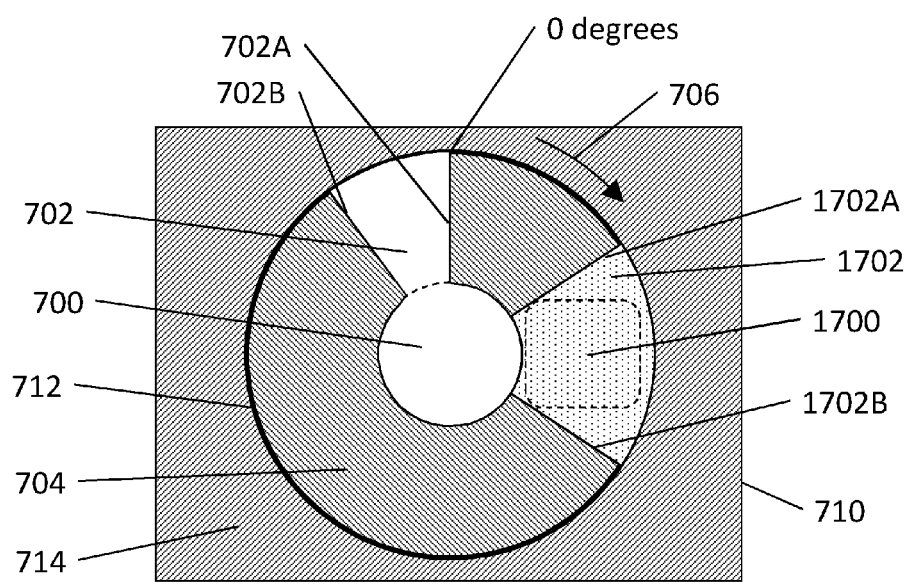
FIG. 17B is a schematic illustration of an example of changing the rotation speed profile of a collimator to enhance the image quality of the ROI of FIG. 17A.
Figure 19A:
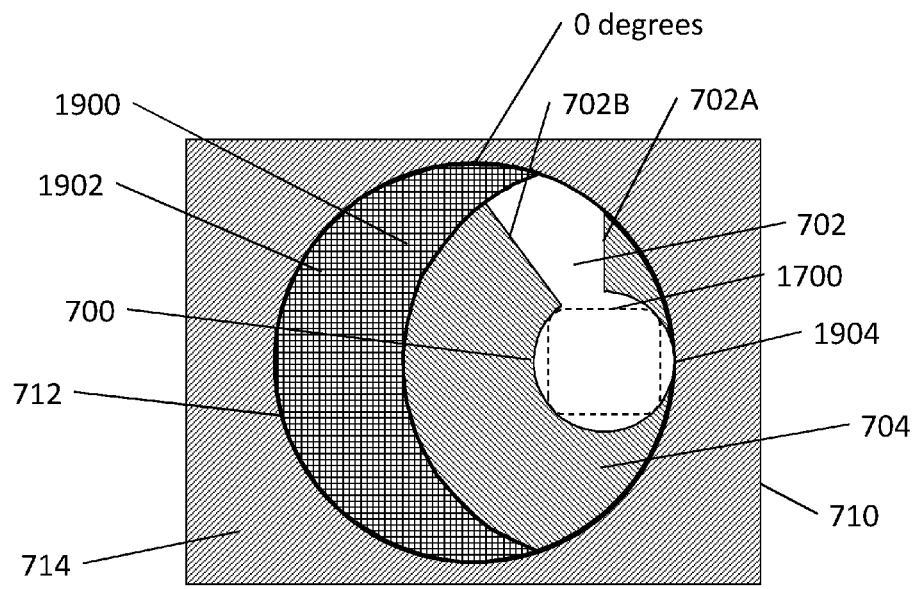
FIG. 19 is an example of the ROI of FIG. 17A and a collimator that can be displaced to bring the center of rotation to generally the center of the ROI.

In yet another example of the invention when the ROI shifts to area 1700 as presented in FIG. 17A, instead of adjusting the rotation profile of collimator 500 as explained in reference to FIG. 17B, the whole collimator can be displaced linearly, in direction parallel to the plane of collimator 500, so that the x-ray radiation passing through circular aperture 504 of FIG. 5 is now centered about area 1700 as shown in FIG. 19A on camera sensor 710. It is assumed that the only radiation that can arrive at the collimator input surface 112 is radiation that passes through the aperture of collimator 500 (circular hole 505 and sector hole 506). Therefore area 1902 in the sensor is shadowed out in FIG. 19A (no radiation arrives at the corresponding area of image intensifier input 112) and only the area including 700, 702 and 704 limited by boundary 712 is exposed. The exposed area is then the overlap between two circles with centers shifted one relative to the other and indicated in FIG. 19A by the numerical indicator 1900.

This desired function of the invention is provided here within area 1900 by circular hole 504 that enables higher DPP in area 700 and sector hole 506 associated with the rest of the image area enabling only 1/10 of the DPP of hole 504.

Figure 19B:
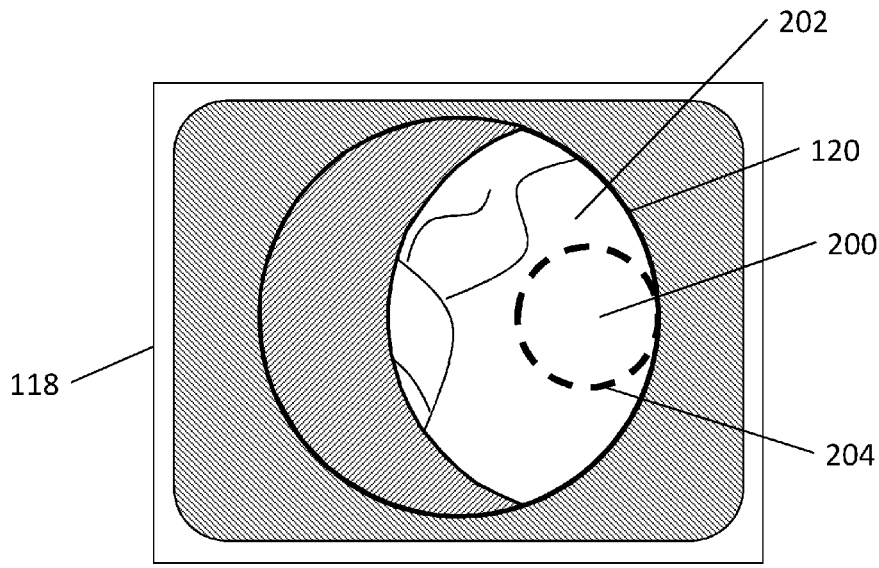

FIG. 19B illustrates the appearance version of FIG. 2 according to the example of FIG. 19A.

Collimator 500 can be moved in X-Y plane (see coordinate system 126 of FIG. 1A) using any common X-Y mechanical system. For example, annulus shaped static part 1016 of FIG. 10C is connected to an X-Y system instead of being connected to the x-ray tube structure and the X-Y system is connected to the structure of the X-Y tube, thus enabling the collimator of FIG. 10C, in this example, to move in X-Y plane as desired for the example of FIG. 19A.

It would be appreciated that the above methods such as pixel correction, S/N adjustments, adding pixels of different frames are fully applicable to the example of FIG. 19A with the adjustment of to the displacement of the collimator. The X-Y shift method is applicable to any of the collimators of this invention.

It would be appreciated that also displacement along a line (X axis for example) instead of X-Y can be applied in the same way with the limitation of ROI areas that can be handled this way over image 120 area.

X-Y mechanical systems can assume many designs, including such as Motorized XY Table ZXW050HA02 available from Shanghai ZhengXin Ltd, Shanghai, China. The custom design of X-Y mechanical systems is common in the art and is often made to optimally suit the needs of the application. One such provider of custom designed X-Y mechanical systems is LinTech, Monrovia, Calif., USA.

Figure 20A:
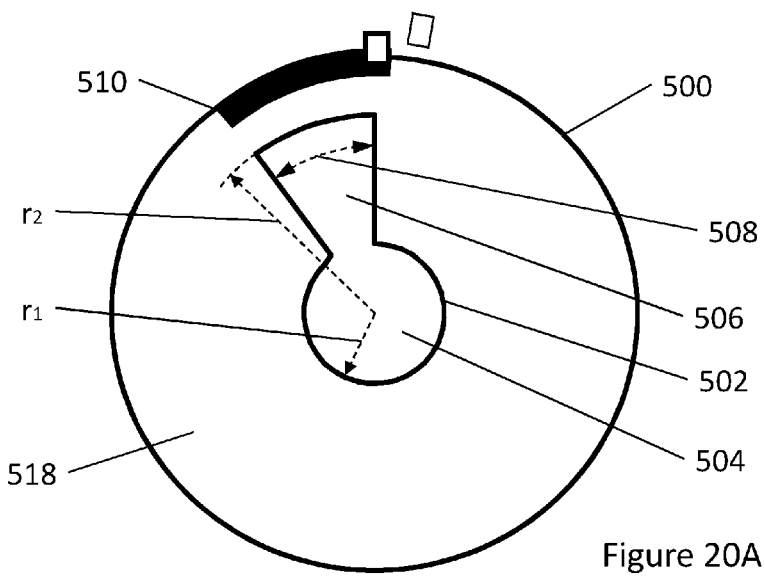
FIG. 20A is the same collimator example of FIG. 5 provided here for visual comparison with the collimator of FIG. 20B.
Figure 20B:
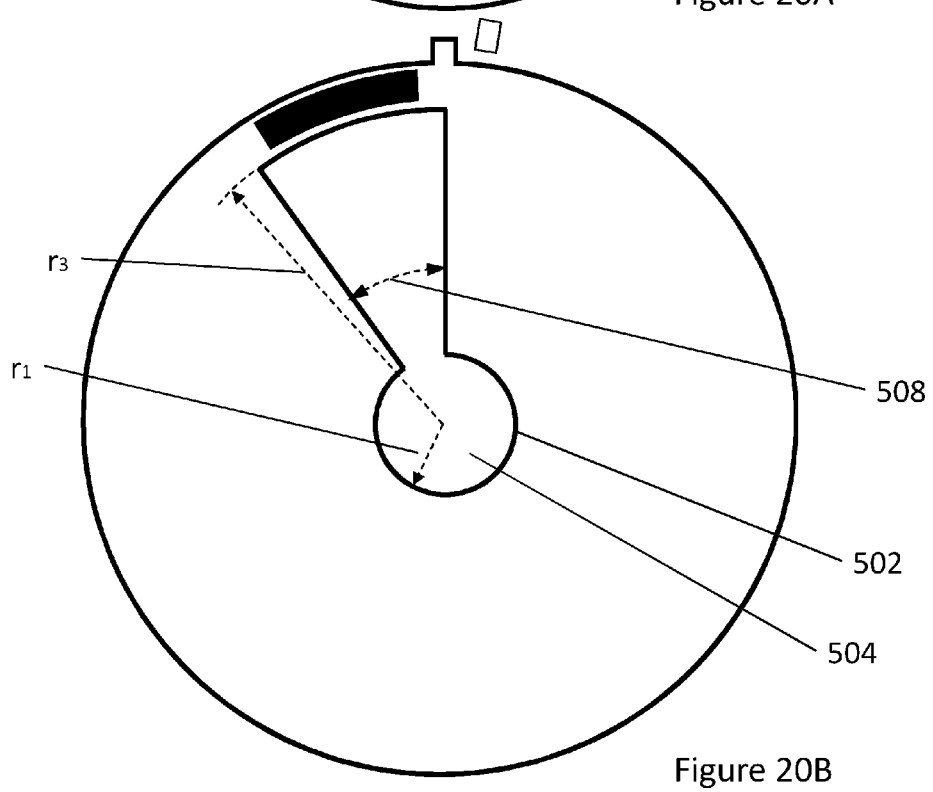
FIG. 20B is an example of a version of the collimator of FIG. 5 with larger diameter and longer sector hole, used to avoid image shadowing during displacement of the collimator.

It would be appreciated that the diameter of collimator 500 can be increased so that the length of sector 702 is increased to r3 as shown in FIG. 20B. FIG. 20A is the collimator of FIG. 5 provided here as FIG. 20A for easy comparison with the collimator of FIG. 20B. Angle 508 is the same (36 degrees in this example), the diameter of circular hole 504 is the same (r1). R3 is large enough to incorporate the complete field of view of image intensifier input 112 also when the collimator is displaced laterally as explained in reference to FIG. 19. With this design, the complete image area 120 of FIG. 19B remains active without any shadowed area such as 1902 in the example of FIG. 19. This collimator enlargement can be implemented in any collimator of the invention.

For the example of FIG. 19, where the maximum displacement desired is up to the point that the edge circular hole 700 is just in one point contact anywhere on the edge of image 712 edge (such one example point is point 1904 in Figure b19A) the required radius r3 of the sector hole can be calculated as follows, in reference to FIG. 20B:

$$r3=A-r1 \quad \text{(Equation 12)}$$

Where A is the diameter of the image intensifier input 112 B (see FIG. 3) scaled to its' projection in the collimator plane. That is:

$$A=B\cdot(D1/D2) \quad \text{(Equation 13)}$$

Figure 32:
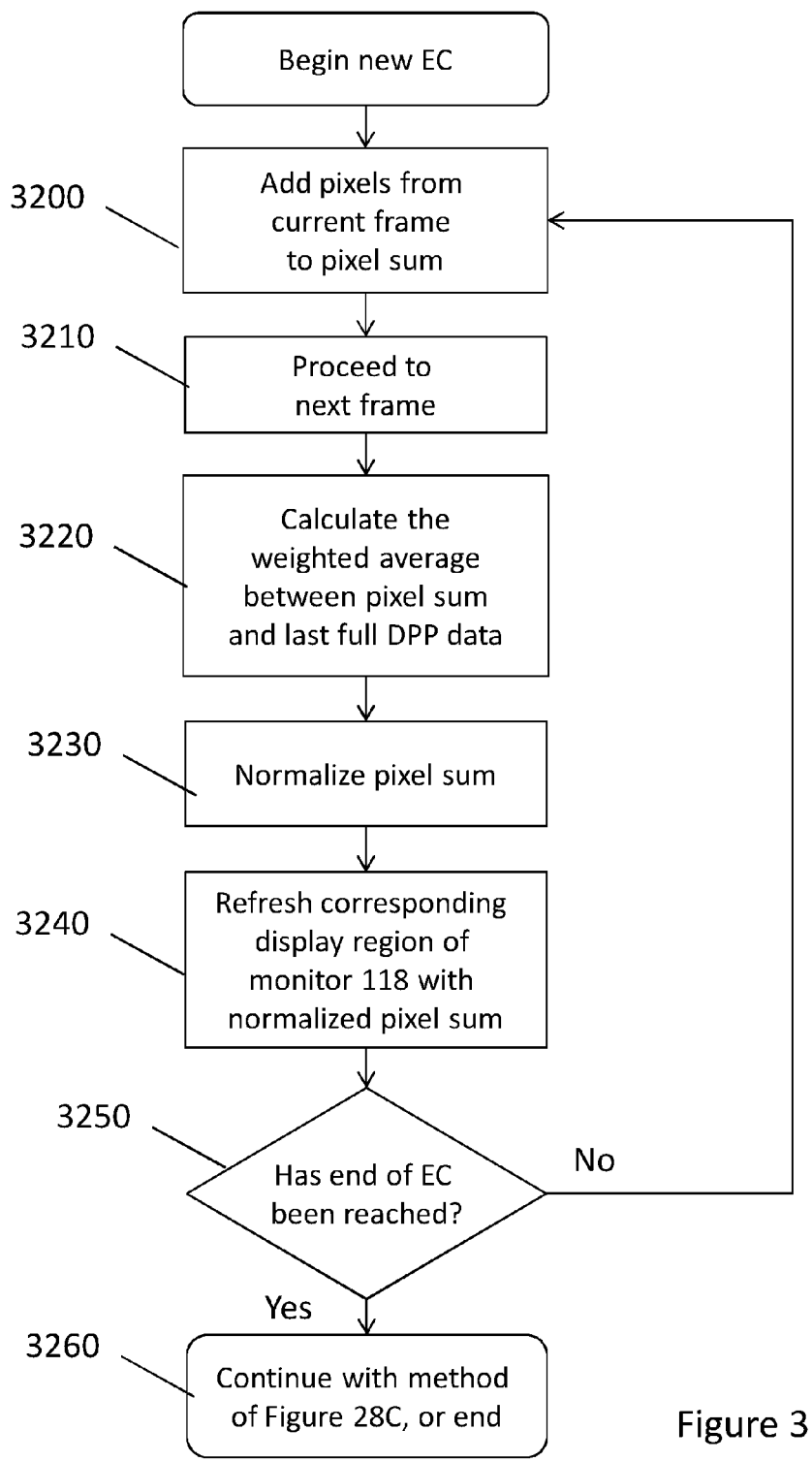
FIG. 32 is a flowchart describing a method for gradually shifting the display for an image region previously in the ROI that has moved into the background.

In the process of moving the collimator in X-Y plane, pixels that have been exposed to full DPP (through area 504) may change status to be exposed at 1/10 DPP since area 504 has moved and such pixels are not included in that area anymore. It would be appreciated that 1 s a pixel has changes status from being included in area 504 and full DPP to be outside area 504 and 1/10 DPP, considering the operation mode of this example, 10 frames of 1/10 DPP have been already acquired and the processing of this pixel for display is made in any of the methods described above that use last 10 frames to provide S/N same as within area 504 (or 5 frames after 0.5 s in another example). During the 1 s transition another handling is required to keep the S/N of this pixel the same as it was when it was included in area 504. Reference is made to FIG. 32. In step 3200, pixels from the current frame are added to the pixel sum, and the next frame is considered (step 3210). The frames summed thus far in the transition period are combined in a weighted sum with the full DPP data (step 3220), where the full DPP data is weighted in order to compensate for the lower DPP of the new frames and retain a consistent S/N. For instance, one frame into the transition, the display will be a weighed sum of 90% full DPP and the one new frame. After two frames, 80% full DPP and the two new frames, and so on. The weight of the full DPP attenuates its effective dose to represent the DPP necessary to keep the S/N of the pixels the same as it was when they were included in area 504.

In step 3230, normalization if performed, and then the updated image is displayed (step 3240). The process continues for a full EC, where the new frames progressively receive more weight compared to the old full DPP data.

When 10 frames have passed, the transition period is over and methods such as the one described in FIG. 28C can begin to operate (step 3260).

An example is provided below for further clarification: In this example, with refreshment rate of 0.1 s and temporal resolution that varies from 0.1 s to 1 s the following procedure is implemented, where N is the index of the last full DPP frame for that pixel:
1. At time 0 display for the pixel 100% the last full DPP data of frame N. Temporal resolution is 0.1 s.
2. At time 0.1 s display for the pixel a weighted sum of 90% the last full DPP data of frame N and 100% of the new DPP data of frame N+1.
3. At time 0.2 s display for the pixel a weighted sum of 80% of the last full DPP data of frame N, 100% of the DPP data of frame N+1 and 100% of the DPP data of frame N+2.
4. . . .
5. . . .
6. . . .
7. . . .
8. . . .
9. . . .
10. At time 0.9 s display for the pixel a weighted sum of 10% the last full DPP data of frame N and 100% of the new DPP data of each of frames N+1, N+2, . . . , N+9.
11. At time 1.0 s display for the pixel a weighted sum of 0% the last full DPP data of frame N and 100% of the new DPP data of each of frames N+1, N+2, . . . , N+9, N+10. Temporal resolution has now changed to 1 s.
12. Continue with methods described above for image improvement for 1/10 DPP regions. Temporal resolution is 1 s.

It would be appreciated that in the case of the method of refreshing the pixels of 1/10 DPP in a rate of only 1 fps the last full DPP data is presented for 1 s after the change of the pixel to 1/10 DPP exposure and afterwards the average of the last 10 frames of 1/10 DPP will be used to refresh the pixel.

In the case that a pixel changes status in the opposite direction, that is changing from 1/10 DPP area to full DPP area, this transition is instant and in the first 0.1 s after the status change the displayed image is refreshed with the first 0.1 s frame of the full DPP.

It would be appreciated as explained in reference to FIG. 1A, that the above methods are applicable also for relatively high frequency pulse x-ray. The term "relatively high frequency" is relative to the collimator design and operation mode. In the example of collimator 500 of FIG. 5, that has a sector angular span of 36 degrees and rotates at 10 rps, the pulse frequency should be at least at a frequency of 100/s so that there is at least one x-ray pulse per each 36 degrees area of a frame. To simplify pixel correction scheme, it is also desired that the x-ray pulse frequency would be a positive integer multiplication of minimum frequency. In this example: 200/s, 300/s, 400/s and so on. In this example 1,000/s (10 times the minimum frequency can be considered relatively high frequency.

It is appreciated that no collimator is totally opaque to x-ray and collimators are constructed to block most of the x-ray in the opaque regions. With HVL (half value layer) of 0.25 mm (similar to that of lead), 3 mm thick collimator allows $0.5^{(3/0.25)}=1/4096$ of the incident x-ray radiation to pass through (without scatter). The term "essentially opaque" will be used to describe these practical collimators. Most of the collimators described hereinabove are constructed of essentially opaque region such as 518 of FIG. 5 and apertures or holes as 504 and 506 of FIG. 5. Collimators such as the example of FIG. 18 are different since, in addition to the essentially opaque region 1806 and the aperture 1802 they include semi-opaque regions such as 1804 of FIG. 18A.

Collimators according to this invention can be mounted on an x-ray system as stand-alone or together with another collimator, for example, such that is designed to limit the x-ray to a part of input area 112 of the image intensifier. Collimators of the invention and other collimators may be placed in any order along the x-rat path. The exposed part of area 112 is the remaining of the superposition of the area all the collimators in the path of the x-ray block. In the design of such successive arrangement, the distances of each of the collimators from the x-ray source and distance to area 112 needs to be considered with the geometry of the collimators, as described above, to get the desired functionality.

Image Optimization Using Dynamic ROI and Eye Tracker

In another example, any of the above examples of collimators and examples of image processing (and also examples that are not described hereinabove) can be used with an eye tracker to further enhance the image perceived by the user. In a typical multiple frame x-ray imaging system an area is defined, typically centered about the center of the image, to determine what might generally be called the brightness of the image. Sometimes contrast of the image is also determined based on this area. Typically the area is smaller than the entire image but it can also be an area of a size similar to the entire image.

Based on the image content in this area, various parameters related to the image quality might be determined to optimize the image for the user, such as:
1. x-ray tube current (whether in continuous or pulse modes)
2. x-ray tube Peak Kilo Voltage (PKV)
3. x-ray pulse length
4. AGC (Automatic Gain Control), whether analog or digital
5. Tone correction or tone-adjustment of the image implemented in various functions such and brightness, contrast, gamma, offset, gain, n-degree linear functions, non linear functions etc.

One example of optimizing the image according to the image content in this area is to identify the 10% brightest pixels in this area, calculate the average value of these pixels and adjust the gain (multiply each pixel value by a constant factor) so that the average value is set to level 240 in an 8 bit display system that provides display levels 0 through 255.

The typical result of such parameters changes using the image data of the defined area is that the image in that area is optimized to the content of said image for visual perception of the user while image parts outside this area might not be optimized for visual perception of the user.

For example, a lung may be present in the optimization area. Since the lung is relatively transparent to x-ray radiation, the optimization operates to reduce radiation to make the lung appear at a desired brightness. As a result, the spine that is nearby, but outside the optimization area, will appear dark and visibility of details might be lost. To overcome this with the present art, the patient is moved until the spine is in the optimization area and optimization is made for the spine, brightening it up. But now, the lung is too bright and lung details in the image are degraded. This conflict can be resolved by using x-ray manipulating collimators such as those described above with the eye tracker.

According to the present invention, the X Ray tube input parameters may be controlled automatically or via user guided settings in order to enhance/adjust intensity (and obtain adequate image quality) within the ROI as well as the periphery and guarantee that certain features (such as a stent, tool or anatomy) are apparent and clearly visible.

In the present example, the ROI is not static but instead it follows the coordinates of the eye gazing of the user. The eye tracker provides a stream of (x,y) of the gazing point of the user on the screen. The ROI is moved to these coordinates, with a complementary adjustment of the collimator and the optimization is made for the image included in the ROI—where the user is gazing at.

As a result, the image is optimized in the area where the user is looking and where he needs the best image at any time without a need for any manual adjustments or compensations for the automatic image optimization function. It would be appreciated that this function can be used throughout the procedure or only during desired intervals of the procedure.

The image may be optimized per the ROI content using any of the above mentioned parameters or any other parameter that modifies the displayed value of a pixel in the image.

It would also be appreciated that the ROI does not need to be centered at the gazing point. The desired optimization can be made also when the ROI is selected so that it contains the gazing point.

It would be appreciated that the above optimization method can be applied also without using any of the above examples of collimators and examples of image processing. This method can be applied to a multiple frame x-ray imaging system that employs generally uniform DPP over the field of view of image intensifier input 112. An eye tracker is added to such a multiple frame x-ray imaging system to detect the gazing point of the operator in the image area. The above optimization is made then for an image area that contains this gazing point as described above.

Background Image Processing Using Tone-Correction Function

One of the effects of using a collimator of the type described in reference to FIG. 18A through FIG. 18D is the change of the spectrum of the x-ray radiation in the background (annulus 1806) Vs the ROI (Annulus 1802). The result of reducing x-ray DPP through the background filter (annulus 1806) is a change of the x-ray spectrum in that area of the image comparing to the ROI area of the image (ROI in short). This in turn results in different absorption characteristics of the x-ray in human tissue (or any other material) in the background area Vs the ROI. In the example of the collimator associated with FIG. 18A through FIG. 18D and considering also the example that the background area photon count per pixel is 10% of the photon count per pixel in the ROI in no presence of patient or phantom (110 of FIG. 1A), one might suggest that by multiplying each background pixel value by 10 (or by summing last 10 background images as described above), the background image will become similar to the image in the ROI. This is not the typical case. Typically, a more complex tone reproduction function is required to make the background image look more similar to the ROI image. This is explained in more details in reference to FIG. 21A through FIG. 21C.

It would be appreciated that the selection of 10% hereinabove is arbitrary and made only as an example. Other values between 1% and 90% can be selected as well as any value higher than zero and lower than 100%. The adjustment of the description for values other than 10% is obvious for those skilled in the art.

Figure 21A:
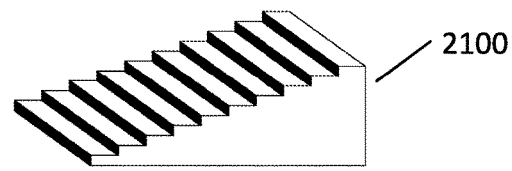
FIG. 21A presents a typical step wedge phantom for use with x-ray.

A typical tool used in the x-ray field for image research, measurements, calibrations and evaluations is the 10 step wedge as shown in FIG. 21A. It can be constructed of many materials. By placing such a step wedge in the x-ray path instead of patient 110 of FIG. 1A, a stripes-image is acquired, the pixels of each rectangular stripe are of a relatively similar value comparing to the difference between pixels of neighboring steps (assuming relatively high S/N). Average value in each stripe can be measured to produce the values of the 11 dotted bars 2104 in FIG. 21B. The horizontal axis represents the relative step thickness, number zero represents no absorption (a strip of air only), number 1 represents the thinnest step of step wedge 2100 and number 10 represents the thickest step of step wedge 2100, being 10 times thicker than the thinnest step, in this example.

The vertical axis represents a pixel value. In this example a 12 bit system was selected providing a dynamic range of 0÷4095. A 12 bit system was selected for this example since it is a popular system in this field for digital image processing but it would be appreciated that that any system can be used to realize the invention, that the adoption of the invention to other system is simple for a person skilled in the art and the scope of the invention is not limited by this example.

Also, in this example, the average pixel level in air was set to 4000, allowing 95 additional levels for pixel noise and avoid high noise digital cutoff at 4095. This selection is made as an example and it is appreciated that noise depends in such systems on the x-ray DPP and the value for air transmission should be made according to the preferred x-ray characteristics.

In this example, the filtering of x-ray intensity in the background, that results in change of spectral distribution of the x-ray radiation in the background, will change characteristics of absorption coefficient through the same step wedge 2100. The resultant pixel values for the background radiation for each step are shown as 11 black bars 2106 in FIG. 21B.

When implementing a first process of the background by adding last 10 background frames as described above (or multiplying each background pixel by 10), the initially-processed background pixel value in step zero becomes similar to ROI pixel value in step zero as shown by the leftmost girded bar in the 11 girded bars 2108, representing the average value of the steps in the background, after adding last 10 frames.

By examining bars 2108 Vs bars 2104 it becomes evident that, except for step zero, all 10 remaining 2108 bars are of higher values than the 10 remaining bars 2104. This results from the different absorption in the background due to spectral change made by annulus 1806 of the filter of FIG. 18A. For example, the average pixel value of step 5 in the ROI is 1419 but in the initially-processed background it is 2005. This results in apparent difference between the initially-processed background image and the ROI image.

Figure 21B:
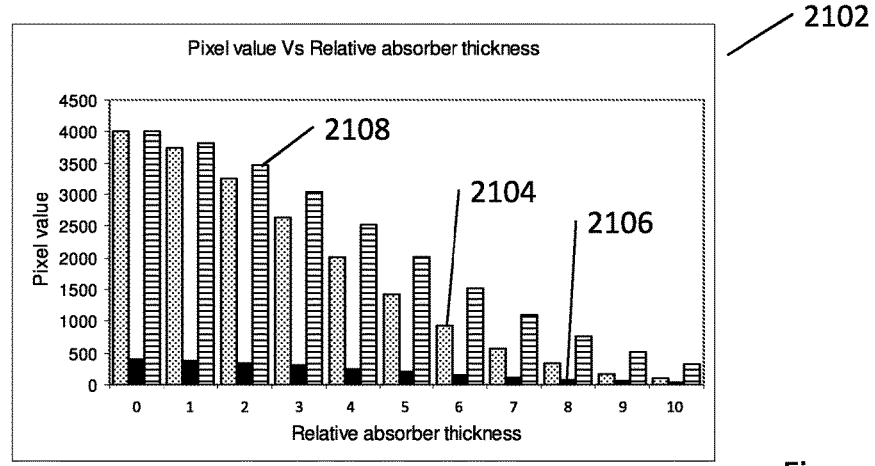
FIG. 21B demonstrates different absorption in ROI and background areas due to background filter and change in x-ray spectrum.

To resolve this, an additional processing step is required for the background image area (background in short). Such a correction function, in reference to the ROI area and the background area of the steps of FIG. 21B is shown as function 2112 of FIG. 21C and it will be called here tone-correction function. The process of changing an image using the tone-correction function will be called here tone-correction.

Tone-correction function 2112 is created by calculating the tone-correction factors for each of the 11 strips to bring the average pixel value of the backgrounds strip to the same average pixel value of the strip in the ROI area. Each such factor is the ratio of the average step pixel value in the ROI to the average step pixel value in the background. Factors for pixel values between these calculated values can be obtained using interpolation of any kind such as a cubical interpolation or fitting of any function to the 11 calculated points such as exponential or n-dimensional linear function. It is evident, in this example, that the lower the pixel value is, in the background area, the lower is the correction factor. For example, for initially-processed background pixel value 762 the correction factor is 0.44 (2114 in FIG. 21C). While for initially-processed background pixel value 2524 the correction factor is 0.79 (2116 in FIG. 21C).

Figure 21C:
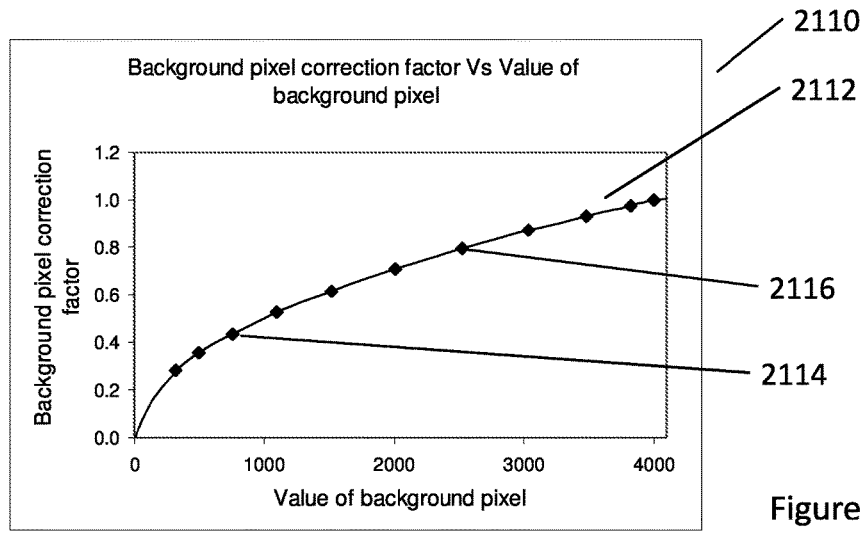
FIG. 21C is an example of a tone-correction function made to tone-correct the background image to fit the ROI image.

Tone-correction in this example refers to the multiplication of each pixel in the initially-processed background by the associated factor per the example of FIG. 21C.

The tone-correction function of FIG. 21C is used to further process the initially-processed background by multiplying each of the initially-processed background pixels by the associated factor (Background pixel correction factor) provided by tone-reproduction function 2112.

It would be appreciated that although, in this example, background was processed to become similar to the ROI but it is also possible to use the same approach to process the ROI to become similar to the background. It is also possible to execute the initial-processing on the background and execute the tone-reproduction on the ROI relative to the background. One only needs to exchange the words background and ROI in the example above to get a description of such a tone-correction.

It is also appreciated that initial-processing that results in similar step values for ROI and background is not a requirement for tone-correction. The tone correction can be executed without the above initial-processing or with initial processing that, for example, is designed to bring the background step zero to be half the value of the ROI step zero. This can be done, for example, by adding 5 last images instead of 10 last images in the present 10% background radiation. The tone-correction process is the same, only the tone-correction function (calculated in the same way) is different.

Tone-Correction Function Calculation Using Step Wedge

Figure 33A:
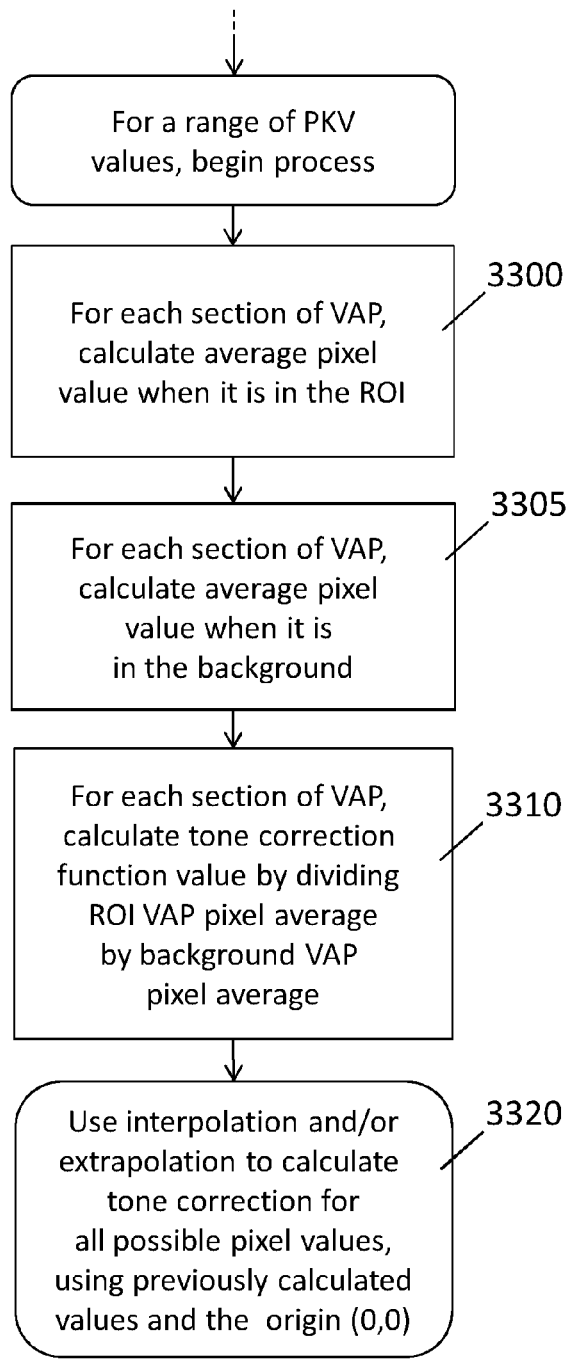
FIG. 33A is a flowchart referencing FIGS. 21A, 21B, 21C, describing the process of generating a tone correction function using a variable absorption phantom (VAP)

In the following example a method is presented in more details, to generate a tone-correction function for background image so to make it appear similar to that of the ROI. In this method reference is made to FIG. 33A.

The first phase of this method is the data collection.

To collect the data variable absorption phantom is used to provide for different absorption levels through the image area. Such a phantom may consist of a step wedge (such as the one of FIG. 21A), a linear wedge phantom, a variable thickness phantom of continuous slope function, a random thickness phantom or any other variable absorption phantom that will provide enough measurement points over the dynamic range of the image (0÷4095 in a 12 bit system), reasonably spread throughout the dynamic range to provide the desired accuracy. It would be appreciated that the more steps that are more evenly spread through the dynamic range—the more accurate the tone-correction function will be. A step wedge of 10 steps would be a reasonable choice for reasonable accuracy.

The variable absorption phantom (VAP) preferred material would be a material that behaves similar to live tissue. It is common to assume that water is a reasonable representation of a live soft tissue. There are materials that are considered water-equivalent that are used to produce such phantoms such as Plastic Water available from Supertech, Elkhart, Ind., USA. By using such materials the data collection better resembles the response to live soft tissue of the filtered background radiation spectrum and ROI radiation spectrum. Materials that are bone equivalent can also be used in such a variable absorption phantom but anyone skilled in the art would understand that it is merely an extension of the soft tissue discussion and therefore it will not be discussed in more details here.

The variable absorption phantom (VAP) is placed in the system of FIG. 1A instead of patient 110.

An image, or a set of images are acquired for a given PKV1. The reason for PKV being a parameter is the PKV dependent spectrum of the x-ray and thus, each tone-correction curve is calculated for a given PKV. The acquired images are designed so that, in the example of step wedge, each step is acquired with each of the x-ray spectrums of the ROI and the background. That is, either a part of the step is in the ROI and another part is in the background or, in one image the step is in the ROI and in another image the step is in the background.

Now, in this example, we choose to modify the values of the background pixels and to use the ROI as reference and adjust the background to appear similar to the ROI. It would be appreciated that the value of the pixels of the ROI can be adjusted to bring the ROI to look like the background (or other alternatives can be used as discussed above) but since the technique is completely analog to the present example it will not be discussed here in more details.

To do so, for each step i (including step zero of air) the average of 2 pixel groups are calculated:
1. (step 3300) pixels of step i that are in the ROI: AVGri
2. (step 3305) pixels of step i that are in the background: AVGbi These two numbers are used (step 3310) now to calculate the tone-correction function value for background pixel having the level AVGbi: F(AVGbi):

$$F(AVGbi)=AVGri/AVGbi$$

In the example of 10 steps step wedge+one step of air, a set of 11 tone-correction function values is provided:

$$\{F(AVGb0), F(AVGb1), F(AVGb2), \ldots, F(AVGb10)\}$$

In the example of 12 bit display system, 4096 correction values are desired so that each possible value of a pixel in the background has a correction tone-correction function value. Such values beyond the 11 values calculated above can be estimated using any interpolation and extrapolation approaches (step 3320) such as linear, $2^{nd}$ degree or any n-degree linear function fit or exponential function fit etc. The concept is the same, the difference is in the accuracy of the calculated tone-correction function, evaluated typically by how similar the background becomes to the ROI after the correction. This can be demonstrated using the following example.

An example table is provided for a step wedge used to measure the function values for each of the 10 steps plus the air step:

| Step | AVGri | AVGbi | F(AVGbi) |
| --- | --- | --- | --- |
| 0 | 4000.00 | 4000.00 | 1.00 |
| 1 | 3733.02 | 3819.97 | 0.98 |
| 2 | 3251.32 | 3483.85 | 0.93 |
| 3 | 2642.77 | 3034.31 | 0.87 |
| 4 | 2004.75 | 2523.83 | 0.79 |
| 5 | 1419.25 | 2004.75 | 0.71 |
| 6 | 937.69 | 1520.76 | 0.62 |
| 7 | 578.18 | 1101.69 | 0.52 |
| 8 | 332.71 | 762.18 | 0.44 |
| 9 | 178.67 | 503.57 | 0.35 |
| 10 | 89.55 | 317.73 | 0.28 |

In this example, step zero is an area without absorption, an area outside of the VAP. In this example, the background has gone also through the initial processing (such as adding last 10 frames to compensate for 10% background radiation as described in details above). For this reason AVGr0=AVGb0. In this example also the exposure has been set so that AVGr0=4000. For a given PKV this is done by determining, for example, the mA (milliampere) in a continuous multiple frame x-ray imaging system or determining the charge per pulse in a pulsed x-ray system (milliampere-second: mAs). For the purpose of the following discussion we shall refer to mA-0 as indicating the x-ray current setup to get AVGr0=4000.

Therefore, to get the correction factors for 0÷4095 an interpolation is needed for the range 319÷3999 and extrapolation is needed for the ranges 0÷317 and 4001÷40095. This can be done using one of the many curve fitting methods provided, for example, by MatLab, available from MathWorks, Inc., Natick, Mass., USA. The specific fitting method typically depends on the data.

It would be appreciated that not all steps must be used to calculate the tone-correction function but, typically, using more steps supports a better tone-correction function.

It would be appreciated that for the purpose of curve fitting, such a curve is always expected to pass also through the point (AVGb, F(AVGb))=(0,0). That is, when the absorber thickness is so high that the radiation is fully blocked by this thickness, the tone-correction value at this point is zero.

In accordance with the above example it can be illustrated with 2 additional lines in the table, presenting relative thickness of 200 and infinity:

| Step | AVGri | AVGbi | F(AVGbi) |
|---|---|---|---|
| 200 | 0.00 | 0.03 | 0.0068 |
| ∞ | 0.00 | 0.00 | 0.00 |

This additional point (0,0) can therefore be additionally used, with any set of measurements, for a better curve fitting.

It would also be appreciated that more than just 2 image areas such as ROI (1822 in FIG. 18D corresponding to filter section 1802 in FIG. 18A and FIG. 18B)) and background (1826 in FIG. 18D corresponding to filter section 1806 in FIG. 18A and FIG. 18B) are relevant to the tone-correction described above. Other image areas such as transition area 1824 in FIG. 18D corresponding to filter section 1804 in FIG. 18A and FIG. 18B are relevant. In the example of transition area 1824 the spectrum of the x-ray changes gradually as a function of distance from the ROI center due to the variable change in the filter thickness over annulus 1804. It would be appreciated that the tone-correction curve designed for background 1826 will not be optimal for transition area 1824.

It is desired therefore to divide transition area 1824 into a number of transition sub-areas, each transition sub-area has a relatively uniform x-ray spectrum after filtering. For each such transition sub-area a tone correction function is calculated (for each PKV) and is used to tone-correct the associated transition sub-area.

In another approach, the tone-correction function for a specific sub-area can be estimated from the tone-correction function of the background, taking into account the filter thickness in the specific transition sub-area. For example, for a transition sub-area thickness near that of the background, the tone correction function will be close to the tone-correction function of the background. One example for such an estimation of tone-correction values is provided in the following table

| Step | background | Near background | Near ROI |
|---|---|---|---|
| 0 | 1.00 | 1.00 | 1.00 |
| 1 | 0.98 | 0.98 | 1.00 |
| 2 | 0.93 | 0.94 | 1.00 |
| 3 | 0.87 | 0.89 | 0.99 |
| 4 | 0.79 | 0.82 | 0.98 |
| 5 | 0.71 | 0.75 | 0.98 |
| 6 | 0.62 | 0.66 | 0.97 |
| 7 | 0.52 | 0.58 | 0.96 |
| 8 | 0.44 | 0.49 | 0.94 |
| 9 | 0.35 | 0.41 | 0.93 |
| 10 | 0.28 | 0.34 | 0.92 |

The values for "Near background" and "Near ROI" are estimated from the background values using exponential evaluation in the form:

Estimated_value=Background_value$^E$

Where E=0.85 for the "Near background" values estimation and E=0.07 for the "Near ROI" values estimation.

Many other estimations can be used. The exponential estimation reasonably supports the exponential absorption characteristics of x-ray in matter.

The above method is executed for a range of PKV values to generate a tone-correction function for each such PKV value. For example, in the range of 50PKV to 150PKV, 5 tone-correction functions can be generated for 50, 75, 100, 125 and 150PKV.

In case, for example, that 90PKV is used with a patient, the tone-correction function can be interpolated from the tone-correction functions calculated for 75PKV and 100PKV using linear interpolation or any other interpolation. The interpolated tone-correction function can now be used for tone correction of the background generated with 90PKV radiation.

A common situation that might be encountered after executing the above tone-correction function calculation is that the actual image in use does not contain air sections and also maybe does not contain objects equivalent to steps 1, 2, 3 and 4. It is possible, for example, that the most "x-ray transparent" part in the examined object (patient 110 in FIG. 1A) reaches only level 2000 out or the 0÷4095 dynamic range. In such a case the x-ray current might be doubled to increase the DPP so that this area is brightened-up and arrives to level 4000.

In such a case, the tone-correction value originally designed to 4000 is not suitable anymore since the current 4000 is generated after absorption equivalent to the 2000 level of the tone-correction function.

Figure 21D:
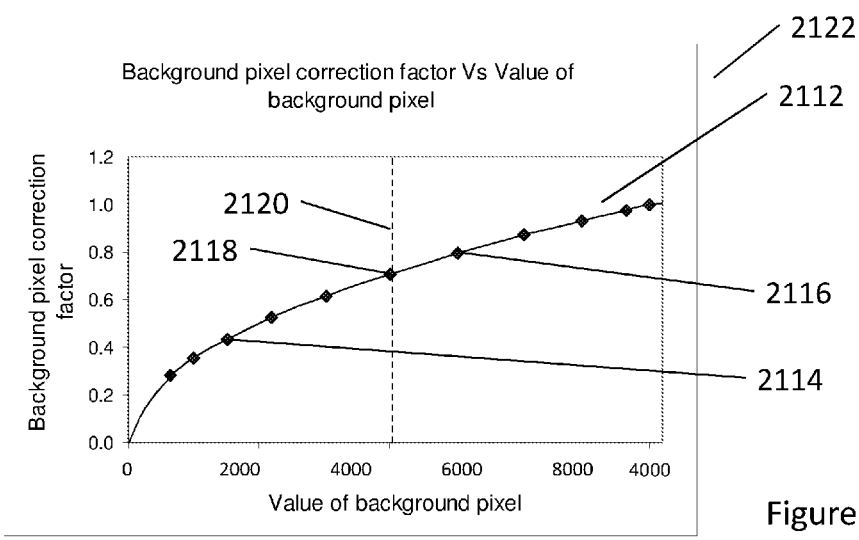
FIG. 21D is an example of a tone-correction function adjusted for ×2 x-ray exposure comparing to the x-ray exposure in the calculation stage.
Figure 21E:
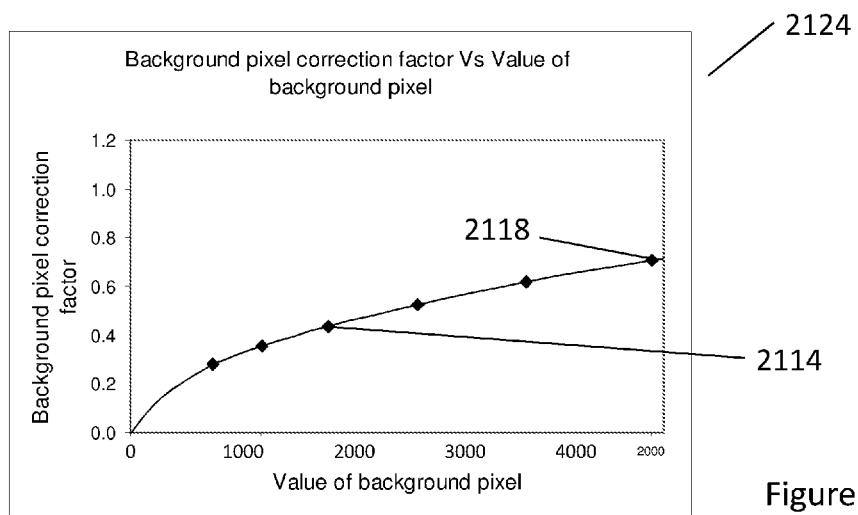
FIG. 21E is an enlargement of the function of FIG. 21D, in the usable range.

To handle this situation, if the x-ray mA is doubled so that current mA is 2×(mA-0), one can modify the x-axis units of the tone-correction function of FIG. 21C by also multiplying by 2 the x-axis values, to get the modified tone-correction function of FIG. 21D. The dynamic range to be used in the tone-correction function of FIG. 21D is still 0÷4095 (4095 is indicated by dashed line 2120 in FIG. 21D). In this range the actual tone-correction values range from 0.00 to about 0.71 and not up to 1.00 as before. Therefore, when the x-ray current during usage is changed relative to the x-ray current during the calculation of the tone-correction function, the x-scale (the "input scale") of the tone-correction function can be adjusted as described above, at the same proportions as the change in mA, and then be used to provide the required tone corrections under the new x-ray current. It would be appreciated that what more precisely determines this scale adjustment is the change in number of x-ray photons emitted from the x-ray tube towards the inspected object. Since this is generally considered to be reasonably proportional to the change in mA, mA is commonly used for this purpose.

As explained above, in reference to using tone-correction function, the tone correction function can be used without initial-processing of the background. In such a case the calculation of the tone-correction function should be made under the same conditions, that is, without implementation of initial-processing to the data used for the calculation of the tone-correction function.

Background Image Correction Function Calculation Using the Patient's Body

Figure 33B:
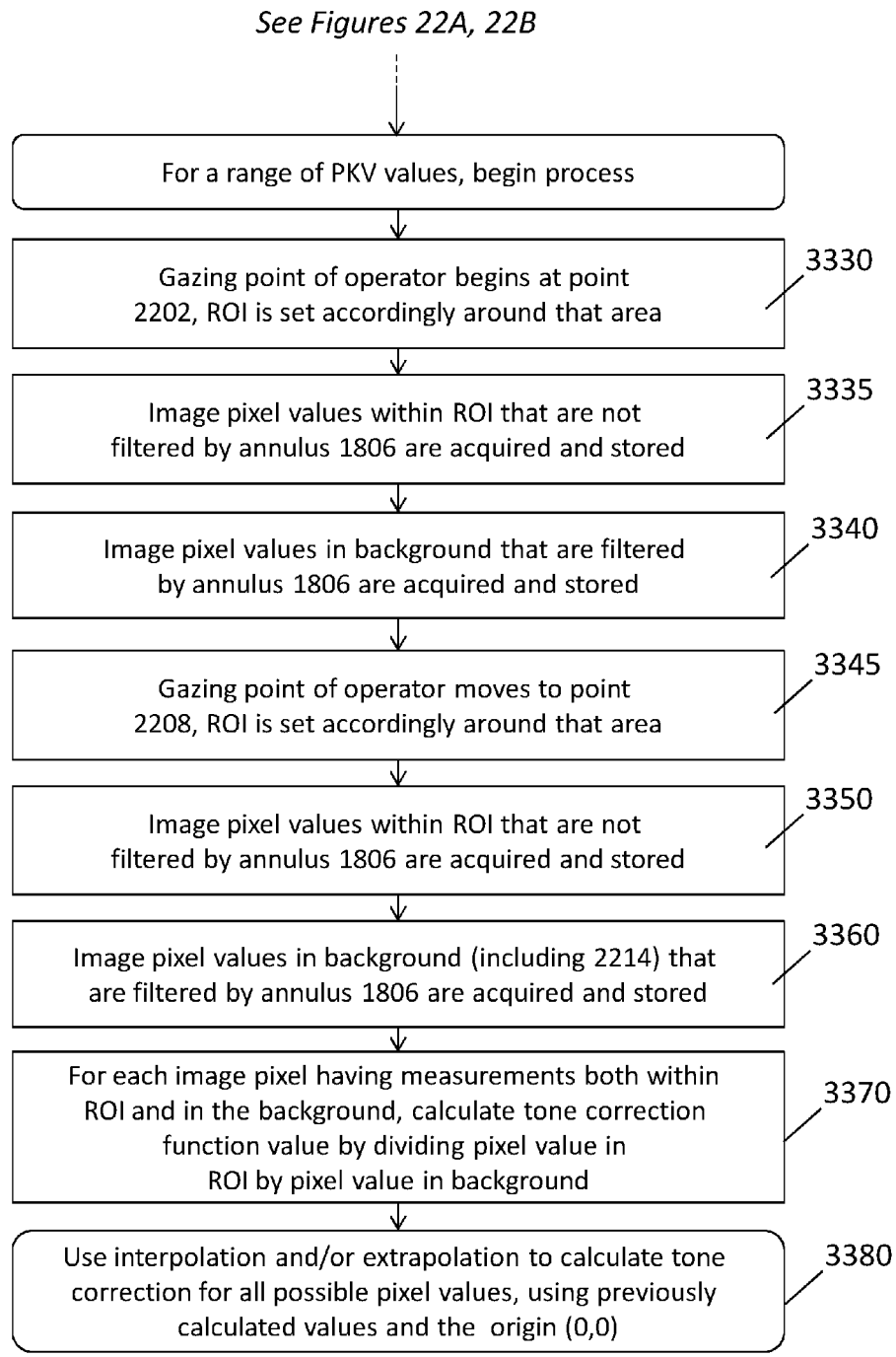
FIG. 33B is a flowchart referencing FIGS. 22A, 22B, describing the process of generating a tone correction function using the patient's body.

In another example of the invention, the calculation of the tone-correction function can be based on real time patient data (instead of a phantom as described above) and be optimized to the specific patient. To describe this example reference is made to FIG. 22A though FIG. 22B. The figures present the display layer but this is made only for convenience. The discussion made in reference to these figures refers also to the image processing and image memory data layers that are typical handled in 12 bit and also to the x-ray distribution and detector layers (either a flat detector or image intensifier or any theoretical x-ray detector), the geometries related to these layers are completely analog to those described in reference to FIG. 22A and FIG. 22B and the corresponding flowchart in FIG. 33B.

This example in provided with the same parameters selected for the description of the above examples such as: calculation of tone-correction function is made for a specific PKV and mA, background radiation is designed to be 10% of the ROI radiation when no patient or phantom is present as 110 of FIG. 1A etc. Deviations important for the explanation of this example will be presented explicitly. The following description will also adopt the above simplification of the collimator of FIG. 18A that annulus 1804 width is zero and only annulus central hole 1802 and annulus 1806 are considered. Expansion to the case of annulus 1804 is completely analog to the expansions described above.

Figure 22A:
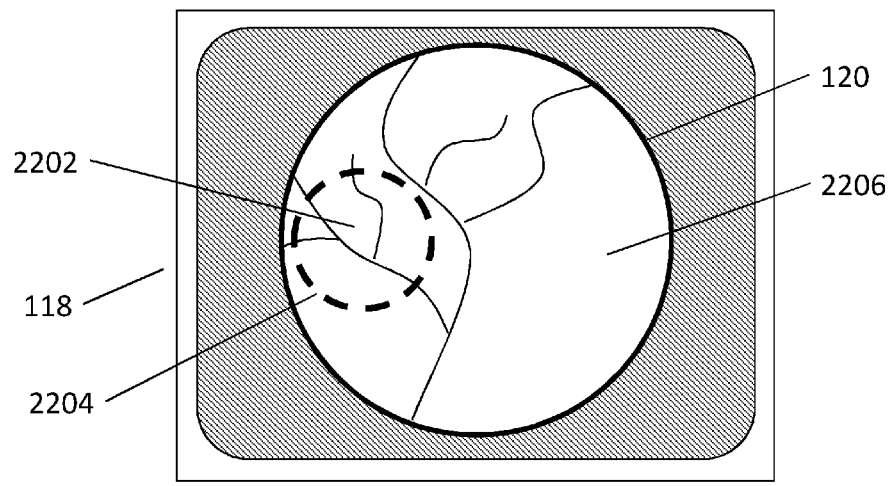
FIG. 22A provides an illustration of an ROI location and background for calculation of tone-correction function.

Reference is made now to FIG. 22A. During the time represented by FIG. 22A, the operator is gazing at point 2202. ROI 2204 is set, as described above, around gazing point 2202 (step 3330). High radiation level is directed now at ROI 2204 while background 2206 is exposed to ¹/₁₀ the radiation of the ROI. In the main flow the data is processed as described above (typically initial-processing of adding frames, optionally adjusting brightness using a multiplication factor and second processing using stored tone-correction function. Other image enhancement processes such as spatial filters may also be applied).

In a background flow, calculation of a tone-correction curve takes place, based on the data acquired from the image of patient 110.

From FIG. 22A, 2 types of data are acquired:
1. In ROI 2202 images data is acquired and stored (step 3335) (preferably in 12 bit but possible also in other accuracy such as 8 bit) for the x-ray spectrum that is not filtered by annulus 1806 of FIG. 18A.
2. In background 2206 images data is acquired and stored step 3340) (preferably in 12 bit but possible also in other accuracy such as 8 bit) for the x-ray spectrum that is filtered by annulus 1806 of FIG. 18A.

Figure 22B:
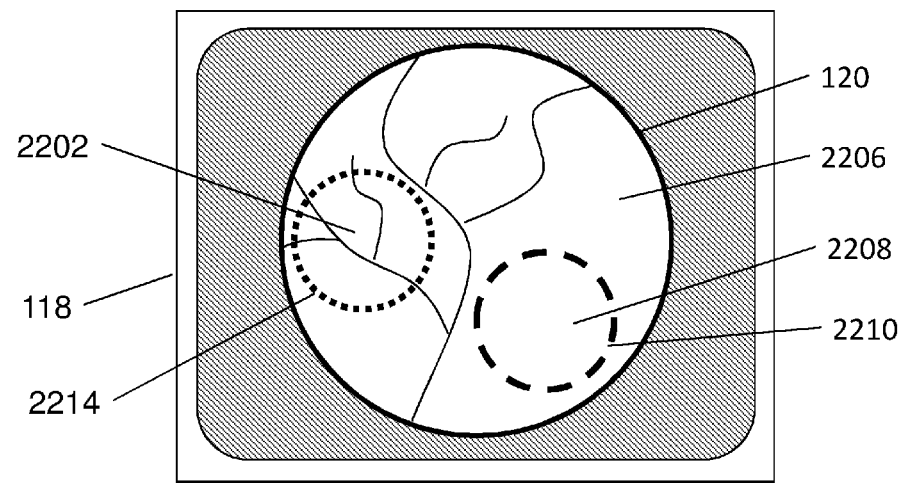
FIG. 22B provides an illustration of another ROI location and background for calculation of tone-correction function.

Now, after some time, the gazing point of the operator moves to point 2208 of FIG. 22B. The ROI follows the gazing point and is now shown as ROI 2210 (step 3345).

From FIG. 22B, 2 types of data are acquired:
3. In ROI 2210 images data is acquired and stored (step 3350) (preferably in 12 bit but possible also on other accuracy such as 8 bit) for the x-ray spectrum that is not filtered by annulus 1806 of FIG. 18A.
4. In background 2206 (that includes now also area 2214 that was previously ROI 2204) images data is acquired and stored (step 3360) (preferably in 12 bit but possible also on other accuracy such as 8 bit) for the x-ray spectrum that is filtered by annulus 1806 of FIG. 18A.

With this collected data tone-correction function can be calculated.

In one approach, for each of the frames initial-processing is performed (frames summing and brightness adjustment). The other approach of calculating tone-correction function without initial processing will not be discussed as it is already well explained in above examples.

At this stage, using the initially-processed data, values of pixels (part or all) from ROI 2204 are divided by values of the corresponding pixels from background area 2214 (step 3370) to provide the tone-correction background pixel correction factor (output) of FIG. 21C for the corresponding values of background pixels (input) in area 2214 of FIG. 22B.

Also, using the initially-processed data, values of pixels (part or all) from ROI 2210 are divided by values of the corresponding pixels from the corresponding background area 2206 of the data acquired at the stage of FIG. 22A to provide the tone-correction background pixel correction factor of FIG. 21C for the corresponding values of background pixels in area 2206 of FIG. 22A.

This provides a set of multiple input points for the tone-correction function that have corresponding calculated background pixel correction factor. Due to noise, this set typically includes also input values, of the same value, that have different output values. This statistical distribution of output values can be resolved by any method, including averaging of the output values, the median or any other method. In this example the average approach is adopted. This way, the multiple input values of possible different output values are reduced to a single input value with a single output value.

Having this set of points, a curve fitting can be performed to fit this set (and preferably also the (0,0) point) to calculate the tone-correction function based on real patient data (step 3380).

It would be appreciated that only one ROI position can be used for this purpose as well and more than 2 ROI positions demonstrated in the above example.

It would also be appreciated that the more different ROI locations are used, it is more probable to get more points in the set used for curve fitting and thus, a more accurate tone correction function.

It would also be appreciated that more data can be used for the calculation to improve accuracy. For example, if the example is based on 10 fps and the position of the ROI in FIG. 22A lasted for more than 5 seconds, then the ROI and background data could be collected from all the frames made during the last 5 seconds before moving the gazing point to the position of FIG. 22B. In the same manner, if ROI position in FIG. 22B lasted for more than 3 seconds, then the ROI and background data could be collected from all the frames made during the first 3 seconds after moving the gazing point to the position of FIG. 22B.

Every such data can be temporally averaged, thus reduce noise errors and provide more accurate values for the curve fitting of the tone-correction function.

It would also be appreciated that such calculation of tone-correction function can be calculated during a clinical procedure with a patient, where the first calculation is made right after the ROI moved first from one location to another and the tone-correction function can be re-calculated in any time interval using the additionally accumulated data.

At the beginning of the process a default tone-correction function can be used and replaced by the first calculated tone-correction function right after its' calculation and further, replace each tone-correction function by the successively calculated tone-correction function that is improved due to the additional data.

It would be appreciated that tone correction calculation data collected from multiple patients can be used to generate one or more "general patient" tone-correction functions that can be used for future patients.

Such data can be improved with every additional patient whose data is added to the already stored data and processed together.

As explained above, in reference to using tone-correction function, the tone correction function can be used without initial-processing of the background. In such a case the calculation of the tone-correction function should be made under the same conditions, that is, without implementation of initial-processing to the data used for the calculation of the tone-correction function.

It has been provided above, as an example that one may divide annulus 1824 of FIG. 18 to 8 annuluses of equal radius step so that the average DPP in the smallest annulus #1 is $9/10$ of 1822, the average DPP in the next annulus #2 is $8/10$ of 1822, annulus #3 is $7/10$ and so on until the last annulus #8 that has $2/10$ DPP of 1822. In this example it is assumed that each annulus, having a specific internal and external radius provides DPP that is independent of angle 1828 of FIG. 18A.

Figure 23A:
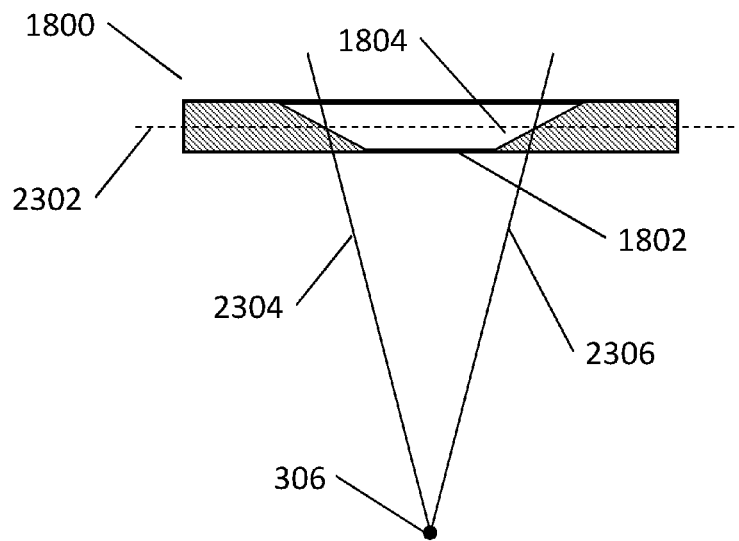
FIG. 23A illustrates the path of two x-ray rays through the collimator of FIG. 18 at one collimator position.

This method works accurately when the x-ray source is abeam the center of the aperture as shown in FIG. 23A. In FIG. 23A, dashed line 2302 marks the middle layer of collimator 1800 (half thickness). X-ray rays (rays) 2304 and 2306 cross the upper surface of annulus 1804 at the same point line 2302 crosses the upper surface of annulus 1804. This represents that the rays pass the collimator at the same radius but at different angles. Since the x-ray source is abeam the center of aperture 1802 and annulus 1804, the symmetry implies that in the path of each of rays 2304 and 2306 the material of collimator 1800 is the same. Therefore attenuation is the same and independent of angle 1828 of FIG. 18A.

Figure 23B:
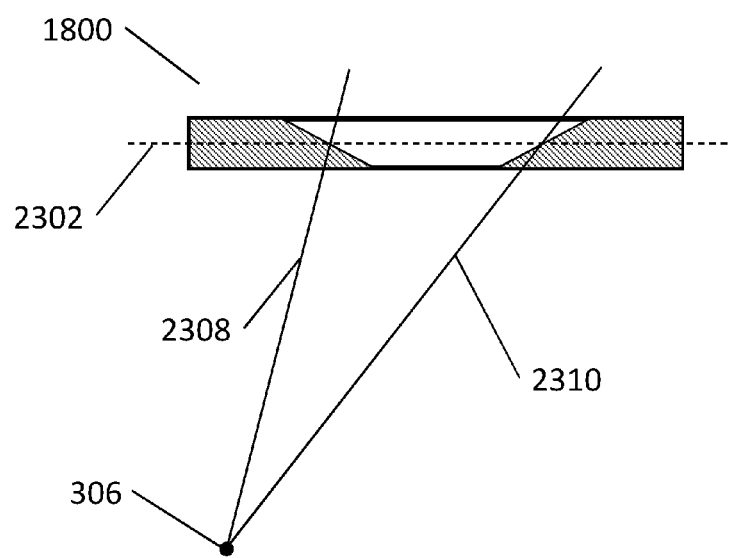
FIG. 23B illustrates the path of two x-ray rays through the collimator of FIG. 18 at a second collimator position.

FIG. 23B presents the situation where collimator 1800 has moved to the right. Rays 2308 that is analog to ray 2304 and ray 2310 that is analog to ray 2306, although passing collimator 1800 at the same radius, do not have the same incidence angle at the collimator surface. The path inside the collimator for rays 2308 and 2310 is different and therefore they have different attenuation. To overcome this, a consideration of the phenomenon is made and introduced to the DPP calculations.

In one approach, a correction is made to the DPP as a parameter of collimator 1800 position. This can be done using x-ray absorption coefficients of the collimator material and collimator geometry. Since the distance source 306 to collimator 1800 also affects DPP Vs collimator position, this distance can also be considered in the calculations to further enhance accuracy.

An alternative to DPP calculation, the DPP can be measured for different positions of collimator 1800 and be used as attenuation data. Accuracy can be further increased by measurement of DPP also as a function of source 306 to collimator 1800 distance.

Figure 24A:
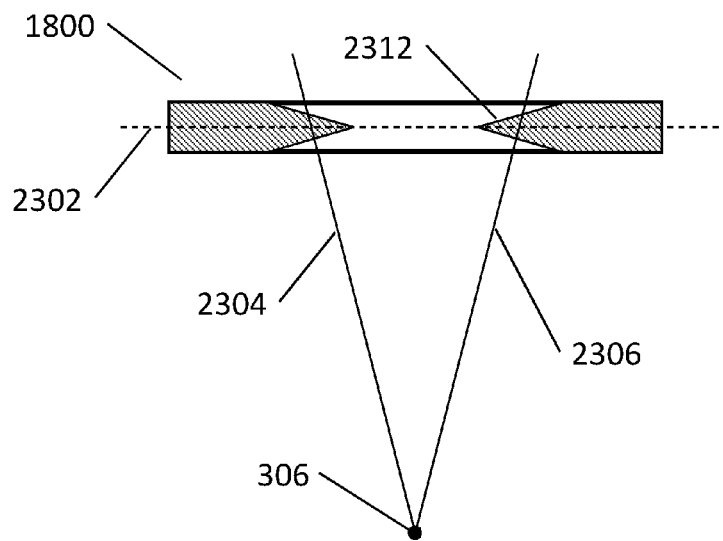
FIG. 24A illustrates the path of two x-ray rays through a collimator with symmetric aperture edge at one collimator position.
Figure 24B:
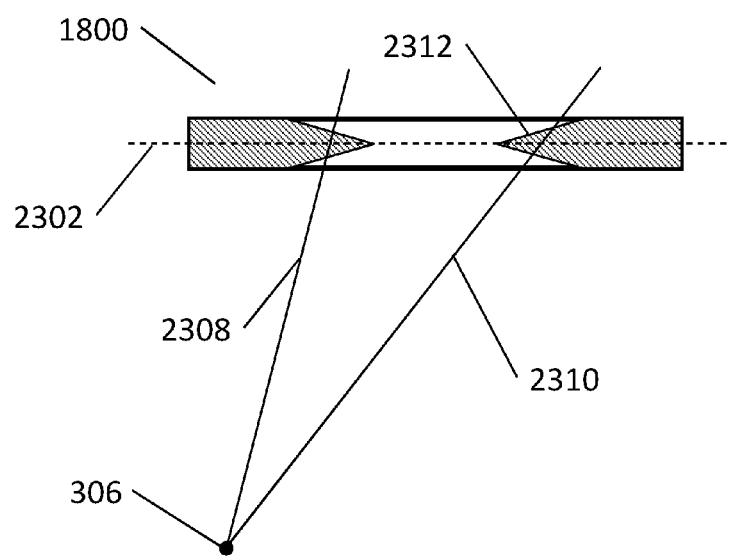
FIG. 24B illustrates the path of two x-ray rays through a collimator with symmetric aperture edge at a second collimator position.

Reduction to sensitivity of attenuation to the incidence angle of the ray can be provided by a symmetric or nearly symmetric aperture edge as shown in FIG. 24A, numerical reference 2312. With this design, the difference of the path in the collimator material between ray 2308 and ray 2310 is smaller than with the aperture edge of FIGS. 23A and 23B. It would be appreciated that design optimization can be made to each side of the aperture edge that is not symmetric to line 2302 to minimize the sensitivity of the attenuation to the ray angle of incidence. The result of such optimization would be two surfaces of the aperture edge (upper and lower surfaces of annulus 2312 in FIGS. 24A and 24B) that are not symmetric to line 2302.

Figure 25:
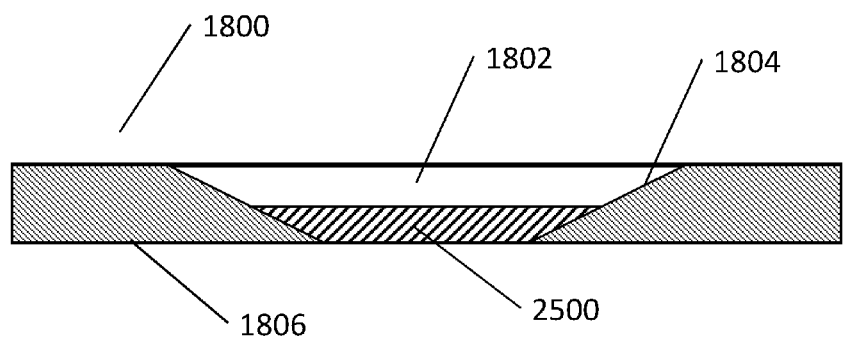
FIG. 25 illustrates a modified example of collimator of FIG. 18.

Reference is made now to FIG. 25 illustrating a modified example of collimator 1800. It is common to filter x-ray radiation, using layers such as aluminum (Al) layers of various thicknesses to change the spectral distribution of the x-ray radiation. Such filtering typically (but not limited to) reduces low energy part of the x-ray spectrum. The collimator of FIG. 18, with most materials, would do the same. Now, if the collimator of FIG. 18 is used with another layer of filter, the other layer of filter which is designed to cover the complete x-ray beam cross section, does not only provide the desired results in the area of aperture 1802 but it adds this effect also to the area outside the aperture, 1806, on top of what the collimator already does. This might be undesired. To overcome this, instead of using a filter that covers the complete x-ray beam cross section, a smaller filter 2500 is added in the ROI area only, as a part of collimator 1800. This way the filter acts in the aperture area 1802 as desired but does not add additional undesired filtering in area 1806.

Attention is made now to FIG. 26 which presents an exemplary system for carrying out the invention.

Typically in x-ray systems, an ROI that is centered in image 120 (such as ROI 200 of FIG. 2) and has a fixed position is used for image analysis and for generating parameters to drive x-ray tube 100 and modify image 120. Parameters such as average value, maximum value and contrast may be calculated for this area. Such parameters are typically used to optimize the x-ray tube operation (such as mA, mAs and KVp).

In this example eye tracker 128 is used to provide x-ray controller 130 with the gazing coordinates of user 122. Instead of using a fixed position ROI as in the prior art, the ROI is moving according to the gazing coordinate so that it includes the gazing point or it is near the gazing point. With this adjustment of the ROI position as a function of the gazing point, the analysis and parameters calculated from the ROI to drive the x-ray tube and modify image 120 are made from an ROI that is located according to the gazing point instead of a fixed ROI, that may sometimes be at a distance from the gazing point and not represent the image information that is relevant to the gazing point.

For example, the center of the image might include mainly bones (such as vertebrae and sternum) that constitute a dark part of the image and the side of image 120 includes mainly lung which is a bright part of the image. With a fixed center ROI, x-ray parameters and image adjustment (such as brightness, contrast and tone-correction) will be adjusted so that the central image will come out clear. This adjustment will drive excess x-ray to the lung area which is outside the ROI and also might increase the brightness of the lungs area beyond an acceptable image quality, resulting in unusable lungs imaging. When the user looks at the lung, the image quality might be useless. In such cases the user might move the patient or the c-arm system to a new position so that the lung enters the centered fixed position ROI. With the current example of moving ROI, as a function of the gazing point, when the user gazes at the lung, at the side of image 120, the ROI is moved also to the lungs area and the x-ray parameters and image adjustment are made according to the displaced ROI, as required for the lungs. This would also, in this example, typically reduce x-ray intensity and reduce patient's exposure according to the gazing point.

It would be appreciated that many relations between the gazing point and the ROI are available. Such relations may include ROI position relative to the gazing point, ROI size relative to the gazing point, ROI shape relative to the gazing point (in a rectangular image the ROI may be circular in the central area and rectangular near the corners of the image or assume any other shape, including a combination of an arch and 90 degrees straight edges). Also, the ROI may be centered about the gazing point but also may have a variable location relative to the gazing point. Such a variable location may be dependent on any combination of the gazing point location, the dynamics of the gazing point and the fixed or variable shape of the ROI. The ROI may be fixed in position and only change size as a function of the gazing point. One such example is a circular ROI centered about image 120, where the diameter of the ROI changes according to the gazing point. In one example the ROI diameter may increase when the gazing point distance from the center of image 120 increases.

It should be appreciated that an eye tracker term in the current invention is used to indicate any device that can provide information related to the gazing point of the user.

In the example of FIG. 26, it would be appreciated that the invention is not limited to an eye tracker that typically provides automatically information of the gazing point of the user. In an example of the current invention the eye tracker can be replaced by any input device that affects the position and/or the shape of the ROI. For example, a joy-stick, a keyboard, an interactive display such as the display of a tablet PC or a smart-phone, a gesture reading device, a voice interpreter or any other suitable device can be used to determine coordinates relative to image 120, and the ROI position and/or shape will change according to such input.

Tone changes are described above using the terms tone-correction. Although in many examples the term tone-correction is used this does not limit the examples to the sense of "correction" and all these examples can be interpreted in the sense of any tone changes of the image, including such that may include any desired image modification. Tone-correction term should be interpreted as a tone change that may include any desired image modification.

Multiple ROI Collimator

FIGS. 18A and 18B disclose a collimator with partially transparent background (1806) and fully transparent ROI section (1802) where the diameter of the ROI exposes area 1822 (FIG. 18D) and partially transparent area 1806 exposes area 1826 in FIG. 18D. For simplicity, transition area 1804 in FIG. 18A and 1824 in FIG. 18D are ignored in this example but it will be appreciated that this example can also include a version with the transition area.

Figure 34A:
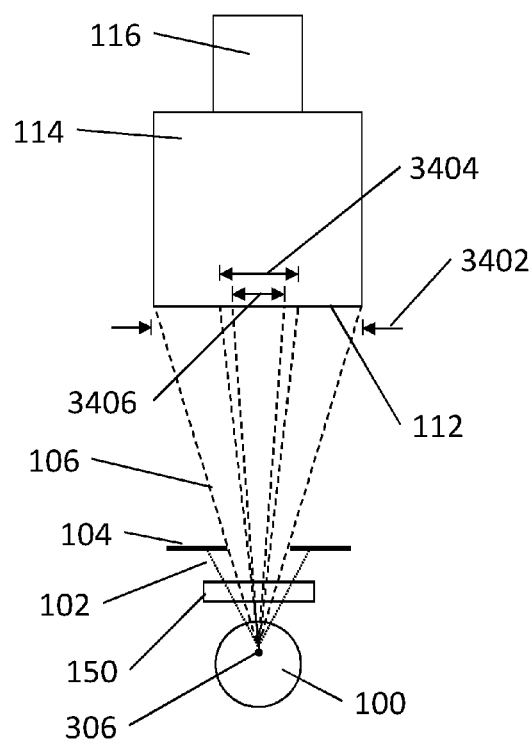
FIG. 34A is a schematic diagram of an x-ray system with a detector utilized with different zoom levels.

For example, in FIG. 34A, at the input plane of Image Intensifier 112, the fully exposed area 3402 by x-ray beam 106 may be 12" in diameter. The ROI exposed area may be designed, for example, to ⅓ in diameter of the full area 3402, 4", as shown by numerical indicator 3404. In an example of 1024×1024 pixels imaging area, the 12" diameter is imaged on nearly 1024 pixels (1826 AND 1824 of FIG. 18D) and the ROI is imaged on nearly 1024/3=341 pixels in diameter (1822 of FIG. 18D).

In some cases, the user may activate zoom function of image intensifier 114 so that only a part of input area 112 is imaged onto camera 116 sensor. For example, instead of 12" only 9" diameter from input area 112 is imaged onto camera 116 sensor. In such example an area of diameter 9" is imaged onto 1024×1024 pixels of the image. The user may expect that the ROI area will still be a ⅓ in diameter of displayed image 120. In this case 3" diameter area of input 112 should be exposed onto 341 pixels as ROI diameter and not 4" as before, as shown by numerical indicator 3406.

In one example, the adjustment of the ROI radiation area diameter from 4" to 3" can be done by moving collimator 1800, with ROI area 1802 designed for 4" diameter towards image intensifier 114 to create a new distance of collimator 1800 from x-ray focal point 306. If D1 is the distance of collimator 1800 from focal point 306 for ROI of 4" diameter, then to get an ROI of 3" diameter the new distance of collimator 1800 from focal point 306 should be for this example D1×¾. This proportion calculation example can be used also for other ROI diameters. Collimator 1800 can be moved away or closer to focal point 306 using any motorized mechanical system. It would be appreciated that in this example collimator 1800 is represented in FIG. 34A by a more general collimator 150 and also, other collimators represented by collimator 150 (as explained above) can be used according to this example.

Figures 34B, 34C:
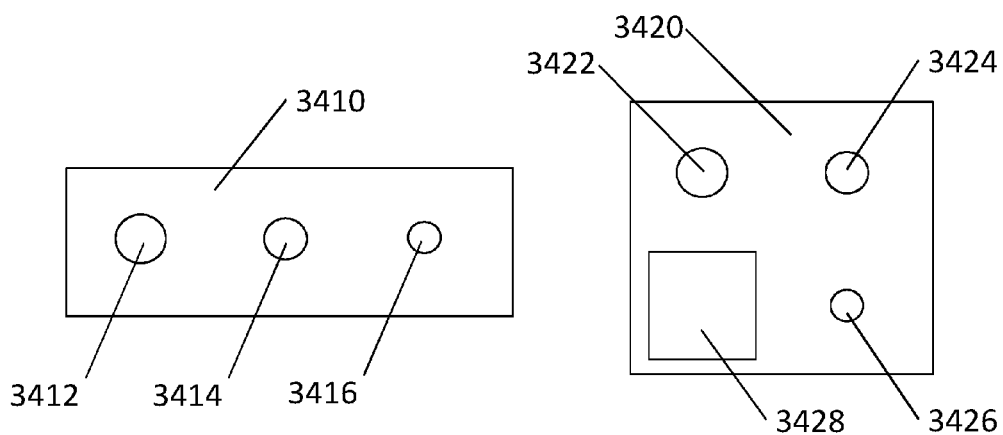
FIG. 34B is a diagram of an example of a collimator with 3 ROI elements.
FIG. 34C is a diagram of another example of a collimator with 3 ROI elements.

In another example, instead of moving collimator 1800 away or towards focal point 306, collimators such as collimator 1800 can be designed according to the example of FIG. 34B and shown by collimator 3410. This collimator has 3 holes for ROI of 3 different sizes. For example, each ROI hole diameter is designed to project ⅓ of the exposed area diameter. For example, if image intensifier input area 112 diameter is 12" and it has 2 zoom options 9" and 6" then hole 3414 will be 9/12 of hole 3412 and hole 3416 will be 6/12 of hole 3412 in diameter. For each zoom of image intensifier 114 the corresponding area of collimator 3410 is used so that the ROI is maintained ⅓ in diameter of image 120 diameter.

Collimator 3420 of FIG. 34C is another example enabling adjustment of ROI hole to the zoom options of the image intensifier 114 in a similar manner to collimator 3410 but with a different geometry.

Rectangular hole 3428 (that can also be a relatively large circular hole) provides a collimator area which does not limit the x-ray and enables conventional usage of such system.

It would be appreciated that collimators with a plurality of holes such as those of FIGS. 34B and 35C can also be moved perpendicularly to the collimator plane to provide variable size ROI onto input area 112. By combining more than one hole size and movement perpendicularly to the collimator area, more ROI sizes can be provided with reduced vertical movement range comparing to one hole.

As the variety of holes dimensions increases, a smaller motion range is required perpendicularly to the collimator plane to cover more ROI sizes.

It would also be appreciated that the examples of FIG. 34 can be combined with any of the hole edges as shown in reference to FIGS. 23, 24 and 25.

Reference is made now to FIG. 35A providing another example of collimator 3500 of the present invention. Coordinate system 126 is present in FIG. 35A to provide orientation in reference to FIG. 1B.

X-ray focal point 306 is shown and a cone-shaped x-ray beam 106 is projected upwards towards input area 112 (not shown in FIG. 35A—see FIG. 34A).

Plates 3501, 3502, 3503 and 3504 are partially transparent to x-ray. In this example we shall assume that each such plate transmits 30% of beam 106 but it would be appreciated that other transmission levels are available. Plates 3501, 3502, 3503 and 3504 can be made from any suitable material, considering the desired effect of the spectral distribution of the transmitted x-ray beam. For example, copper plates can be used.

Dashed circle 106A represents x-ray cone 106 cross section at generally the plane of collimator 3500. Except for a rectangular shaped x-ray beam, 3510, the rest of the beam (106B) intensity is reduced due to plates 3501, 3502, 3503 and 3504. Where there is only one layer of plates the x-ray beam is reduced to 30% of its original intensity. In areas where two plates overlap the x-ray beam is reduced to 9% of its original intensity (30%×30%), With this example ROI 3510 is now rectangular. Motors can move plates 3501, 3502, 3503 and 3504 as explained in FIG. 35B.

It would be appreciated that due to x-ray spectral changes depending on thickness of filtering material, the result of 2 layers, each allowing 30% of the incident x-ray to pass, is typically not 9% but depends on the original x-ray spectrum and the material of the filter. Yet, in the disclosure of this invention we shall assume such relations (30%×30%=9%) to simplify the description of the invention. Actual absorbance of one layer Vs 2 layers can be designed per the needs of any specific application and it will be ignored in this disclosure. In FIG. 35B the components of the motorizing elements are detailed in reference to plate 3501. The other 3 plates mechanism is analogue.

Motor 3501A drives screw 3501C that moves nut 3501B. Nut 3501B is connected to plate 3501 therefore enables plate 3501 to move in directions of arrow 3501D. Therefore, each plate can move independently of the other plates as indicated by dual-head arrow for each plate. Rails that may be used to support the plates and enable motion are not shown in this figure. It would be appreciated that the specific motion mechanism described here is provided to explain the invention and that the scope of the invention is not limited to this motion mechanism.

In the example of FIG. 35B hole 3512 is at the center of beam 106 (as shown by the beam cross section 106A) and it has a certain size.

In the example of FIG. 35C plates 3503 and 3504 were moved to the right without changing the distance between these plates. Plates 3501 and 3502 were moved upwards without changing the distance between these plates. As a result hole 3512 moved towards the top-right edge of x-ray beam cross-section 106A but without changing its' dimensions.

Figures 35D, 35E:
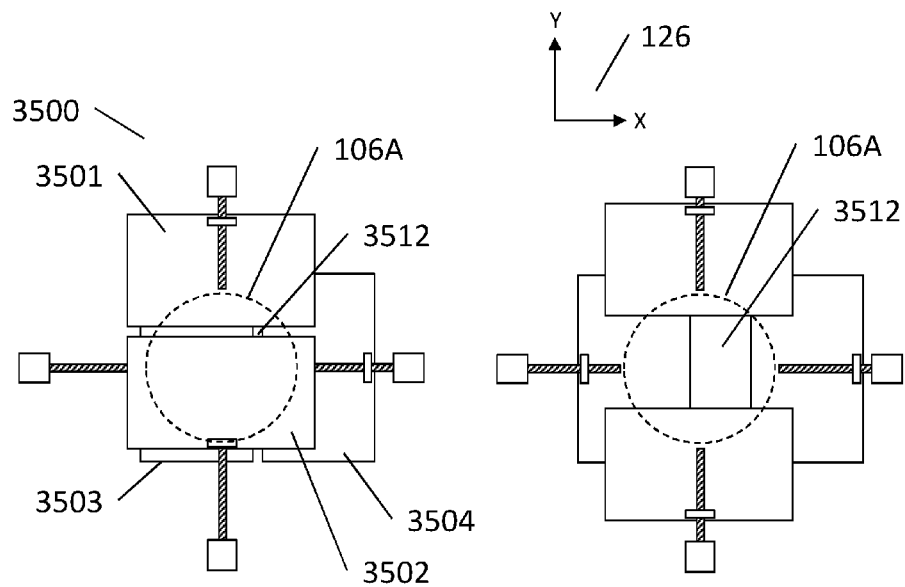
FIG. 35D is a top view of the collimator of FIG. 35C with a smaller ROI.
FIG. 35E is a top view of the collimator of FIG. 35C with a larger ROI and with a different geometry.

In the example of FIG. 35D hole 3512 is also generally at the top-right area of x-ray beam cross-section 106A but the distance between plates 3501 and 3502 was reduced and also the distance between plates 3503 and 3504 was reduced. As a result the size of hole 3512 was reduced and the resultant ROI is smaller now.

In FIG. 35E the hole is still in the upper-right area of x-ray beam cross-section 106A but the distance between plates was changed again to produce a large rectangle that is also particularly longer in the Y direction than in the X direction. The ROI therefore becomes larger and also of a different shape. With this example of collimator 3500 therefore the ROI of image 120 can not only be moved across the area of image 120 to the desired location but also the size and aspect ratio of the ROI can be changed as desired, to compensate for zoom in image intensifier 114 or for other reasons.

It would be appreciated that although FIG. 35 implies that pairs of collimator plates are arranged in the same plane, this is not a limitation of the invention and each of the plates of a plates pair can be positioned in a different plane.

Figure 36:
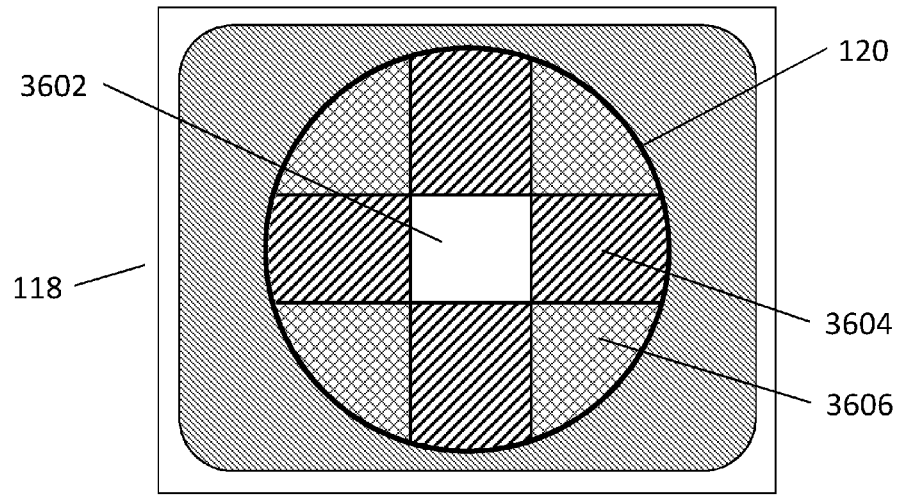
FIG. 36 illustrates the x-ray intensity distribution in different areas of the image when the ROI is in the position presented in FIG. 35B.

Reference is made now to FIG. 36, illustrating the x-ray intensity distribution in different areas of image 120 when the ROI is in the position presented in FIG. 35B. In this example there is no object (patient) between collimator 3500 and input area 112 so, ideally, without collimator 3500 the x-ray radiation over input area 112 would be uniform. In this example, as a result of collimator 3500 the area of image 120 is divided to 3 intensity areas: 3602, the ROI, where the original 100% intensity is, 3604 (4 such areas) where the intensity is 30% of the ROI and 3606 (4 such areas) where the intensity is 9% of the ROI.

The above described methods to correct background are fully applicable to correct the background of the present example where each of areas 3604 and 3606 require its own correction parameters.

It would be appreciated therefore that the current example can be used together with the above described correction methods. It would also be appreciated that edge transition concepts such as those associated with FIGS. 18 and 24 are applicable also to the edges of the plates of collimator 3500 that are facing hole 3512.

It would be appreciated that although the above was described in reference to an image intensifier it is applicable to any detector, including a flat panel detector. The geometry of the detector, the zoom area and the ROI can be of a mixed nature and do not need to be of the same nature (i.e. circular or rectangular or another geometry).

It would be appreciated by those skilled in the art that the above described methods and technologies are not limited to the configurations and methods mentioned herein above as examples. These are provided as examples and other configurations and methods can be used to optimize final result, depending on the specific design and the set of technologies implemented in the production of the design.

The herein above embodiments are described in a way of example only and do not specify a limited scope of the invention.

The scope of the invention is defined solely by the claims provided herein below.

The invention claimed is:

1. An x-ray system comprising:
   an x-ray source;
   a detector having an input area;
   a monitor configured to display detected images;
   means for selecting a Region of Interest (ROI) in any location on said displayed image;
   means for selecting a zoom thereby determining a fraction of said input area to be displayed on said monitor;
   a collimator comprising a plate movable in any direction on a plane parallel to said detector input area, said plate comprises a plurality of fixed size holes, each having a different size corresponding to different determined fractions of said input area, each one of said holes configured for projecting said x-ray radiation at said selected location of said ROI, according to said determined fraction of said input area to be displayed on said monitor;
   said collimator is partially transparent to x-ray radiation outside said plurality of holes; and
   means for moving said collimator's plate;
   said moving means configured to move said collimator's plate for placing a one of said holes according to said selected location of said Region of Interest (ROI) on said displayed image according to said determined fraction of said input area to be displayed on said monitor.

2. An x-ray system comprising:
an x-ray source;
a detector having an input area;
a monitor configured to display detected images;
means for determining the location of a Region of Interest (ROI) of a patient on said displayed image; and
a collimator comprising means for projecting said region of interest (ROI) on a selected fraction of said input area exposed by said x-ray source, said collimator comprising two pairs of plates mounted in planes generally parallel to the detector input surface plane:
first and second plates forming the first pair are mounted with mutually facing edges generally parallel to each other and at a distance from each other;
third and fourth plates forming the second pair are mounted with mutually facing edges generally parallel to each other and at a distance from each other; and
said four plates defining a fully transparent gap therebetween for projecting said region of interest (ROI),
wherein each of said four plates is partially transparent to the x-ray radiation;
means for moving each one of said plates independently of the other plates in its plane, in direction perpendicular to the edge facing the edge of the other plate in the pair; and
means for modifying the appearance of the image received through the plates according to the image received through the gap by changing the value of at least one pixel.

3. The system of claim 2, wherein each one of said four plates is partially transparent to x-ray radiation and wherein the positioning of said four plates is configured to create a fully transparent area in a gap between the plates for projecting said region of interest (ROI), first partially transparent areas covered by a single plate and a second partially transparent areas covered by two plates and wherein said means for modifying comprise means for adjusting the image received through the single plates and the image received through the two plates to the image received through the gap by changing the value of at least one pixel.

4. The x-ray system of claim 1, further comprising:
an image processing unit connected between said detector and said monitor, said image processing unit configured to modify the detected image displayed on said monitor in the area outside said ROI according to the image part in said ROI.

5. The x-ray system of claim 4, wherein said image modification comprises determining a tone reproduction function for the image.

6. The x-ray system of claim 5, wherein said tone reproduction function is implemented as one of brightness function, a contrast function, a gamma function, an offset function, an n-degree linear function and a non-linear function.

7. The x-ray system of claim 4, wherein said image modification comprises controlling said x-ray source parameters.

8. The x-ray system of claim 7, wherein said x-ray source parameters are selected from the group consisting of: current, Peak Kilo Voltage (PKV), pulse length and Automatic Gain Control (AGC).

9. The x-ray system of claim 2, further comprising:
an image processing unit connected between said detector and said monitor, said image processing unit configured to optimize modify the detected image displayed for display on said monitor in the area outside said ROI according to the image part in said ROI.

10. The system of claim 9, wherein said image modification comprises determining a tone reproduction function for the image.

11. The x-ray system of claim 10, wherein said tone reproduction function is implemented as one of brightness function, a contrast function, a gamma function, an offset function, an n-degree linear function and a non-linear function.

12. The x-ray system of claim 11, wherein said image modification comprises controlling said x-ray source parameters.

13. The x-ray system of claim 12, wherein said x-ray source parameters are selected from the group consisting of: current, Peak Kilo Voltage (PKV), pulse length and Automatic Gain Control (AGC).

14. The x-ray system of claim 2 wherein said collimator is configured to move in accordance to the zoom setting of the detector and the determined ROI.

15. The x-ray system of claim 1, wherein said collimator is configured to incorporate pre-set positions in accordance to pre-set zoom options of said detector.

16. The x-ray system of claim 1, wherein said collimator is also moveable in a direction perpendicular to said collimator plane.

17. A method of controlling a display size of a Region of Interest (ROI) in an image of an x-ray irradiated area, comprising:
providing an x-ray system comprising:
an x-ray source;
a detector having an input area;
a monitor configured to display detected images;
means for selecting a Region of Interest (ROI) in any location on said displayed image;
means for selecting a zoom thereby determining a fraction of said input area to be displayed on said monitor;
a collimator comprising a plate movable in any direction on a plane parallel to said detector input area, said plate comprises a plurality of fixed size holes, each having a different size corresponding to different determined fractions of said input area, each one of said holes configured for projecting said x-ray radiation at said selected location of said ROI, according to said determined fraction of said input area to be displayed on said monitor; said collimator is partially transparent to x-ray radiation outside said plurality of holes; and
means for moving said collimator's plate;
said moving means configured to move said collimator's plate for placing one of said holes according to said selected location of said ROI on said displayed image according to said determined fraction of said input area to be displayed on said monitor;
selecting an ROI in any location on said displayed image;
setting said detector to a zoom factor thereby determining a fraction of said input area to be displayed on said monitor;
selecting one of said plurality of holes according to said selected ROI and said determined fraction of said input area to be displayed on said monitor; and
moving said collimator's plate to position said selected hole according to a location of said selected ROI.

18. A method of controlling a display size of a ROI in an image of an x-ray irradiated area, comprising:
providing an x-ray system comprising:
an x-ray source;
a detector having an input area; and a collimator comprising means for projecting a region of interest (ROI) on a selected fraction of said input area exposed by said x-ray source;

said collimator comprises two pairs of plates mounted in planes generally parallel to the detector input surface plane:

first and second plates forming the first pair are mounted with mutually facing edges generally parallel to each other and at a distance from each other;

third and fourth plates forming the second pair are mounted with mutually facing edges generally parallel to each other and at a distance from each other;

wherein each of said four plates is partially transparent to the x-ray radiation; and means for moving each one of said plates independently in its plane, in direction perpendicular to the edge facing the edge of the other plate in the pair; and determining location and size of an exposed area image on said detector input area by moving at least one of said plates to form a fully transparent gap between said plates; and modifying the appearance of the image received through the plates to the image received through the gap by correcting the value of at least one pixel.

19. The method of claim 18, further comprising an image processing unit connected between said detector and said monitor, said image processing unit configured to modify the detected image for display on said monitor according to the image part in said ROI, wherein each one of said four plates is partially transparent to x-ray radiation.

20. The method of claim 17, wherein said x-ray system further comprises:

an image processing unit connected between said detector and said monitor;

said method further comprises:

modifying said detected image displayed on said monitor in the area outside said ROI according to the image part in said ROI.

21. The method of claim 20, wherein said image modification comprises determining a tone reproduction function for the image.

22. The method of claim 21, wherein said tone reproduction function is implemented as one of brightness function, a contrast function, a gamma function, an offset function, an n-degree linear function and a non-linear function.

23. The method of claim 20, wherein said image modification comprises controlling said x-ray source parameters.

24. The method of claim 23, wherein said x-ray source parameters are selected from the group consisting of: current, Peak Kilo Voltage (PKV), pulse length and Automatic Gain Control (AGC).

25. The method of claim 17, wherein said collimator is configured to incorporate pre-set positions in accordance to pre-set zoom options of said detector.

26. The method of claim 17, wherein said collimator is also moveable in a direction perpendicular to said collimator plane.

* * * * *